US008088968B2

(12) United States Patent
Liddle et al.

(10) Patent No.: US 8,088,968 B2
(45) Date of Patent: *Jan. 3, 2012

(54) TRANSGENIC ANIMALS FOR ANALYZING CYP3A4 CYTOCHROME P450 GENE REGULATION

(75) Inventors: Christopher Liddle, Chatswood (AU); Bryan James Goodwin, Morrisville, NC (US); Graham Robertson, Sydney (AU)

(73) Assignee: The University of Sydney, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/463,246

(22) Filed: May 8, 2009

(65) Prior Publication Data
US 2009/0288181 A1    Nov. 19, 2009

Related U.S. Application Data

(63) Continuation of application No. 10/415,607, filed as application No. PCT/AU01/01407 on Nov. 1, 2001, now Pat. No. 7,531,712.

(30) Foreign Application Priority Data

Nov. 1, 2000   (AU) ..................................... PR 1161
May 10, 2001  (AU) ..................................... PR 4901

(51) Int. Cl.
G01N 33/00     (2006.01)
A01K 67/00     (2006.01)
A01K 67/027    (2006.01)
C12N 5/00      (2006.01)
C12N 15/11     (2006.01)

(52) U.S. Cl. .................. 800/3; 800/14; 800/18; 435/325
(58) Field of Classification Search .................. 800/3, 8, 800/18
See application file for complete search history.

(56) References Cited

U.S. PATENT DOCUMENTS

| 4,997,757 A | 3/1991 | Schiestl |
| 5,429,948 A | 7/1995 | Crespi et al. |
| 5,849,998 A | 12/1998 | Gottesman et al. |
| 6,432,639 B1 | 8/2002 | Lichter et al. |
| 7,449,567 B2 | 11/2008 | Zhang |
| 7,449,615 B2 | 11/2008 | Contag |
| 2002/0138855 A1* | 9/2002 | Zhang et al. ...................... 800/3 |
| 2002/0150915 A1 | 10/2002 | Berkenstam et al. |

FOREIGN PATENT DOCUMENTS

| EP | 644267 | 3/1995 |
| EP | 1206906 | 5/2002 |
| WO | WO 99/13106 | 3/1999 |
| WO | WO 99/35246 | 7/1999 |
| WO | WO 99/48915 | 9/1999 |
| WO | WO 99/61622 | 12/1999 |
| WO | WO 01/11951 | 2/2001 |
| WO | WO 01/20025 | 3/2001 |
| WO | WO 01/20026 | 3/2001 |
| WO | WO 01/79845 | 10/2001 |
| WO | WO 02/08451 | 1/2002 |
| WO | WO 02/25270 | 3/2002 |
| WO | WO 02/036784 | 10/2002 |
| WO | WO 02/083897 | 10/2002 |
| WO | WO 02/088305 | 11/2002 |

OTHER PUBLICATIONS

Hashimoto et al., 1993, Eur. J. Biochem., vol. 218, pp. 585-595.*
Goodwin et al. (1999, Molecular Pharmacology, vol. 56, pp. 1329-1339).*
Achira M., et al., "Comparative studies to determine the selective inhibitors for P-glycoprotein and cytochrome P4503A4," AAPS Pharmsci Electronic Resource, 1(4), E18.1-E18.6, 1999.
Ahern H. "Biochemical, reagent kits offer scientists good return on investment." The Scientist 9(15):20 (Jul. 1995).
Birren et al., << Mus musculus cloneRp23-161k8, low pass sequence sampling >> XP002382554 retrieved from EBI Database accession No. AC11090 (Online) May 27, 2004.
Baes M, et al., "A New Orphan Member of the Nuclear. Hormone Receptor Superfamily that Interacts with a Subset of Retinoic Acid Response Elements", *Mol Cell Biol.*, 14(3):1544-1552 (Mar. 1994).
Bertilsson G, et al. "Identification of a Human Nuclear. Receptor Defines a New Signalling Pathway for CYP3A Induction", *Proc. Nat'l Acad. Sci.*, USA, 95:12208-12213 (Oct. 1998).
Bertilsson, et al. "Functionally conserved xenobiotic responsive enhancer in cytochrome P450 3A7," Biochemical and Biophysical Research Communications, 280, 139-144, 2001.
Blumberg B, et al., "SXR, a Novel Steroid and Xenobiotic Sensing Nuclear Receptor", *Genes & Dev.*, 12(20):3195-3205 (1998).
Dobie K W et al. Variegated transgene expression in mouse mammary gland is determined by the transgene integration locus. *Proc. Natl. Acad. Sci. USA* 93:6659-6664 (1996). Dogra S C et al."Transcriptional activation of cytochrome P450 genes by different classes of chemical inducers." Clinical and Experimental Pharmacology and Physiology, 25: 1-9 (Jan. 1998).
Elliot J et al. Random activation of a transgene under control of a hybrid hCD2 locus control region/Ig enhancer regulatory element. *EMBO J* 14:575-584 (1995).
Felix C A, et al., "Association of *CYP3A4* Genotype with Treatment-Related Leukemia", *Proc. Nat'l Acad. Sci, USA*, 95:13176-13181 (Oct. 1998).
Finta C et al. "The human cytochrome P450 3A locus. Gene evolution by capture of downstream exons", *Gene* 260(1-2):13-23 (2000).
Garrick D et al. Repeat-induced gene silencing in mammals. *Nature Genetics* 18:56-59 (1998).
Geick A et al. "Nuclear receptor response elements mediate induction of intestinal MDR1 by rifampin." The Journal of Biological Chemistry 276(18):14581-7 [Epub](Jan. 31, 2001).

(Continued)

Primary Examiner — Peter Paras, Jr.
Assistant Examiner — David A Montanari
(74) Attorney, Agent, or Firm — Richard F. Trecartin; Morgan Lewis & Bockius LLP

(57) ABSTRACT

The invention relates to the generation of non-human transgenic animals comprising a reporter construct for producing a detectable amount of a reporter molecule operably linked to a transcriptional regulatory nucleic acid molecule from the human CYP3A4 gene located between the initiation of transcription site of the gene and a position located 13,000 nucleotides upstream from the site. The invention also relates to the use of these animals for determining the effect of a compound, particularly, but not exclusively, a xenobiotic or steroid, on the regulation of expression of the CYP3A4 gene in a human.

11 Claims, 22 Drawing Sheets

OTHER PUBLICATIONS

Gellner K et al: "Genomic Organization of the Human Cyp3a Locus: Identification of a New, Inducible Cyp3a Gene" *Pharmacogenetics*,11(2):111-121 (Mar. 2001).

Genbank accession No. D28565.

Genbank accession No. AF280107.

Genbank Accession No. D11131.

Gonzalez F J et al. "Human P450PCN1: sequence, chromosome localization, and direct evidence through cDNA expression that P450PCN1 is nifedipine oxidase." DNA (1988) 7(2): 79-86.

Goodwin B et al, "The orphan human pregnane X receptor mediates the-transcriptional activation of CYP3A4 by rifampicin through a distal enhancer module." *Molecular. Pharmacology*, 56(6):1329-1339 (Dec. 1999).

Goodwin B et al. Genbank Accession No. AF185589.

Hakkola J et al. "Xenobiotic-metabolizing cytochrome P450 enzymes in the human feto-placental unit: role in intrauterine toxicity." Critical Reviews in Toxicology, 28 (1): 35-72 (Jan. 1998).

Hamzeiy H et al. "Mutation analysis of the human CYP3A4 gene 5' regulatory region: population screening using non-radioactive SSCP". Mutation Research. 500(1-2): 103-110 (Mar. 20, 2002).

Hashimoto et al., "Gene structures of CYP3A4, an adult-specific form of cytochrome P450 I human livers, and its transcriptional control," European J. of Bioch., 218(2), 585-595, 1993.

Henikoff S Conspiracy of silence amongst repeated transgenes. *Bioessays* 20:532-535 (1998).

Herrmann J et al, "Comparative analysis of adenoviral transgene delivery via tail or portal vein into rat liver" Arch Virol, 149(8):1611-1617 (Aug. 2004).

Houdebine LM "The methods to generate transgenic animals and to control transgene expression" J Biotechnology 98:145-160 (2002).

Itoh S et al: "Isolation of a promoter region in mouse cytochrome P450 3A (Cyp3A16) gene and its transcriptional control" *Biochimica Et Biophysica ACTA*, 1350(2):155-158 (1997).

Jones S A et al. The pregnane X receptor: a promiscuous xenobiotic receptor that has diverged during evolution. *Mol. Endocrinol*. 14:27-39 (2000).

Kamataki, T., et al., << Preclinical approach for identifying drug intera tions, >> Camncer Chemother Pharmacol., 1998.

Kolars J C et al. "CYP3A gene expression in human gut epithelium." Pharmacogenetics (1994) 4: 47-259.

Kovaleva I E et al. "Transgenic yeast expressing human cytochrome P450s can serve as a tool in studies of the mechanisms of their induction by various effectors." Biochemical and Biophysical Research Communications (1996) 221(1):129-132.

Ledirac et al. "Effects of macrolide antiobiotics on CYP3A expression in human and rat hepatocytes interspecies differences in response to Troleandomycin" *Drug Metabolism and Disposition* 28(12):1391-1393 (2000).

Lehmann, J.M., et al., "The human orphan nuclear receptor PXR is activated by compounds that regulate CYP3A4 gene expression and cause drug interactions," J. of Clinical Investigation, 102(5), 1016-1023, Sep. 1, 1998.

MacGregor et al. "New molecular endpoints and methods for routine toxicity testing," *Fundamental and Applied Toxicology* 26(2):156-173 (1995).

Mangelsdorf D J, et al., "The Nuclear Receptor Superfamily: The Second Decade", *Cell*, 83(6):835-839 (Dec. 1995).

Martin D I K and Whitelaw E. The vagaries of variegating transgenes. *Bioessays* 18:919-923 (1996).

Martinez C et al., "Expression of paclitaxel-inactivating CYP3A activity in human colorectal cancer: implications for drug therapy," Br. J Cancer 87(6):681-686, (Sep. 2002).

Montoliu L, Gene transfer strategies in animal transgenesis, Cloning and Stem Cells, 4(1):39-46 (Mar. 2002).

Needleman, S.B. and Wunsch, C.D. "A general method applicable to the search for similarities in the amino acid sequence of two proteins." (1970) *J. Mol. Biol*. 48(3):443-453.

Ogg, MS., et al., "Development of an in vitro reporter gene assay to assess xenobiotic induction of the human CYP3A4 gene," Eur. J. Drug Meta. Pharmacokinet., 22(4), 311-3, Oct.-Dec. 1997.

Olsen a.K., et al., "Pig hepatocytes as an in vitro model to study the regulation of human CYP3A4: prediction of drug-drug interactions with 17 alpha-ethynylestradiol.," chem Biol. Interact., 107(1-2, 93-108), Nov. 6, 1997.

Pascussi et al. "Dexamethasone enhances constitutive androstane receptor expression in human hepatocytes : consequences on cytochrome P450 gene regulation" *Molecular Pharmacology*, 58(6):1441-1450 (2000).

Pascussi J M et al. "Evidence for the presence of a functional pregnane X receptor response element in the CYP3A7 promoter gene" Biochemical and Biophysical Research Communications 260(2):377-381. (1999).

Quattrochi et al., "CYP3A regulation: from pharmacology to nuclear receptors," *Drug Metabolism and Disposition* 29(5):615-622, May 2001.

Rebbeck T R, et al., "Modification of the Clinical Presentation, of Prostate Tumors by a Novel Genetic Variant in CYP3A4", J Nat'l Cancer Inst., 90 (16):1225-1229 (Aug. 1998).

Reid J M et al., "Rat and human liver cytochrome P-450 isoform metabolism of ecteinascidin 743 does not predict gender-dependent toxicity in humans," Clin. Cancer Res. 8(9):2952-2962, (Sep. 2002).

Ristevski S, "Making Better Transgenic Models: Conditional, Temporal, and Spatial Approaches" Molecular Biotechnology, 29:153-164 (2005).

Robertson G R et al. "Transgenic mouse models of human CYP3A4 gene regulation", Molecular Pharmacology, 64(1):42-50 (2003).

Robertson, G et al. Position-dependent variegation of globin transgene expression in mice. *Proc. Natl. Acad. Sci. USA* 92:5371-5375 (1995).

Robertson, G et al. Age dependent silencing of globin transgenes in the mouse. *Nucleic Acids Research* 24:1465-1471 (1996).

Smith, T.F. and Waterman M.S. "Comparison of biosequences" (1981) *Ad. Appl. Math*., 2:482-489.

Smith et al., "Molecular genetics of the human cytochrome P450 monooxygenase superfamily," *Xenobiotica* 28(12):1129-1165 (1998).

Smith K R, "Gene transfer in higher animals: theoretical considerations and key concepts", Journal of Biotechnology, 99(1):1-22 (Oct. 9, 2002).

Toide K et al: "Gene structure of mouse Cyp3all: Evidence for an enhancer element within its 5' flanking sequences" *Archives of Biochemistry and Biophysics*, 338(1): 43-49 (1997).

Wei et al. The nuclear receptor CAR mediates specific xenobiotic induction of drug metabolism. *Nature* 407(6806):920-923 (2000).

Xie W et al. Humanized xenobiotic response in mice expressing nuclear receptor SXR. *Nature* 406(6794):435-9 (2000).

Xie et al. "Reciprocal activation of Xenobiotic response genes by nuclear receptors SXR/PXR and CAR" *Genes and Development*, 14:3014-3023. (2000).

Yanagida A et al. "A novel cis-acting DNA element required for a high level of inducible expression of the rat P-450c gene." *Mol Cell Biol*, 10(4):1470-1475 (1990).

Yanagimoto et al., "Mouse liver cytochrome P-450 (P-450111AM1): its cDNA cloning and inducibility by dexamethasone," *Biochim. Biophys. Acta* 1130(3):329-332 (1992).

Zhang W et al, "Differential regulation of the human CYP3A4 promoter in transgenic mice and rats." *Drug Metabolism and Disposition*, 32(2): 163-167 (Feb. 2004).

\* cited by examiner

Fig 1. Human CYP3A4/lacZ transgene constructs
-3 CYP3A4/lacZ
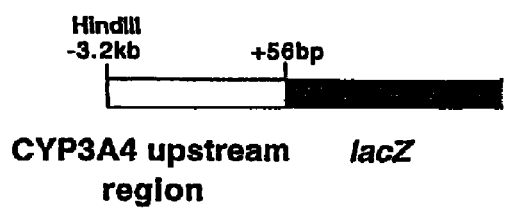
CYP3A4 upstream region     lacZ
-13 CYP3A4/lacZ
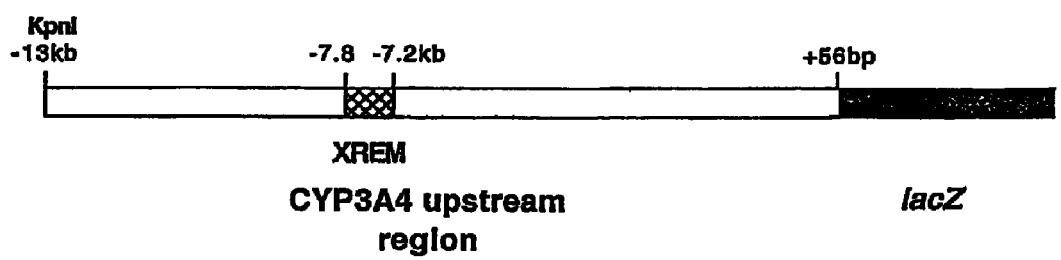
CYP3A4 upstream region     lacZ

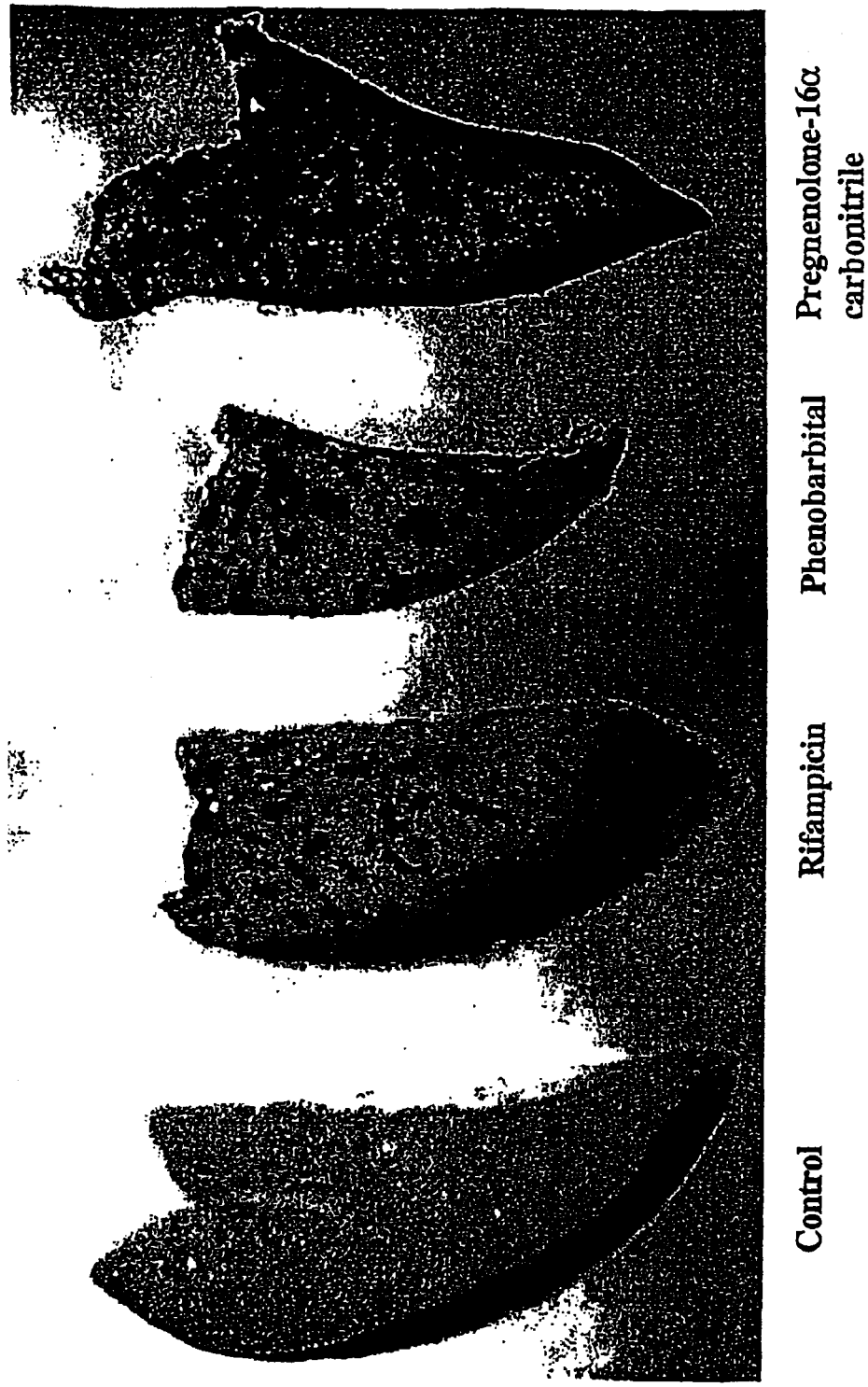
Figure 2. Xenobiotic induction of CYP3A4/lacZ transgene

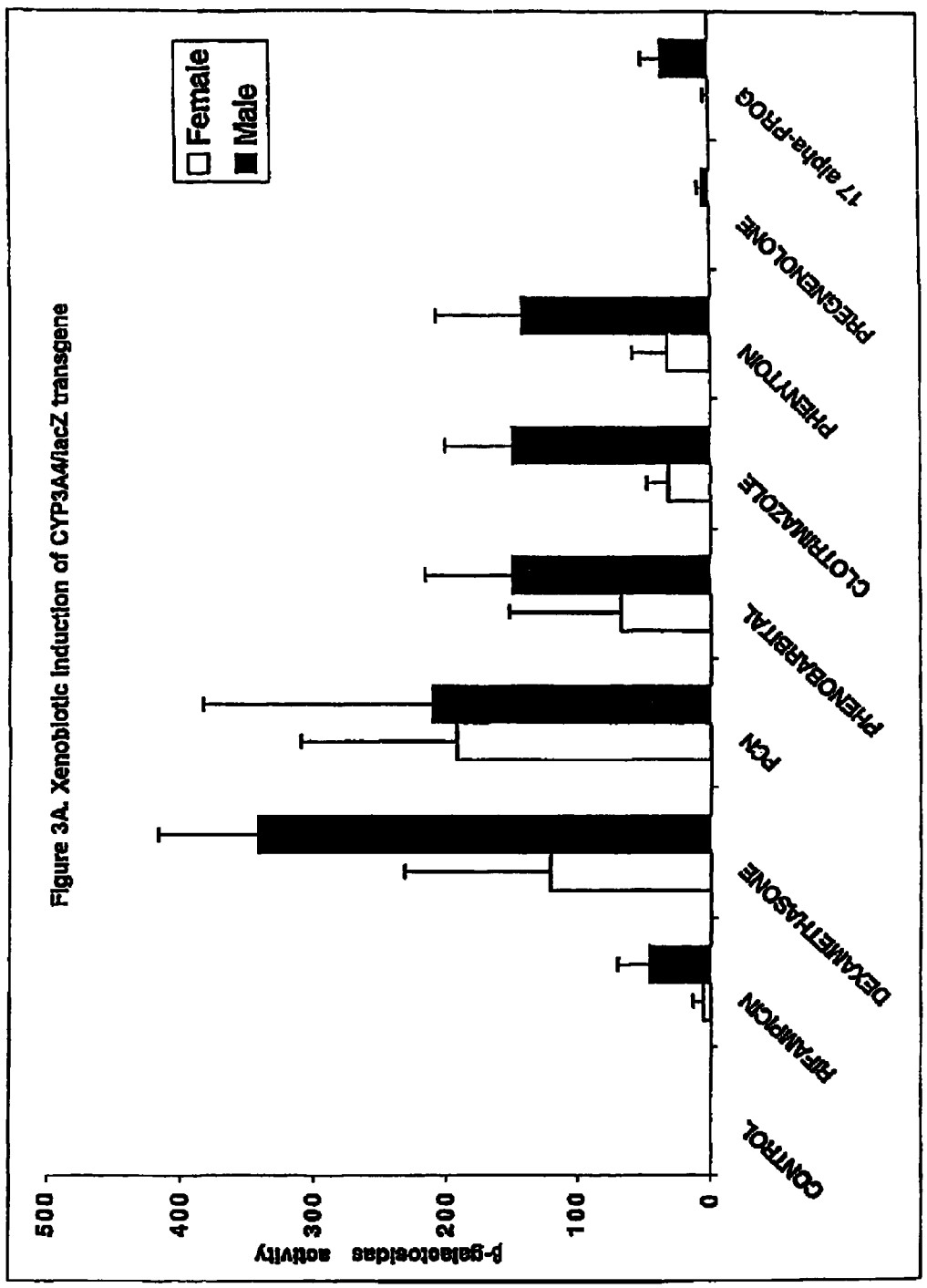

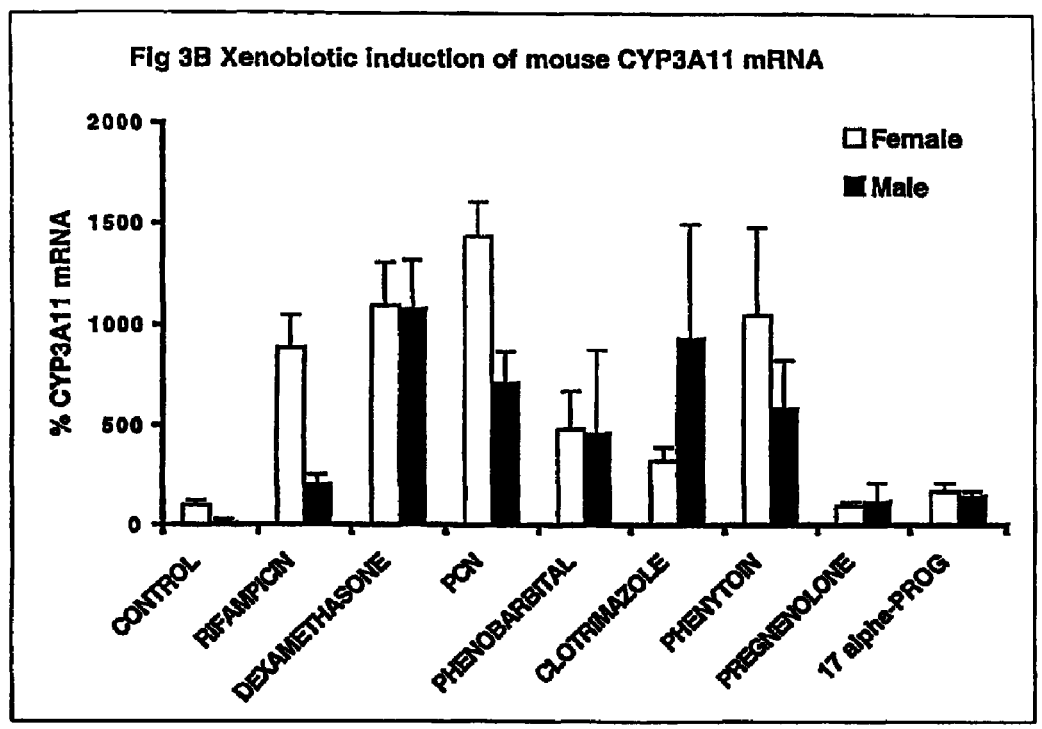

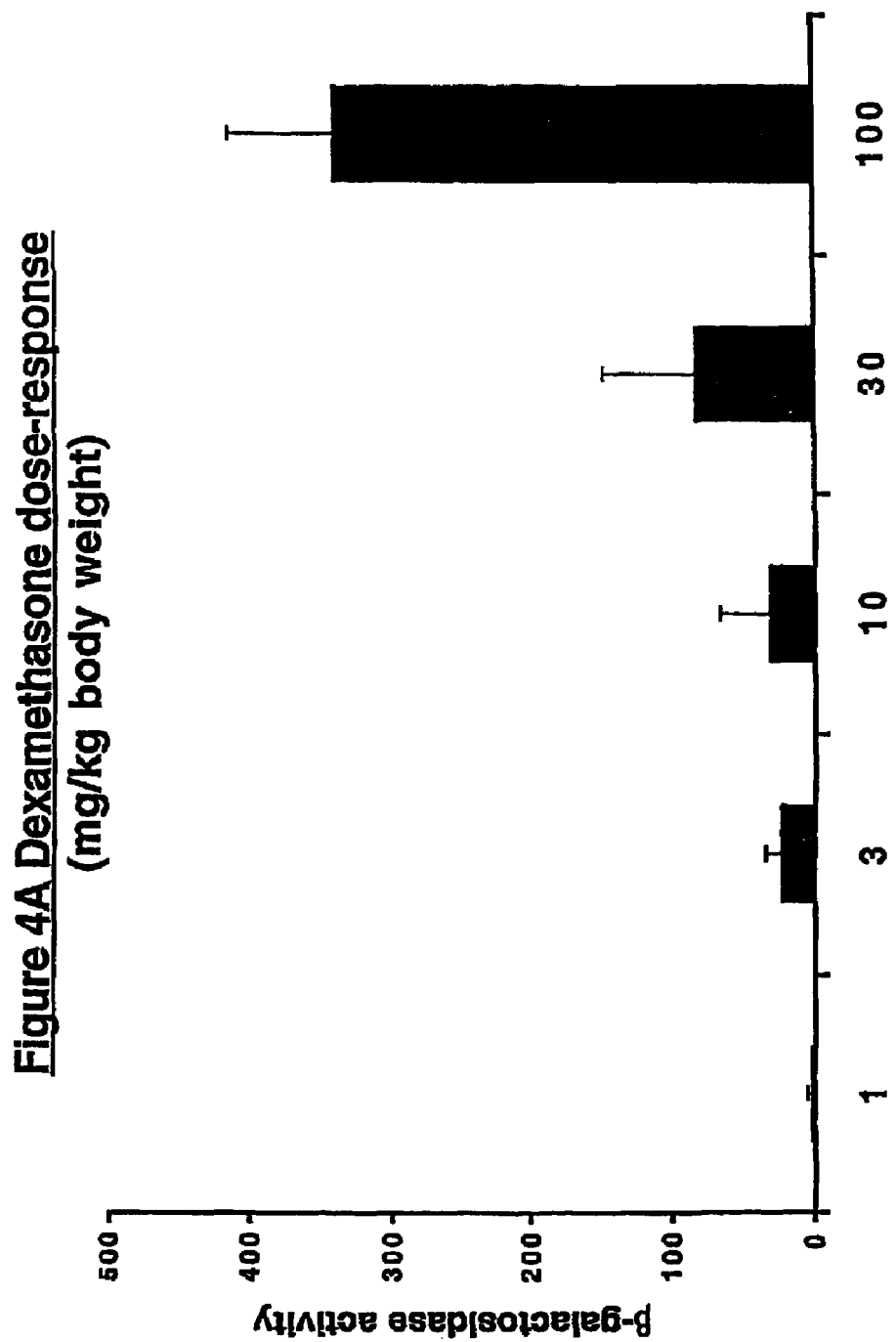

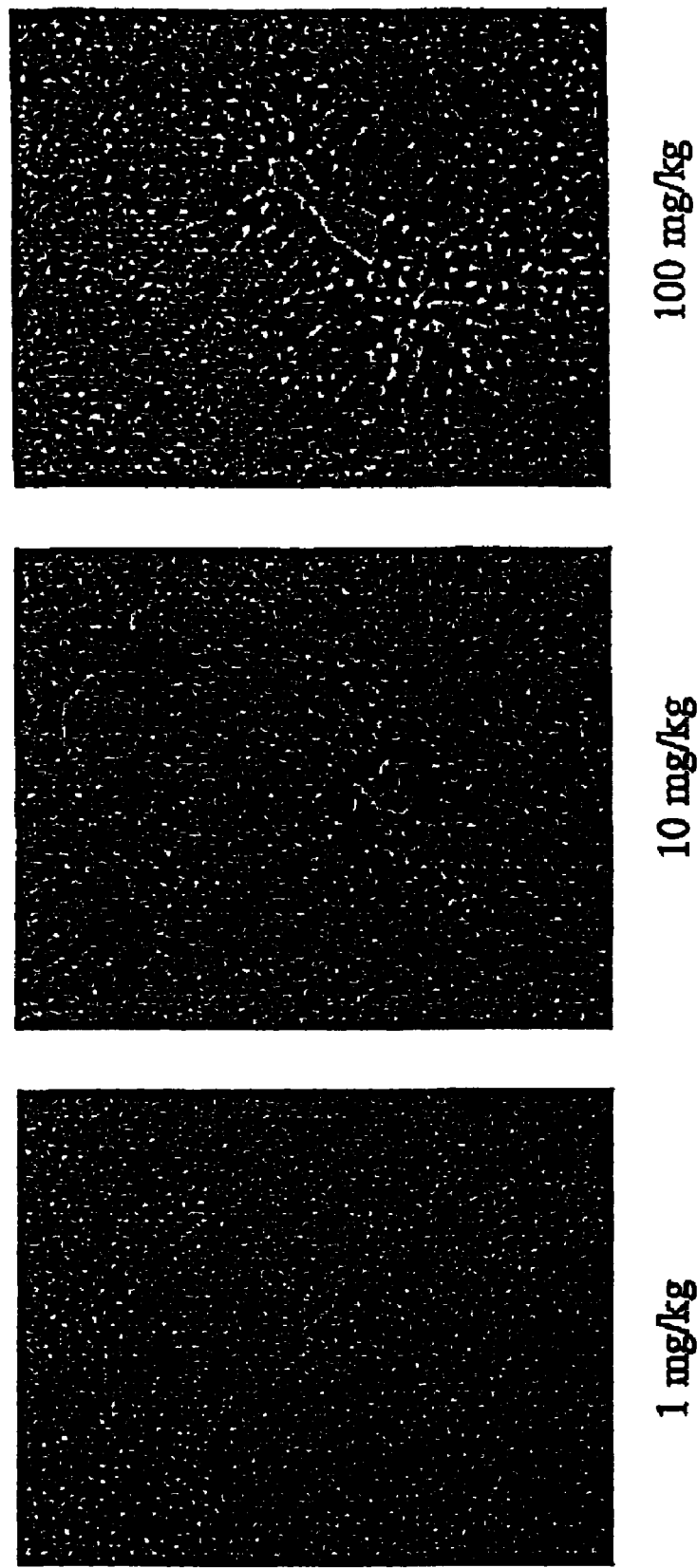
Figure 4B. Dose response of transgene expression

FIG. 5A

```
    CTGGTTCATCTCATTGGGACTGGTTGGACAAGAGGGTGCAGCCCACGGAGGGTGAGCCAAAGCAGGGTGGG
    GCGTCGCCTCACCTGGGAAGCACAAGGGGTCGTGGAATTTTCTCCCCTACCCAAGGAAAGCCATAAGGGAC
5   TGAGCCTGAGGAACTGTGCACTCTGGCCCAGATACTGCACTTTTCCCATGGTCTTTGCAACCCGCAGACCA
    GGAGATTCCCTCCGGTGCCTATGCCACCAGGGCCCTGGGTTTCAAGCACAAAACTGGGCAGCCATTTGGGC
    AGACACCGAACTAGCTGCAGGAGTTTTTTTTTTTTTTTTCCATACCCCATTGGCACCTGGAACGCCAGTGA
    GACAGAACCGTTCACTCCCCTGGAAAGGGGGCTGAAACCAGGGATCCAAGTGGTCTGGCTCGGTGGGCCCC
    ACCCCCATGGAGCCCAGCAAACAAAGATTCACTTGGCTTGAAATTCTTGCTGCCAGCACAGCAGCAGTCTG
10  AGATTGACCTGGGACCCTCGAACTTGGTTGGGTGCTGTGGGGGGCATCTTCCATTGCTGAGGCTTGAGTA
    GGTGGTTTTACCTTCGCGGTGTAAACAAAGCTGCTGGGAAGTTTGAACTGGGTGGAGCTCACCACAGCTCA
    GTAAGGCCACTGTGGCCAGACTGCCTCTCTGGATTTCTCCTCTCTGGGAAGGATATCTCTGAAAAAAAGGC
    AGCAGCCCCAGTCAGGGACTTATAGATGAAACCCCCATCTCCCTGGGACAGAGCCCCTCGGGGAAGAGGTG
    GCTTCCACCATTGTGGAAGACTGTGTGGCAATTCCTCACGGATTTAGAACTAGAGATACCATTTGACCCAG
15  CAATCCCCATTACTGGGTGTATACCCATAGGATTATAAATCATTCTACTATAAAGACACATGCACACTTATG
    TTTATTGTAACACTATTTACAATAGCAATGACCTGGAACCAATCCAAAAGCCCATCAATGATAGACTGAAT
    AAAGAAAATGTGGCACATATACACTGTGGAATACTATGCAGCCATAAAAAAGGATGAGTTCATGTCCTTTG
    CAGAGACATGGATGAAGCTGGAAACCATCATTCTCAGCAAACTAGCACAATAACAGAAAACCAAACACTGC
    ATGTTGTCACTCATAAGTGGGAGTTAAACAATGAGAACACATGGACACAGGGAGGGGAACGTCACACACTG
20  GGGCATGTCGGGGAGTGGGGGCCTACGGGAGGGATAGCATTAGCAGAAATACCTAATGTAGGTGACGGGTT
    GATGGGTGCAGCAAACCACCATGGCACATATACACCTATGTAATAAAACTGCACGTTCTGCACATGTACCC
    CAGAACTTAAAGTATAATTAATAATAATAATAATTTCTGGGCATGTAAGTAGCTGTCTTTCAGGTTCTACT
    TTGATACATATTCTGAGAGAATTAAACCTGTCAAAGAAACCTTGACTTTCAATGGCAGGCACTGGAATTGA
    CCCTAATAATGTGTTTTGGGGTAAGCCTACTCATATTCTCAACCTGTCTGCAGTAGTCGTTAGAATCTGAA
25  CTTCCTGAAGTTCATGTGCAAAGTTGAGTTAATTGTTTAATATTCAACAAGGATTATGCCAGTAAGATGGT
    AGGAAAATATTAGATATGTGTCATCACTGCTGGTATTATTTAAACTGCAACATATTTTAGCTGGCTGCTGA
    TCTCAGCCACCATGCCTGCATTTTATCTCTGTCTCGTGGTCTGCAACCTTGGAAGCTTTGAACTTAGCTCA
    TAGAATCCTGGGCATCAAGAACATGTGGTTCTAATGGCTAGATAGGGAATGAGAGTAAAAGGATTTTGCCC
    ACGGTCACGTGAGTAAACAACAGATTTGGAGGGGTCTGGACTACTGTGATGACTTCATTCTGACAATATGT
30  TCCAGTTGTCCTTTCATTTCCTCCTAATCACATGTCTGGTCTGATCTGGCTGTTTCCCACCTTCCAATTCC
    TGCCTTCTCCAATGCTCCCTTCCGTAGGTCACTCTGTGGCTCAGAGACCCTGCTTAGCAAGCGCCCAACCT
    TTCAATTATTTGTTCAGTAAAACTTGAACTCATGTCTCCCCTTCTTGATAAAAAGAAAATACGTTATGTAA
    TGTCGGGTTACTCTATAACTCTTGTCCTGTCTCTCGGCAACTACTGAACTAACTGTTTTCATATTGAGCAA
    ACGTTTATGGAAGGACTGCCAAGAGTCAGGTACTAGGCTTGGTAATATTCCCCGTTCTCTCTAGTCAAAGC
35  CAACACCAGCCAGACTTGCAGATCTAGGTCCCAAGCCCACTGCAGATCACAGGCCAGGGTCTGGTCTCCTC
    TGAGCTCCTTTGGGAGGGAAAGACAGAATTATTAACACCCATTTTGTAGATTAGGCAACTGAGGCTGAGGA
    AGTTTAAATAACTCAGACAGGGCCTGCACGTCAGTCATATTCCAAGGATCCCTACTCACTGTCTTCTCTCT
    ACAGAACGAGATGTCTCTGGAGTCCATAGAAAGCCCAGGAGCCTGGCTGGGCACGGTGGCTCCTGCCTGTA
    ATCCCAGCACTTTGGGAGGCCGAGGCAGGCAGATCACCTGAGCTCAGGAGTTCAAGACCAGCCTGGGCAAC
40  ATGGCAAAACCCCATCTCTACTAAAAATACAAAAAATTAGCTGGGCGTGGTGGTGCATGCCTCTAATCCCA
```

FIG. 5B

```
    GCTACTTGGGAGGCTGAGGCACAAGAATTGCTTGAGCCCAGGAGGCAGCAGTTGCAGTGAGCTGAGATTGT
    GCCAGTGCACTCCAGCCTGGGCAACAGAGCAAGATTCCATTTCAAAAACAAAAACAAACACAAACAAACAA
    ACAAAAATAGAAAGCCCAGGGACCACCTGCGTCAGGTTCCCAGCCACACCTTTTTCTTGTCCTCCTCTGTC
    TCTGGCATCTTCTCACAGGTTCCTAATTGTTTGTGGTTGCACAAATTCAAAATCCCAGAAAAATTACCACT
 5  TCACACCCACTCAGATGGCTATTTTTTTTTTGAAGGAAGATAACAAGTGTTGACAAGAACATGGAGAAATT
    GGAATTCTCACCCATTGCTGGTGAGAATGTAATACGGTGCTGCTGCTATGGAAAACAGCTTGGAGTTTCCT
    CAAAAAGTTCAACAGAATTTCAATGTGACCCAGCAATTCCCCTCTAAGTTATAGATCTGAGAGGATTAAAA
    ACAGTTACTAAAATACACGGACTCACATATTTCTAACAGTCCAATTCACAAGGGCCAAAAGGTGCTAATAG
    CCCACATGTCCATCGATGGATGGATAAATAAATTGTGGTCTATCCATACAATGGAATATTATTCGGCCATA
10  AATGGAATGAAGTACTGACGCATGCTACAGAATGGATGAACCGCAAAAAAAATGGATGAACACATGCTACA
    GAATGGATAGCCTCACTTTACTATGAAGTGAAGGCCAGAAACGAAGTCCATATATTGCATCATACAAAATA
    TCCAGAAGAGGGAAGCCCACAGAGACAGAATGTGCAATGGTGGATGCCAGGGTCTGGGGAGAGGGGAGAGT
    GGGGAGAAACTGCTCAACTGGTACAGGCTTTATTTTGGAATGATGGGAACATTTTGCAACTAGATAGAGGT
    AGTGATTGCAGAACACAGAATGTACTGAATTCCACTGATTTTTTTCACCTTAAAATGGTTAATTTTCAGTC
15  CTGAGATTGGATAATCATAAAAAAATGGTTAATTTTATGTTATGTGAATTTCATCCCTATACATATTTTAA
    ACCTCAGAAATATACACTAGCAGGCATGGAACAGGTCACTGTGGTGCCTGCCAAGCCCGGTGATGTTATCT
    GGGGTCCCCGGCCAGCCTTAAGCCTCTTGCTGACCGGTGGAGGGCAGAACCTTTGCCCTAAAAGTATAATA
    TCCACATGCTGGCATGATTCCTGGCCAGATGGCTTCTTTATTAGCAGTAATTGAAACTGCCTCGATACAGA
    CACTGTACCTTGCAACCAAAAAATGACTCAACAATGATAATAAGGGTTAAGCTGGGCCTTTCTCTCTTTGC
20  CAGTTAAATTATATTTATTATAGCTTGACATGAAAAACAAAGCAACTCCAACAGGTATCACAAGGGCAAAG
    GACATGAACATTTTATCAAAGAAGAAATGCAGCTGTCAAAAATACAGAAATATTCAACCTTGTTCATAATA
    AAGTGGCTGGGCTCAGTGGTTCATGCCTGTAATCCCAGTGCTTTGCAAGGCTGAGACAGGAGGATCATTTG
    AAGCCAGAAGTTCAAGACCATCCTAGGCAAGTCAGTTCAATACCAGACTTCATGTCTACAAAACATCAAAA
    AATTAGCCAGGCATGGTGATGCATGCCTGTTGTCCCAGCTACTCAGGAGGCTGAGGCAGGAGAATTGCTTG
25  AGCCTGGGAGGCTGCGGTGGCGGTGAGCCATGATTGTGCCATTGTACTCCAGCCTGGGCAATGCAGCAAGA
    CTGTCTAAATAACAAAAATAATAGTAAAGAAAAGGATTGGGATGCCATTTACTTGCGTATTCAATACACAG
    AGTTAAAAGTAATTTCTACGTTTTCTATTTTTTTATTACTAAAAAAAGCTGGACCATTCTCACAGCCTGAA
    ATGCTTCTCACTTTCCCTTCTTCTGTCCAAACACTTCTCTATGATAATGCAAACAGTCACTCCTTTAGGAA
    GACTTCACCCCAGGTAGTTCCAGATCCCCTTATCTCTGCCTTCCCAGAACTCCTGGTGTCTCTCCAGTTCC
30  CTCCGTGTGGTGAAGTACCCTACCTAGGGTTTCAGTATGGCTCTGTCTGCAAAGGTCTTGTTCACACCTTC
    CCTTATGGTTCTGTTGCCCTGTGTTGTGTCATAGCACAGGGCACAGTGGAGAACCCATTCACACTGATAGA
    GAGGGCCCCATGGTCCTGGAGATAACCATGTAACCGATCAGAATAAGGCATTGAGGGCTGGGTGTCAGGCG
    TGGGCTGCACTTGGGTGGGCAGGTCCCCTGGAAAGTCACTGGGTTTGGCAAGCTTCCTAGTAACATGTCTC
    TCTGGGGTCCCCCTTGGAACTTCATGCAAAAATGCTGGTTGCTGGTTTATTCTAGAGAGATGGTTCATTCC
35  TTTCATTTGATTATCAAAGAAACTCATGTCCCAATTAAAGGTCATAAAGCCCAGTTTGTAAACTGAGATGA
    TCTCAGCTGAATGAACTTGCTGACCCTCTGCTTTCCTCCAGCCTCTCGGTGCCCTTGAAATCATGTCGGTT
    CAAGCAGCCTCATGAGGCATTACAAAGTTTAATTATTTCAGTGATTATTAAACCTTGTCCTGTGTTGACCC
    CAGGTGAATCACAAGCTGAACTTCTGACAAGAACAAGCTATCATATTCTTTTCAATTACAGAAAAAAGTAA
    GTTAATTGATAGGATTTTTTTTGTTTAAAAAAAATGTTACTAGTTTTGAAAAGGTAATATGTGCACATGGT
40  AAACACTAAGAAGGTATAAGAGCATAATGCTTTTATACTACTAAGAATAATGTTTTCTCTAAGTTTTTTTT
```

FIG. 5C

GGTAGATGCTTTCATCAGATTAAGAAAATTCCCTGCTATTAGTTGTTGAAGGTTTTTATATCATAAATGAA
AGTTGAATATTATTATCATATATTATTAATATATTGTTATTGAACTATCAAAGCCTTTTCCTAAAACCATT
GAGATGATCTTATAACCATTCTCCTTTAACCTGTTGACGAGATCATTGGTATTTATACTATTTCTCTGTTA
ACCATTCTTGAGTCTCAGGTTTAAATTCAACTTGGTCATGGTGTGTCATCTTTGATCATTGCTGTCTGTGG
5  CTTGCTACTGTTTTGTTTAGGATTTTTGCACTGATGCTCATCAATGAGACTGGCATGCCATCTTCCTTTGC
AGTCCTGATTTTTTTCTGATTTGGATCATGTGGTTATGGCCCTCATGGAATGAGTTGGGCATGATGCCTTT
TTTTCATGTCTCTGGATTGATGGGACACTTTGGATTCTCTCCAGATGGCCCTCAATGGTCCCTGCCTCCTC
ATTGTTAGGCCCCTGGGCAAGCCCTTCTCATTTCTGGTAGGCCCAGGAACCTGTGGGGGTTTTGTTTGTTT
GTTTGTTTCTTGAGTCGGAGTCTCACTCTGTCACCCAGGCTGGAGTTGGAGTGCAATGGCCCGATCTTGGC
10 TCACTGCAACCTCCACCTCCCAGATTCAAGCAATTCTCCTGCCTCAGCCTCCTGAGTAGCTGGAATTACAG
GCACCCACCGACACACCCTGCTAATTTTTGTATTTTTAGTACAGATGGGGTTTCACAATATTGGCCAAGCT
GGTCTCGAACTCCTGATCTCATGATCTGCCCGGCTTGGCCTCCCAAAGTGTTGAGATTACAAGCATGAGCC
ACCACACCCAGTGAACCTGTGGTTTTTAGAAGCTCCCCATGCATGTGAATGCTGTGAGCATCCCAGGATGA
CAGCCACTGTGTGTTCAGCTGTTGGAACTGTGAGAAAGCACCAGTGGGACCTTCTCCAGCACCTGCCTGCT
15 GAGTTCATGGAAGAGGCTTGTTGGGGAGATGATGCCCTGGCTGACTCCTGAAGGATGGTTAGGAATGCACC
AGATGGAAGCTGGGTTGGACCCACTCTATGCTGAAGAACAGCTTGTGTGGACACAAGGAGACACGGATATG
TCATTTTTGTAGAGCCTGAGGAGTGTCCAATCACACCATTTGCTTAAAACATCATGCACACTTGGAAAAGT
GGACTGAGACCGAATGAAGAAGCTAACAGTGGCCAGATCAGAAAGGGTCTTGTGTTACTTCCTAGAGATAC
TTAGATTTTATCCTGTGGGTGATAGGAGCAGTTGGAGGGACTGAAGACAAGGAAAGAAACATGTTTCAAGA
20 TCTATGTTTTTCAAGACGCTTTTCTGGTGGCTGAGTAGGGAATTCCCTGGATAAGTCCTGCCCAGGGTCAG
GCAAAACAAGTTAGGGGGTTACTGAAATAAGGAGTATGAGAAATGGTGTAGGTTGTGCTGACGTTTTGTAA
CACATCTCATGATGATCTTCATTTCCTTCACTAATTTCCTGTTTCATTAATTCCCTTCCACGTGCTCTTCT
GAAATTTGCCTCACATTCTCTGATTTCTCTTTTACCTGTTGGTTTCATCACCTTTTACTTTTTGCTTTCCT
GGAAACACAAATGATTCTGATTGTGACATGTCAGAATTATTTGCAACATTTGCCTTTCTGCTGAAACCATG
25 AGTTCACTGAATACACAATTTAGTAAAGTGTAGGATGCACATGTCGTTTTCGTGGTCACAACCAGCTCTGT
AGCATTTTATAACTACACTGGCAGTGTGCTGGGAGGTGTAGAGAGAAATATTTATCACATGTGTGGCTGAC
ACAACCTGCCAAGTTATTTTAGGAGCCTCCTTGGAATCCCAGCAAGAATGCTACCGGCACAATTTGTAATC
ACAGCATCCTGCTCCATGCCTTGGCTTCATGGCATAGTCACTTCTGCAAGTCTCTTTCCAGCTGTCTGTTC
CCATGTCTATAAAGTATGAGTTAAATCATCCTAACACTACTCATCTTACAAAGTTTTCTTGCTGATGTTAA
30 GAGAGTTGGGAAAGAACTGTATAAACTGTGAAGTGCCATGGAGATGTTAGTGGTTACTTTATCAAGAAATA
GACACTCTAGAATGGAGTAGAAAGCCAACAGTTATGATTGAGTCCTCCTCCTCTTCTTCTTTTTATTAATT
TATAAAGAAAAGAGGTTTAATTGACTCACAGTTCCATATGGCTGGGGAGGCCTCGGGAAACTCTCAGTCAT
AGCAGGAGGCAAAGGGGAAGAAGGCACCTTCTTCACAAGGCGGCAGGAGAGAGAGAGCTCCTGTTCTTTTT
TGTCATAAAGTCTACAGAAGTGCTTATACTTCAGGACAAGGGCAGGCAGAGAGAAGGAAGGACATTGCTTC
35 ACCCCAGCCCTCACTGACGAGTTTGCTAGGGGACCTCACTTTGTCCCAGAGTAGGGCAGAACTCTGGCCAC
TACCCATTCAGAAGGCCTGGGCTGCACTGCTAGTTCCTCACTAACTCTGTGTGGCCTTGGGCAAGGTTGGG
CCTGTGTTAACAGATTATGACCCTGGGCTCTCAAGCTAGAGGATCTAAATTTGAATCCTGGCTCTGCTAAA
GCAATTAGTGATGTAAACTTTAATGGGTCAGTTAACCTTCCTGTGGCTTAGTTTGCTCATCTGTAAAATAG
GGATCATAACAGTATCAATACCACATGATTGTTGGACAGATTGAATCAGTTAATGCAGGGGAAGTACTTAG
40 CATGACACGTATTCACTATCATTTCCTGGAGTAAGAGCTGTGTGTGAGTGGGTGTGAGCATGTGTGAAACC

FIG. 5D

```
     TTTTCTCTGCAATCTCAGTTAAGAAACCAATCCAGAATTTAAAGTTCAGGGCCTAAATGGGTGGTTATCTT
     CTCCCAGTTCCATCCTATCCCACCTTTGCTCTTCCTCCCGCCCACAGGAGCTGTTGGTCCTTGATTGGGCT
     GGAAGACCTGGTGGACCCTAAGTGATCTATAAGAGGAGAATAGAGAACAGGGAATGTCTTCAAAAATCTAG
     AGGGACACAGAGGCTGAGAGGCAGGCAGTCCTGCAGGGTCTTCTGATTGGGACAAGGAGAACCTTGGTCTT
 5   CACAGGCCAATTCTGGTCAGTTTCCCCCATGGACAGATGAGGAAACAGGCCCAGGAATATCCAAGGTCTCA
     CACTTCCCATCTGTCAAGTCTTGTTGATTCTGTTGTATTCATGTCTCTCAAAGGGAGATAGAGTTTAGGGA
     AGAAAGAAGGATCAACTGTGTCTGATACCACTGGGAGCTTAAGTAAAGGGTTCTTTTACTTCATAGCATTT
     ATCCCAATTTGTAATTCAGTATTATTTGTGTGGCTGTTTGGTGTCTCTTTCTCCTATATGAGTGCTAGCTT
     CATAAGGGCAAGGATTTTGATTCTTTAATATTTAGTGCTTGCCACATGCCCTGAACACAGCAGGCATACAG
10   GCTAACCAACATACAGTGGCATGAAAGTCATGAAAGTGAGACACCTACCTCCTCCAGTGCCAAGAGAGCAT
     AACCATGCACCTGTCACTCTCCTCAACACCACCCCCAAGCATGAGGCCCAAAAGCATTAGCTAATCCCCTC
     CTCCAGCCACTAAAACTTAAAGGCCAGGTGTGGTGGCTCCCATCTGAAATCCCAGAACTTCAGGAGACAGC
     AGCAGGAGGATCACTTGAGGCCAGGAGTTTGAGATCAGCCTGGGCAACATAGCTAGGTCCCATCTGTACTA
     AAAATTAGCTGGGCGTTGTTGCATGCCTGTAGTCCCAGCTACTAAGGAGGCTGAGGTGGGAGGATCACTTG
15   AGCCCAGGAGGTGGAAACAACAGTAAGCTATAATCACAGCACTGAACTCTAGCCTGGGCAACAGAGTGACA
     CCCTGCCTCAAAACAATTTTAAAAATAAATAAGAGCAAAACTTAGATACCACGTGGTCACCCCAACATGCA
     AAATCAAGTTTTCCCCTACTGAGAAGAATGGGGACTTGACAGCTGAGTTACAGAGAGATAATCTTCTTCTT
     CTTTTTTTTTTTTTGGTTTACATCCTCAAGATCATGACTTGTGAAATTTGAATCGAATACACATGTAATTC
     CAGAGCAATGTTGCCTCCGCATACCATCAGCAATTCACTTGGCTACTGGAAGTCAGGATAAGCTTCCAGA
20   AGAGAGGTACCACTTGGGCTACCAATATAAAAGGATGAAAATATCAGAGTGATGGTGTTCTTTACAACGTT
     GAGTCCCTGGACAGCCTGTCCACTGATGCTGATATCTGAGCCTAATGCTTCTCTGAATGTTGAGATTGAAC
     TTTGATCCAATGAAACTAGAACGAGAAAGAAGATAAGTCTTTCATTGTTGATAAGGACATTATGTTTCTCA
     TACTTGTATGATTATTTTTCCTTAGCTGTACTATAATTATCTGCTTATTTGTCTCTGCTCTATGTGCTTAG
     GGTACAAAGTTGACCAAGACCAACTTTGGTTGGAAGCATAGTACTAAGAGCACAGTACTGAGAGCACAGTA
25   TTGAGAGCACAGCTTTAAAAAACATGATGAAGGCTTTAATACAGGAAATGAGCAGGGAGAGGCATGTGGT
     GGTTGGATGTATCTTCCTTGACACAGTCAGTGCAGCTCTCAGTAGTCAAGTCCCTACATGTTAGAAGATGT
     TACCTTCTGTGGAATTAAGTGGCAGAACTTGCCTTCAATTATTTTCCTTTGCAGAACAACACCAACTGCAT
     TAGTTAGGACACAGTGCTGGCTGCATTTAAGTCCCAAGCGATGATTAGTCTCTCACTGTTGGTATAGATTC
     AAACCAATCAGACCACCTCCTAAAGTTTGTAGGGCAGGTAAATCCTCATCTTAGAATAAAAATCATCTTAC
30   CAAGTATGTGTTTTAGAGGCAAGAAGAAAACATATTTGTTTCTGTAAGAGTTTTGTTTAAAAAAAATATAA
     GAAAGGCTCTCGGTTTAGGTGAGGTAATGAAGTTGTTGATAGTTATCAGATGACACTGGAATCTTTACTTC
     TCTGAACGTGTTCTGTGCATCTCTCAGTGTGGGAACATAGAGAGGGAGATCCTCCAGCAATGCCACTGATA
     TGGTCAGAAACTGCATCTTTCTTTCTCCCTGCTGAGATGAGATGGAGTCCTTTGTTCTAGAAGACCCATGG
     TGGTGCCGCTGGAGTAACCCTTGAGACAGGAACACAAATCCCAACCAATTTGTGGTTGCAGCCTTGAGTC
35   TCACTATTTCCCATAGTGATGCGTAGCAGGGAATGGCAGGTGCACCAGAGCAGGAGAGGACCTAATATCTC
     CCTTCCTGTTAGCTTTTTATAAAGTTTTATTGTGATCAGTAGCAGTTGGGAAGCTACTTGCAGTCACTGAG
     CCTCAGTTTCTACATCTGTAAACTGGGGATAGTAGCATGGCCCCTACTTAATGTGCTCAGCAAAGCCACTG
     AAAGGAGACAGAAATGTATCTAAATTACCCTGGACTTTTATCCTACCTCTCTTGGGGATTGTCACCACCTT
     CCCATGTTTGTCCTTTTTGGTTTGATGCTTGCTGTCACTTCTTTCCTTAGGTGCCTCTCTGTACGGCTCTT
40   TTATCCCAGGGATTCCAGAGTTACAGCACATGCATACCACCATCCAAGCATGTTTATTTGTCTCCTGCTTC
```

FIG. 5E

```
     ACTAGGCTGTCCCCAAGGAACATGTGGCTCCCGGCACACACCTGGCACAACACTGCACATGACATTCACCC
     ACTTGGCCTTGAATCTGACAAGGAATCTGGCATGATGTTCACCCACTCAGGCCAGGTGCCGAGCAGCCCTG
     GAGGCTTAGGGGCCAGAGGGATGGGAAAAGGTGTCTTTCTGGGGTGAGTATCAGTTTCTGCAGGAGGGCTG
     AATGTGAGAAAGAATAAAGAGAGAAGGAAGCGAACAAGCACAGCTTAAACATCGCCTATTTCTATTGAGTT
  5  TTAAGAACGCTGTGATTTTGTTTGTCATGCAATCCATTCATCAGGCCAGGCAGACACAGAACTTGGGTGTG
     AGTGACGATAATGAGCTGATATAATTTTCACACCCTCATCACTGAGATCTCTCCCATCAGGAATGGGTCAG
     GGAGCTCACAGGTGGCAGCAACTGCTATTACAGGCCTCATCTCTACCAGCTCCTGGGGCCTGCCCTCCTCC
     CATTAGAAAATCCTCCACTTGTCAAAAAGGAAGCCATTTGCTTTGAACTCCAATTCCACCCCAAGAGGCT
     GGGACCATCTTACTGGAGTCCTTGATGCTGTGTGACCTGCAGTGACCACTGCCCCATCATTGCTGGCTGAG
 10  GTGGTTGGGGTCCATCTGGCTATCTGGGCAGCTGTTCTCTTCTCTCCTTTCTCTCCTGTTTCCAGACATGC
     AGTATTTCCAGAGAGAAGGGGCCACTCTTTGGCAAAGAACCTGTCTAACTTGCTATCTATGGCAGGACCTT
     TGAAGGGTTCACAGGAAGCAGCACAAATTGATACTATTCCACCAAGCCATCAGCTCCATCTCATCCATGCC
     CTGTCTCTCCTTTAGGGGTCCCCTTGCCAACAGAATCACAGAGGACCAGCCTGAAAGTGCAGAGACAGCAG
     CTGAGGCACAGCCAAGAGCTCTGGCTGTATTAATGACCTAAGAAGTCACCAGAAAGTCAGAAGGGATGACA
 15  TGCAGAGGCCCAGCAATCTCAGCTAAGTCAACTCCACCAGCCTTTCTAGTTGCCCACTGTGTGTACAGCAC
     CCTGGTAGGGACCAGAGCCATGACAGGGAATAAGACTAGACTATGCCCTTGAGGAGCTCACCTCTGTTCAG
     GGAAACAGGCGTGGAAACACAATGGTGGTAAAGAGGAAAGAGGACAATAGGATTGCATGAAGGGATGGAA
     GGTGCCCAGGGGAGGAAATGGTTACATCTGTGTGAGGAGTTTGGTGAGGAAAGACTCTAAGAGAAGGCTCT
     GTCTGTCTGGGTTTGGAAGGATGTGTAGGAGTCTTCTAGGGGGCACAGGCACACTCCAGGCATAGGTAAAG
 20  ATCTGTAGGTGTGGCTTGTTGGGATGAATTTCAAGTATTTTGGAATGAGGACAGCCATAGAGACAAGGGCA
     AGAGAGAGGCGATTTAATAGATTTTATGCCAATGGCTCCACTTGAGTTTCTGATAAGAACCCAGAACCCTT
     GGACTCCCCAGTAACATTGATTGAGTTGTTTATGATACCTCATAGAATATGAACTCAAAGGAGGTCAGTGA
     GTGGTGTGTGTGTGATTCTTTGCCAACTTCCAAGGTGGAGAAGCCTCTTCCAACTGCAGGCAGAGCACAGG
     TGGCCCTGCTACTGGCTGCAGCTCCAGCCCTGCCTCCTTCTCTAGCATATAAACAATCCAACAGCCTCACT
 25  GAATCACTGCTGTGCAGGGCAGGAAAGCTCCATGCACATAGCCCAGCAAAGAGCAACACAG
```

FIG. 6A

```
CTGGTTCATCTCATTGGGACTGGTTGGACAAGAGGGTGCAGCCCACGGAGGGTGAGCCAAAGCAGGGTGGG
GCGTCGCCTCACCTGGGAAGCACAAGGGGTCGTGGAATTTTCTCCCCTACCCAAGGAAAGCCATAAGGGAC
TGAGCCTGAGGAACTGTGCACTCTGGCCCAGATACTGCACTTTTCCCATGGTCTTTGCAACCCGCAGACCA
GGAGATTCCCTCCGGTGCCTATGCCACCAGGGCCCTGGGTTTCAAGCACAAAACTGGGCAGCCATTTGGGC
AGACACCGAACTAGCTGCAGGAGTTTTTTTTTTTTTTTTCCATACCCCATTGGCACCTGGAACGCCAGTGA
GACAGAACCGTTCACTCCCCTGGAAAGGGGGCTGAAACCAGGGATCCAAGTGGTCTGGCTCGGTGGGCCCC
ACCCCCATGGAGCCCAGCAAACAAAGATTCACTTGGCTTGAAATTCTTGCTGCCAGCACAGCAGCAGTCTG
AGATTGACCTGGGACCCTCGAACTTGGTTGGGTGCTGTGGGGGGCATCTTCCATTGCTGAGGCTTGAGTA
GGTGGTTTTACCTTCGCGGTGTAAACAAAGCTGCTGGGAAGTTTGAACTGGGTGGAGCTCACCACAGCTCA
GTAAGGCCACTGTGGCCAGACTGCCTCTCTGGATTTCTCCTCTCTGGGAAGGATATCTCTGAAAAAAAGGC
AGCAGCCCCAGTCAGGGACTTATAGATGAAACCCCCATCTCCCTGGGACAGAGCCCCTCGGGGAAGAGGTG
GCTTCCACCATTGTGGAAGACTGTGTGGCAATTCCTCACGGATTTAGAACTAGAGATACCATTTGACCCAG
CAATCCCATTACTGGGTGTATACCCATAGGATTATAAATCATTCTACTATAAAGACACATGCACACTTATG
TTTATTGTAACACTATTTACAATAGCAATGACCTGGAACCAATCCAAAAGCCCATCAATGATAGACTGAAT
AAAGAAAATGTGGCACATATACACTGTGGAATACTATGCAGCCATAAAAAAGGATGAGTTCATGTCCTTTG
CAGAGACATGGATGAAGCTGGAAACCATCATTCTCAGCAAACTAGCACAATAACAGAAAACCAAACACTGC
ATGTTGTCACTCATAAGTGGGAGTTAAACAATGAGAACACATGGACACAGGGAGGGGAACGTCACACACTG
GGGCATGTCGGGGAGTGGGGGCCTACGGGAGGGATAGCATTAGCAGAAATACCTAATGTAGGTGACGGGTT
GATGGGTGCAGCAAACCACCATGGCACATATACACCTATGTAATAAAACTGCACGTTCTGCACATGTACCC
CAGAACTTAAAGTATAATTAATAATAATAATAATTTCTGGGCATGTAAGTAGCTGTCTTTCAGGTTCTACT
TTGATACATATTCTGAGAGAATTAAACCTGTCAAAGAAACCTTGACTTTCAATGGCAGGCACTGGAATTGA
CCCTAATAATGTGTTTTGGGGTAAGCCTACTCATATTCTCAACCTGTCTGCAGTAGTCGTTAGAATCTGAA
CTTCCTGAAGTTCATGTGCAAAGTTGAGTTAATTGTTTAATATTCAACAAGGATTATGCCAGTAAGATGGT
AGGAAAATATTAGATATGTGTCATCACTGCTGGTATTATTTAAACTGCAACATATTTTAGCTGGCTGCTGA
TCTCAGCCACCATGCCTGCATTTTATCTCTGTCTCGTGGTCTGCAACCTTGGAAGCTTTGAACTTAGCTCA
TAGAATCCTGGGCATCAAGAACATGTGGTTCTAATGGCTAGATAGGGAATGAGAGTAAAAGGATTTTGCCC
ACGGTCACGTGAGTAAACAACAGATTTGGAGGGGTCTGGACTACTGTGATGACTTCATTCTGACAATATGT
TCCAGTTGTCCTTTCATTTCCTCCTAATCACATGTCTGGTCTGATCTGGCTGTTTCCCACCTTCCAATTCC
TGCCTTCTCCAATGCTCCCTTCCGTAGGTCACTCTGTGGCTCAGAGACCCTGCTTAGCAAGCGCCCAACCT
TTCAATTATTTGTTCAGTAAAACTTGAACTCATGTCTCCCCTTCTTGATAAAAAGAAAATACGTTATGTAA
TGTCGGGTTACTCTATAACTCTTGTCCTGTCTCTCGGCAACTACTGAACTAACTGTTTTCATATTGAGCAA
ACGTTTATGGAAGGACTGCCAAGAGTCAGGTACTAGGCTTGGTAATATTCCCCGTTCTCTCTAGTCAAAGC
CAACACCAGCCAGACTTGCAGATCTAGGTCCCAAGCCCACTGCAGATCACAGGCCAGGGTCTGGTCTCCTC
TGAGCTCCTTTGGGAGGGAAAGACAGAATTATTAACACCCATTTTGTAGATTAGGCAACTGAGGCTGAGGA
AGTTTAAATAACTCAGACAGGGCCTGCACGTCAGTCATATTCCAAGGATCCCTACTCACTGTCTTCTCTCT
ACAGAACGAGATGTCTCTGGAGTCCATAGAAAGCCCAGGAGCCTGGCTGGGCACGGTGGCTCCTGCCTGTA
ATCCCAGCACTTTGGGAGGCCGAGGCAGGCAGATCACCTGAGCTCAGGAGTTCAAGACCAGCCTGGGCAAC
ATGGCAAAACCCCATCTCTACTAAAAATACAAAAAATTAGCTGGGCGTGGTGGTGCATGCCTCTAATCCCA
GCTACTTGGGAGGCTGAGGCACAAGAATTGCTTGAGCCCAGGAGGCAGCAGTTGCAGTGAGCTGAGATTGT
```

FIG. 6B

```
GCCAGTGCACTCCAGCCTGGGCAACAGAGCAAGATTCCATTTCAAAAACAAAAACAAACACAAACAAACAA
ACAAAAATAGAAAGCCCAGGGACCACCTGCGTCAGGTTCCCAGCCACACCTTTTTCTTGTCCTCCTCTGTC
TCTGGCATCTTCTCACAGGTTCCTAATTGTTTGTGGTTGCACAAATTCAAAATCCCAGAAAAATTACCACT
TCACACCCACTCAGATGGCTATTTTTTTTTTGAAGGAAGATAACAAGTGTTGACAAGAACATGGAGAAATT
GGAATTCTCACCCATTGCTGGTGAGAATGTAATACGGTGCTGCTGCTATGGAAAACAGCTTGGAGTTTCCT
CAAAAAGTTCAACAGAATTTCAATGTGACCCAGCAATTCCCCTCTAAGTTATAGATCTGAGAGGATTAAAA
ACAGTTACTAAAATACACGGACTCACATATTTCTAACAGTCCAATTCACAAGGGCCAAAAGGTGCTAATAG
CCCACATGTCCATCGATGGATGGATAAATAAATTGTGGTCTATCCATACAATGGAATATTATTCGGCCATA
AATGGAATGAAGTACTGACGCATGCTACAGAATGGATGAACCGCAAAAAAAATGGATGAACACATGCTACA
GAATGGATAGCCTCACTTTACTATGAAGTGAAGGCCAGAAACGAAGTCCATATATTGCATCATACAAAATA
TCCAGAAGAGGGAAGCCCACAGAGACAGAATGTGCAATGGTGGATGCCAGGGTCTGGGGAGAGGGGAGAGT
GGGGAGAAACTGCTCAACTGGTACAGGCTTTATTTTGGAATGATGGGAACATTTTGCAACTAGATAGAGGT
AGTGATTGCAGAACACAGAATGTACTGAATTCCACTGATTTTTTTCACCTTAAAATGGTTAATTTTCAGTC
CTGAGATTGGATAATCATAAAAAAATGGTTAATTTTATGTTATGTGAATTTCATCCCTATACATATTTTAA
ACCTCAGAAATATACACTAGCAGGCATGGAACAGGTCACTGTGGTGCCTGCCAAGCCCGGTGATGTTATCT
GGGGTCCCCGGCCAGCCTTAAGCCTCTTGCTGACCGGTGGAGGGCAGAACCTTTGCCCTAAAAGTATAATA
TCCACATGCTGGCATGATTCCTGGCCAGATGGCTTCTTTATTAGCAGTAATTGAAACTGCCTCGATACAGA
CACTGTACCTTGCAACCAAAAAATGACTCAACAATGATAATAAGGGTTAAGCTGGGCCTTTCTCTCTTTGC
CAGTTAAATTATATTTATTATAGCTTGACATGAAAAACAAAGCAACTCCAACAGGTATCACAAGGGCAAAG
GACATGAACATTTTATCAAAGAAGAAATGCAGCTGTCAAAAATACAGAAATATTCAACCTTGTTCATAATA
AAGTGGCTGGGCTCAGTGGTTCATGCCTGTAATCCCAGTGCTTTGCAAGGCTGAGACAGGAGGATCATTTG
AAGCCAGAAGTTCAAGACCATCCTAGGCAAGTCAGTTCAATACCAGACTTCATGTCTACAAAACATCAAAA
AATTAGCCAGGCATGGTGATGCATGCCTGTTGTCCCAGCTACTCAGGAGGCTGAGGCAGGAGAATTGCTTG
AGCCTGGGAGGCTGCGGTGGCGGTGAGCCATGATTGTGCCATTGTACTCCAGCCTGGGCAATGCAGCAAGA
CTGTCTAAATAACAAAAATAATAGTAAAGAAAAGGATTGGGATGCCATTTACTTGCGTATTCAATACACAG
AGTTAAAAGTAATTTCTACGTTTTCTATTTTTTTATTACTAAAAAAAGCTGGACCATTCTCACAGCCTGAA
ATGCTTCTCACTTTCCCTTCTTCTGTCCAAACACTTCTCTATGATAATGCAAACAGTCACTCCTTTAGGAA
GACTTCACCCCAGGTAGTTCCAGATCCCCTTATCTCTGCCTTCCCAGAACTCCTGGTGTCTCTCCAGTTCC
CTCCGTGTGGTGAAGTACCCTACCTAGGGTTTCAGTATGGCTCTGTCTGCAAAGGTCTTGTTCACACCTTC
CCTTATGGTTCTGTTGCCCTGTGTTGTGTCATAGCACAGGGCACAGTGGAGAACCCATTCACACTGATAGA
GAGGGCCCCATGGTCCTGGAGATAACCATGTAACCGATCAGAATAAGGCATTGAGGGCTGGGTGTCAGGCG
TGGGCTGCACTTGGGTGGGCAGGTCCCCTGGAAAGTCACTGGGTTTGGCAAGCTTCCTAGTAACATGTCTC
TCTGGGGTCCCCCTTGGAACTTCATGCAAAAATGCTGGTTGCTGGTTTATTCTAGAGAGATGGTTCATTCC
TTTCATTTGATTATCAAAGAAACTCATGTCCCAATTAAAGGTCATAAAGCCCAGTTTGTAAACTGAGATGA
TCTCAGCTGAATGAACTTGCTGACCCTCTGCTTTCCTCCAGCCTCTCGGTGCCCTTGAAATCATGTCGGTT
CAAGCAGCCTCATGAGGCATTACAAAGTTTAATTATTTCAGTGATTATTAAACCTTGTCCTGTGTTGACCC
CAGGTGAATCACAAGCTGAACTTCTGACAAGAACAAGCTATCATATTCTTTTCAATTACAGAAAAAGTAA
GTTAATTGATAGGATTTTTTTTGTTTAAAAAAAAATGTTACTAGTTTGAAAAGGTAATATGTGCACATGGT
AAACACTAAGAAGGTATAAGAGCATAATGCTTTTATACTACTAAGAATAATGTTTTCTCTAAGTTTTTTTT
GGTAGATGCTTTCATCAGATTAAGAAAATTCCCTGCTATTAGTTGTTGAAGGTTTTTATATCATAAATGAA
```

FIG. 6C

```
AGTTGAATATTATTATCATATATTATTAATATATTGTTATTGAACTATCAAAGCCTTTTCCTAAAACCATT
GAGATGATCTTATAACCATTCTCCTTTAACCTGTTGACGAGATCATTGGTATTTATACTATTTCTCTGTTA
ACCATTCTTGAGTCTCAGGTTTAAATTCAACTTGGTCATGGTGTGTCATCTTTGATCATTGCTGTCTGTGG
CTTGCTACTGTTTTGTTTAGGATTTTTTGCACTGATGCTCATCAATGAGACTGGCATGCCATCTTCCTTTGC
AGTCCTGATTTTTTTCTGATTTGGATCATGTGGTTATGGCCCTCATGGAATGAGTTGGGCATGATGCCTTT
TTTTCATGTCTCTGGATTGATGGGACACTTTGGATTCTCTCCAGATGGCCCTCAATGGTCCCTGCCTCCTC
ATTGTTAGGCCCCTGGGCAAGCCCTTCTCATTTCTGGTAGGCCCAGGAACCTGTGGGGGTTTTGTTTGTTT
GTTTGTTTCTTGAGTCGGAGTCTCACTCTGTCACCCAGGCTGGAGTTGGAGTGCAATGGCCCGATCTTGGC
TCACTGCAACCTCCACCTCCCAGATTCAAGCAATTCTCCTGCCTCAGCCTCCTGAGTAGCTGGAATTACAG
GCACCCACCGACACACCCTGCTAATTTTTGTATTTTTAGTACAGATGGGGTTTCACAATATTGGCCAAGCT
GGTCTCGAACTCCTGATCTCATGATCTGCCCGGCTTGGCCTCCCAAAGTGTTGAGATTACAAGCATGAGCC
ACCACACCCAGTGAACCTGTGGTTTTTAGAAGCTCCCCATGCATGTGAATGCTGTGAGCATCCCAGGATGA
CAGCCACTGTGTGTTCAGCTGTTGGAACTGTGAGAAAGCACCAGTGGGACCTTCTCCAGCACCTGCCTGCT
GAGTTCATGGAAGAGGCTTGTTGGGGAGATGATGCCCTGGCTGACTCCTGAAGGATGGTTAGGAATGCACC
AGATGGAAGCTGGGTTGGACCCACTCTATGCTGAAGAACAGCTTGTGTGGACACAAGGAGACACGGATATG
TCATTTTTGTAGAGCCTGAGGAGTGTCCAATCACACCATTTGCTTAAAACATCATGCACACTTGGAAAAGT
GGACTGAGACCGAATGAAGAAGCTAACAGTGGCCAGATCAGAAAGGGTCTTGTGTTACTTCCTAGAGATAC
TTAGATTTTATCCTGTGGGTGATAGGAGCAGTTGGAGGGACTGAAGACAAGGAAAGAAACATGTTTCAAGA
TCTATGTTTTTCAAGACGCTTTTCTGGTGGCTGAGTAGGGAATTCCCTGGATAAGTCCTGCCCAGGGTCAG
GCAAAACAAGTTAGGGGGTTACTGAAATAAGGAGTATGAGAAATGGTGTAGGTTGTGCTGACGTTTTGTAA
CACATCTCATGATGATCTTCATTTCCTTCACTAATTTCCTGTTTCATTAATTCCCTTCCACGTGCTCTTCT
GAAATTTGCCTCACATTCTCTGATTTCTCTTTTACCTGTTGGTTTCATCACCTTTTACTTTTTGCTTTCCT
GGAAACACAAATGATTCTGATTGTGACATGTCAGAATTATTTGCAACATTTGCCTTTCTGCTGAAACCATG
AGTTCACTGAATACACAATTTAGTAAAGTGTAGGATGCACATGTCGTTTTCGTGGTCACAACCAGCTCTGT
AGCATTTTATAACTACACTGGCAGTGTGCTGGGAGGTGTAGAGAGAAATATTTATCACATGTGTGGCTGAC
ACAACCTGCCAAGTTATTTTAGGAGCCTCCTTGGAATCCCAGCAAGAATGCTACCGGCACAATTTGTAATC
ACAGCATCCTGCTCCATGCCTTGGCTTCATGGCATAGTCACTTCTGCAAGTCTCTTTCCAGCTGTCTGTTC
CCATGTCTATAAAGTATGAGTTAAATCATCCTAACACTACTCATCTTACAAAGTTTTCTTGCTGATGTTAA
GAGAGTTGGGAAAGAACTGTATAAACTGTGAAGTGCCATGGAGATGTTAGTGGTTACTTTATCAAGAAATA
GACACTCTAGAATGGAGTAGAAAGCCAACAGTTATGATTGAGTCCTCCTCCTCTTCTTCTTTTTATTAATT
TATAAAGAAAAGAGGTTTAATTGACTCACAGTTCCATATGGCTGGGGAGGCCTCGGGAAACTCTCAGTCAT
AGCAGGAGGCAAAGGGGAAGAAGGCACCTTCTTCACAAGGCGGCAGGAGAGAGAGAGCTCCTGTTCTTTTT
TGTCATAAAGTCTACAGAAGTGCTTATACTTCAGGACAAGGGCAGGCAGAGAGAAGGAAGGACATTGCTTC
ACCCCAGCCCTCACTGACGAGTTTGCTAGGGGACCTCACTTTGTCCCAGAGTAGGGCAGAACTCTGGCCAC
TACCCATTCAGAAGGCCTGGGCTGCACTGCTAGTTCCTCACTAACTCTGTGTGGCCTTGGGCAAGGTTGGG
CCTGTGTTAACAGATTATGACCCTGGGCTCTCAAGCTAGAGGATCTAAATTTGAATCCTGGCTCTGCTAAA
GCAATTAGTGATGTAAACTTTAATGGGTCAGTTAACCTTCCTGTGGCTTAGTTTGCTCATCTGTAAAATAG
GGATCATAACAGTATCAATACCACATGATTGTTGGACAGATTGAATCAGTTAATGCAGGGGAAGTACTTAG
CATGACACGTATTCACTATCATTTCCTGGAGTAAGAGCTGTGTGTGAGTGGGTGTGAGCATGTGTGAAACC
TTTTCTCTGCAATCTCAGTTAAGAAACCAATCCAGAATTTAAAGTTCAGGGCCTAAATGGGTGGTTATCTT
```

FIG. 6D

```
CTCCCAGTTCCATCCTATCCCACCTTTGCTCTTCCTCCCGCCCACAGGAGCTGTTGGTCCTTGATTGGGCT
GGAAGACCTGGTGGACCCTAAGTGATCTATAAGAGGAGAATAGAGAACAGGGAATGTCTTCAAAAATCTAG
AGGGACACAGAGGCTGAGAGGCAGGCAGTCCTGCAGGGTCTTCTGATTGGGACAAGGAGAACCTTGGTCTT
CACAGGCCAATTCTGGTCAGTTTCCCCCATGGACAGATGAGGAAACAGGCCCAGGAATATCCAAGGTCTCA
CACTTCCCATCTGTCAAGTCTTGTTGATTCTGTTGTATTCATGTCTCTCAAAGGGAGATAGAGTTTAGGGA
AGAAAGAAGGATCAACTGTGTCTGATACCACTGGGAGCTTAAGTAAAGGGTTCTTTTACTTCATAGCATTT
ATCCCAATTTGTAATTCAGTATTATTTGTGTGGCTGTTTGGTGTCTCTTTCTCCTATATGAGTGCTAGCTT
CATAAGGGCAAGGATTTTGATTCTTTAATATTTAGTGCTTGCCACATGCCCTGAACACAGCAGGCATACAG
GCTAACCAACATACAGTGGCATGAAAGTCATGAAAGTGAGACACCTACCTCCTCCAGTGCCAAGAGAGCAT
AACCATGCACCTGTCACTCTCCTCAACACCACCCCCAAGCATGAGGCCCAAAAGCATTAGCTAATCCCCTC
CTCCAGCCACTAAAACTTAAAGGCCAGGTGTGGTGGCTCCCATCTGAAATCCCAGAACTTCAGGAGACAGC
AGCAGGAGGATCACTTGAGGCCAGGAGTTTGAGATCAGCCTGGGCAACATAGCTAGGTCCCATCTGTACTA
AAAATTAGCTGGGCGTTGTTGCATGCCTGTAGTCCCAGCTACTAAGGAGGCTGAGGTGGGAGGATCACTTG
AGCCCAGGAGGTGGAAACAACAGTAAGCTATAATCACAGCACTGAACTCTAGCCTGGGCAACAGAGTGACA
CCCTGCCTCAAAACAATTTTAAAAATAAATAAGAGCAAAACTTAGATACCACGTGGTCACCCCAACATGCA
AAATCAAGTTTTCCCCTACTGAGAAGAATGGGGACTTGACAGCTGAGTTACAGAGAGATAATCTTCTTCTT
CTTTTTTTTTTTTTGGTTTACATCCTCAAGATCATGACTTGTGAAATTTGAATCGAATACACATGTAATTC
CAGAGCAATGTTGCCTCCGCATACCATCAGCAATTCACTTGGCTACTGGAAGTCAGGAT
```

Figure 7

```
     TCTAGAGAGA TGGTTCATTC CTTTCATTTG ATTATCAAAG AAACTCATGT CCCAATTAAA
     GGTCATAAAG CCCAGTTTGT AAACTGAGAT GATCTCAGCT GAATGAACTT GCTGACCCTC
     TGCTTTCCTC CAGCCTCTCG GTGCCCTTGA AATCATGTCG GTTCAAGCAG CCTCATGAGG
  5  CATTACAAAG TTTAATTATT TCAGTGATTA TTAAACCTTG TCCTGTGTTG ACCCCAGGTG
     AATCACAAGC TGAACTTCTG ACAAGAACAA GCTATCATAT TCTTTTCAAT TACAGAAAAA
     AGTAAGTTAA TTGATAGGAT TTTTTTTGTT TAAAAAAAAT GTTACTAGTT TTTGAAAAGG
     TAATATGTTG CACATGGTAA ACACTAAGAA GGTATAAGAG CATAATGCTT TTATACTACT
     AAGAATAATG TTTTCTCTAA GTTTTTTTTG GTAGATGCTT TCATCAGATT AAGAAAATTC
 10  CCTGCTATTA GTTGTTGAAG GTTTTTATAT CATAAATGAA AGTTGAATAT TATTATCATA
     TATTATTAAT ATATTGTTAT TGAACTATCA AAGCCTTTTC CTAAAACCAT TGAGATGATC
     TTATAACCAT TCTCCTTTAA CCTGTTGACG AG
```

FIG. 8A

```
GGATCCAGTTTCAGCTTTCTACATATGGCTAGCCAGTTTTCCCAGCACCATTTATTAAATAGGGAATCCTT
TCCCCATTGCTTGTTTTTGTCAGGTTTGTCAAAGATCAGATGGTTGTAGATGTGTGGTGTTTGTTCTGAGG
CCTCTGTTCTGTTCCATTGGTCCATATCCCTGTTTTGGTACTAGTACCATGCTCTTTTGGTTACTGTAGCC
TTGTAGTATAGTTTGAAGTCAGGTAGCGTGATTCCTCCAGCTTTGCTCTTTTTGCTTAGGATTGTCTTGGG
AATGTGGGCTCTTTTTTGGTTCCATATGAAATTTAAAGTAGTTTTTTTTCCAATTCTATGAAGAAAGTCAT
TGGTAACTTGATGGGGATGGCATTGAATCTATAAATTACCTTGGGAAGTATGGCCATTTTCACGATATTGA
TTCTTCCTATCCATGAGCATGGAACATTCTTCCATTTGTTTGTGTCCTCTTTGATTTTGTTGAGCAGTGGT
TTGTAGTTCTCCTTGAAGAAGTCCTTCACCTCCCTTTAATTTGGATTACTAGATATTTTATTCTCTTAGTA
ACAATTGCAAATGGGAGTTCACTCATGATTTGGCTCTCTTTCTGTTATTGGTGTATAGGAATGCTTGTGAT
TTTTGCGCATTAATTTTGTATCCTGAGACTTTGCTGAAGTTGCTTATCAGCTTAAAAGGATTTTGGGCTGA
GACGATGGGGTTTTCTAAATATACAATCATGGCATCTGCAAACAGGAACAATTTGACTTCCTCTTTTCCTA
ATTGAATACCCTTTATTTCTTTTTCTTGCCTGATTGCCCTGGCCAGAACTTCCAATACTATGTTGAATAAG
AGTCATGAGTGAGGGCATCGTTGTCTTGTGCTGGTTTCAAAGTTTTTGCCCATTCAGTATGATTTTGGCTG
TGGTTTTGCCATAAATAGCTCTTATTATTTTGAGATACGTTCCACCAATACCTACTTTATTGAGAGTTTTT
AGCAGGAAGGGCTGTTGAATTTTGTCGAAGGCCTTTTCTACATCTATTGAGACAATTATGTGGTTTTTTAA
TCGTTGATTCTGTTTATGTGATGGATTACATTTATTAATTTGCATATGTTGAACCAGCCTTGCATCCCAGG
GATGAAGCCCACTTGATTGTAGTGGATAAGCTTTTTGATGTGCTGCTGGATTCAGTTTGCCAGTATTTTAT
TGAGGATTTTGGCATCAATGTTCATCAGGGATATTGGTCTAAAATTCTCTTTTTTTGTTGTGTCTCTGCCA
GGCTTTGGTATCAGGATGATGCAGGCCTCAGAAACTGAGTTAGGGAGGATTCCCTCATTTCTATTGATTG
GAATAGTTTCAGAAAGAATGGTACCAGCTACTCTTTGTACCTCTGGTAGAATTCAGCTGTGAATCCATCTG
GTCCTGGACTTTTTGGTTGGTAGGCTATTAATTATTGCCTCAATTTTAGGGCCTGTTATTGGTCTATTCAG
ACATTCAACTTCTTCCCGGTTTGGTCTTGGGAGGGTTTATGTGTCCAGGAATTTATCCATTTCTTCTAGAT
TTTCTAGTTTATTTGTGTAGAGGTGTTTATAGTATTGTCTGATGGTAGTTTGTATTTCTGTGAGATCGGTG
GTGATATCCCCTTTATCATTTTTATTGCATCTATTTAATTCTTCTCTCTTTTCTTCTTTATTATTCTGGC
TGGCGGTCTGTCAATTTTTTGATCTTTTCAAAAAACCAGCTCCTGGGTTTCACTGATTATTTGAAGGGTT
TTTTGTGTCTCTATTTCTTTTCAGTTCTCCTGTGATCTTAGTTATTTCTTGCCTTCTGCTAGCTTTTGAATG
TGTTTGTCTTCCTTCCTCTAGTTCTTTGAATTGTGATGTTACAGTGTTGATTTTAGATCTTTCCTGCTTTC
TCTTGTGGTCATTTAGTGCTATAAATTTCCCTCTACACATTGGTTTACATGTGTCTCAGAGATTCTGGTAT
GTTGTGTCTTTGTTCTCATTCATTTCAAGAACATCTTTACTTCTGCCTTCATTTTGTTATTTGCCCAGTAG
TCATTCAGGAGCAGGTTGTTCAGTCTTCATGTAGTTGTGTGGTTTTGAGTGAGTTTCTTAATCCTGAGTTC
TAATTTGATTGCACTGTTGTCTGAGAGACAGTTTGTTGTGATTTCCATTCTTTTACATTTACTGAGCATGC
TTTATGTCCCATTATGTGGTCAATTTTAGAATAAGTGTGATGTGATGCTGAGAAGAATGTATATTCTGTTG
ATTTGGGGTGTGGAGTTCTGTAGATGTCTATTCAGTCCACTGGGTGCAGAGCTGAGTGGACATGAACATTT
TATCAAAGAAGAAACACAGCTATCAAAAATCCAGAAATATTGAACCTTGTTAATAATAAAGTGGCTGGCCT
CTGGTTCATTCCTGTAATCTCAGTCCTTTGAAAGGCTGAGAAAGGAGGATCACTTGAGGCCACAAGTTCAA
GACCATCCTAGACAAGTCAGTTCAAGACCAGACTTCATGTCTACAAAACATCAAAAAATTAGCCAGGCATG
GTGATGCATGCCTGTCATCCCAGCTACTCAGGAGGCTGAGGCAGGAGGATTGCTTGAGCCTGGGAGATTGA
AGTGGCAGTGAGCCATGATTGTGCCATTGCACTCCAGCCTGGGCAATGCATCAAGACTCTGTCTAAACAAT
AATAATAATAATAGTAATAGTAATAATAATAATAATAAAGAAAACGGTTGGACGCCATTCCTTACTTATT
CAATACACAAAGTTAAAAGCAATTTCTACTTTCTCTATTTTTTTATTACTAAAAAAAAGCTGAACCATTCTC
ACAGCCTGAAATGCTTCTCACCTTCCCCTCTTCTATACAAACACTTCTCTGTTGATGATAATGCAGACAGT
CTCTCCTTTAGGAATACTTCACACCAGGTAGTTCCAGATCCCCTTATCTCTGCCTTCCCAGAGCTCCTGGT
GTCTCCCCAGTTCCCTCTGTGTGGTGAAGTACCCCACCTTGGGTCTCAGCATGACTCGTTCTTTGAAGGT
CTTGTTCACATTTTCCCTTATGGTTCTGTTCCCCTGTGTTGTGTCACAGCACTGGGCAGAGTGGACAACCC
ATTCACACCGATAGAGAGGGCCCCATGGTTCTGGAGATAACCATGTAACTGATCAGAATAGGGCATTGAGG
GCTGGGTGTCAGGCATGGGCTGCACTTGGGTGGGCAGGCCCCTGGAAAGTCACAGGATTTGGCAAGCTTC
CTAGTAACATCTCTCCCTGGGGTCCTCTTGGAACTTCATGCCCGATGCTGGATGCTGGTTTATTCTCGAGA
GATGGTTCATTCCAATAATCAATGAAACTCATGTCCCAACTAAAGTTCATAAACTCCAGTTTGTAAACTGA
GATAATCTCAGCTGAATGAACTTGCTGACCCTCTGCTTTCCCCAGCCTCTCAGTGCCCTTGAAATCATGT
CAGTTCAAGCAGCCCCATGAGGCATTACAATGTTTAGTTATTTCAGTGTTTATTAAACCTTGCCCTATGCT
GACCCCAGGTGAATCACAAGCTGGACTTCTGACAAGGACAAGCTATGATATTCTTTTCAATTACAGAAAAA
GTAAGTTAACTGATAGGATTTTTTAAAGATGTTACTAGTTTTGGAAAGGTAATTTGTGCACATGGTAAACA
AGAAGGTATAAGAGGGATAATGCTTTTATACTGCTGAGAATAATGTTTTCTCTAATTTTTTTTGGTAGATGC
TTTCATCAGATTAATAAAATTCACTGCTGTTAGTTGTTGAAAGGTTTTTTATATCATGAATGGGAGTTGAAT
ATTATCATGTATTATTAATATATTATTATTGAACTAGCAAAGGCTCTTCCTAAAACAATTGAGATGATCTT
ATAATCGTTCTCCTTTAATCTGTTGATGAGATCATTGGTATTTATACTTTTTCTCTGTTAACTATTCTTGA
GTCTCAGGTTTAAATTCAACTTGGTCATGGTGTATCATCTTTGAACACTCCTGTCTCTGGCTTGCTACTAT
```

FIG. 8B

```
TGTGTTCAGCATTTTTGCACTGATGCCGATGAATGAGACTGGCATGTCATCTTCCTTTGCGGTCCTGATTT
TTTTCAGATTTGGATCATGTGGCCCTCATTGAATGAGTTGGGTGTGATGCCTTCTTTTTCATGTATCTGGA
TTGATGGGACACTTTGGAGTCTCTCCAGATGGCCCTCAATGGTCCCTGCCTCCTCATTGTTAGGCTCCTAG
GCAACCCTTTCTCATTTCTGGTAGGCCCAGGAACCTGTGGGTTTTATGTTTGTTTGTTTGTTTGTTTGTTT
GTTTTTTGAGTTGGAGTCCTGCTTTGTCTCCCAGGCTGGGGTTGGAGTGCAATGGCCTGATCTCGGCCCAC
TGCAACCTCCACCTCCTGGGTTCAAGTGATTCTCCTGCCTCAGCCTTCTGTGTAGCTGGGATTACAGGCAT
CCACCACCACTCCTGGCTAATTTTTGTATTTTTAGTAGAGACGGGGTTTTACAATATAGGCCATTGTGATC
TCTTGGACAGGCTAGTCTCAAATTCCTGACCTCATGATCTGCCTGCCTCAGCCTCCCAAAGTGCTGAGATT
ACAGTTTTGTGCCTCCACACACAGTGAATCTGTGGTTTTTAAAAGCTCCTCATGCATGTGAATTCTGTGAG
CATCCCGGGATGACAGCCACTGTGTGTCCAGCTGTTAAAACTGTGAGAAAGCACCAGCGGGACCCTCTCCA
GCATTTGCTTGCTGTGGTCATGAAAGAGGCTTGTTGGGGAGATGATGCCCTGGTTGACTCCTGAAGGATGG
TTAGGAATGCACCAGATGGAAGCTGGGTTGGACCCAGTCTATGCTAAAGAACAGCTTGTGTGGACACAAGG
AGACACGAACACATCATTTTTGCAGAGCCTGGGGAGTAGCCAATCGCACCATTTGCTTAAAACACCGTGTA
CAGTTGGAGAAGTGGACTGAGACAGGCTGAAGAAGCTAACAGTGGCCAGATGAGAAAGGGTCTTGTGTTAC
TTCCTAGATATACTTAGATTTTATCCTGTGAGTGATAGGAACAGTTGCAGGGACTGAAGCCAAGGAAGCAT
GCTTTAAGATTCCATGTTTTTTGAGATGCTGTCTGGTGGCTGAGTAGGGAATTCCCTGGATAAGTACTGCC
CAGGGTAGGCAAAAGAAGCTAGGAGGTTACTGAAATAAGGAGTATGAGAAATGGTGTAGGTTTTGCTGATG
TTTTGTAACACATCTCATGACAATCTTCATTTCCTTCACCAATTTCCTGTTTCATTAATTCCCTTCCACGT
GCTCTTCTGAAATTTGCCTCATATTCTTTGATTTCTCTTTTACATGTTGGTTTCATCACCTTTTACTTTTT
GCTTTCCTGGAAACACAAATGATTCTGATTGTGACATGTCAGAATTATTTGCAACATTCCCCTTTCTGCTG
AAACATGAGCTCACTGAATACACAATTTAGTAAAGTGTAGGATGCACATGTTGTTTTCATGGTCATAACCA
GCTCTGTAGCATTTTATAACTACACTGGCAGTGTGCTGGGAGGTGTAGAGAGAAATATTTATCTCATGTGT
GGCTGACACAACCTGCCAAGTTGTTTAGGAGCCTTCTTGGAATCCCAGCAAGAACACCACTGATGCAATT
TGAAATCACAATGTCCTGCTCCATGCCCTGGCTTCATGGCTTAGTCACGTCTGAAGTCTATTTCTAACTAT
CTGTTTCCACATCTATAAAGTATGAGTTAAATCATCCTAATACTACTCATCTTACAAAGTTTTCTTGCTGA
TATTAGGAGAGTTGGGAAAGAACTGTATAAATTATGAAGTGCCATGGAGATGTTGGTGGTTACTTTATCAA
GAAATAGACACTCCAGAATAGAGTAGAAAGAAAACAGTTATGATTAAGTCCTCCTCCTCTTCTTTTTTTTT
AATTTACAAAGAAAGGTTTAATTGAGTCACAGTTCCATATGGTTGGGGAGGCTCAGAAAACTTGCAATCAT
GGCAGTTGGCAAAGTGGAAGAAGGCACCTTCTTCACAAGGTGGCAGGAGAGAGAGAGCTCCTCTTCTTTTT
TGTTGTAAAGTCTACAGAAGTGCATATACTTCAGGGCAAGGGCAGGCAGGGAGAAGAAAGGACATTGCTTC
ACCCCAGTCCTCACTGACAAGTTTGCTTTGGGACTTCATTTTGTCCCAGCATATGGGACAGAGCTCTGGCC
ACTACCCATTCAGAAGGCCTGAGCTGCATTGCTAGTTCCCCACTAACTCTGTGTGTCCTTGGGCAAGGCTG
GGCTTATGTCAAAAGATTATGACCCTGGGCTCTCCAGCTACAGAATCTACATATGAATCCTGGCTCTGCTA
GAGCAATTAGTGACGTAACCTTGGATGGGTCAGTTAACCTTCCTGTGGCTTAGTTTGCTCATCTGTAAAAT
AGGGATCATAACAACATCAATACCATGGGTTGTTAGACAGATTGAATCAGTTAATGCAGGGTAAATACTTA
GCATGACACGTATTCACTATCATTTCCTTGAGTAAAAGCTGAGTGTGAGTGGGTGTGAGAATGTGTGAAAC
CCTTTCACTGCAATCTCAGTTAAGAAACCCATCCATAATTTAAAGTTCAGGGCCTAAATGGGTGGTTATCT
TCTCCCAGTTGCATCCTATCCCACCTTTGCTCTTCTCCTGCCCGTAGGAGCTGTTGGTCTTTGATTGGGCT
GGAAGACCTGGTGGACCCTAAGTGATCTATAAGAGAATGAGAATAGAGGACAGGGAATGTCTTCAAAACTC
CTAGAGGGACACAGAGGCTGAGAGGCAGGCAGTCCTGCAGGGGTCTTCTGATTGGGACAAGGAGGACCTTG
GTCTTCATAGGCCAATTCTGGTCAATTTCCCCCATGGACAGATGAGGAAACAGATCCAGGAATATCCAAGG
TCTCACACTTCCCATCTGTCAAGTCTTGTTGATTCTGTTGTATTCATGTCTTTCAAAGAGAGAGAGAGTTT
AAGGAAAGAAAGAAGGATCAACTGTGTCTGATATCACTGGGAGCTTAAGTAAAGGGTTCTTTTACTTCATA
GCATTTTTCCCAATTTGTAATTCAGTATTATTTTTGTCACTGTTTAGTATCTCTTTGTCCTATTAGAGAGA
TAGCTTCATCAGGACAAGGATTTTGATTCTTTAATATTTAGTGCTTGCCACATGCCCTGAACACAGCAGGC
ATACAGACTAACCAACATACAGTGGCATCGAAGTGAGACACCTACCTCCTCCAGTGCCTAGAGTACATGTC
CATGGACCTGTCACTCTCCTCAACACCACCCCTAAGCATGAGGCCCGAAAGCATTGCTAATCCCCTCCTCC
AGCCACCAAAACTTAAAGGCCAGGTGTGGTGGCTCCTATCTGAAATCTCAGAACTTTAGGAGACAGCAGCA
GGAGGATCACTTGAGGCCAGGAATTTGAGACGGAGCCTGGGCAACATAGCTAGACACCATCTGTACTAAAAA
TTAGCTGGGCATGGTGGTATACCTGTAGTACCAGCTACTAAGGAGGCTGAGGTAGGAGGATCACTTGAACC
CAGGAGGTGGAAGCTACAGTGAGCTATAACCACAGCACTGAACTCCAGCCTGAGCAACAGAGTGAGACCCT
GCCTCAAAACAATTTCAAAAATAAATAAATAAAAACAAAACTTAGATACCACGTGGTCACCCCAACATGCA
AAATCAAGTTTTCCCCTACTGAGAAGAATGGGGACTTGAGAGCTGAGTTACAGAGAGATAATCTGCCTTTT
TTTTTTTTTTTTGGTTTACATCCTCAAGATCATGACCTGTGAAATTTGAATCTAATACACAAATCATTCC
AGAGCAATGTTGCTTCTGCCTACCACGAGTAATTCACTTGGCCACTGGAAGTCAGAACAAGCTTCCCAGAA
GAGAGGTACCACTTGGACTACCAATATAAAAGGATGAAAATATCGGAGTGAAGGTGTTCCTTGCATCACTG
AGTCCCTGGACAGCCTGTCCACTCATGCTGATATCTGAGCCTAATGCTTCTCTGAATGTTGAGATTTAACT
TTGATCCAATGAAACCAGACCAAGAAAGAAGAAACGTCTTTCATTGTTGATAAGGACATGATTTTTCTCAC
AATTTTATGATTATTTTTCCTTAGCTGTCCTATAATTATCTGCTTATTGTCTCTTCTCCATGTGCTTAGG
GTACAAAGTTGACCAAGACCAAGAATAATGTCTGGGAGCACAATACTGACAGCACAGCTTTAAAAACATGA
```

FIG. 8C

```
     TGAATGCTTTAATACAGGAAATGAGTAGGGGAGAGGCAAGTGGTGCTTGGGTGTTCTTCCAATGCATAGTA
     TCTTCCTTGACACAGTCAGTGCAGCTCTCAGTAGGCAAGTCCCTACATGTTAGAAGATGTTACTTTCTGTG
     GAATTAGGTGGCAGAACATGCCTTCAATTATTTTCCTTTGCAGAACAACACCAATTTCATTAGTTAGGACA
     GAGTGCTGGCTGCATTTGAATTCCAAGCAACGATTAGTCTATCACTGTTGGTATAGATTCCAACCAGTCAC
  5  ACCACCTCCTGAAGTTTGTTGGGCAGGTAAATCTTCATCTTAGAATAAAAATCATCTTAGCCAAGTAAGTG
     TTTTAGAGGAAAGAAGAAAACATAATCGTTTCCATAAGAGTTTTGTTTCTAAAAAAATAAGAAAGGCTCTT
     TGTTTAGGTGAGCTAATGAAGTTGTTGATAGTTATCAGATGACACTGGAATCTTTACTTGCCAGAATGTGT
     TCTGTGCACCTCTCGGTGTGGCAACATAGAGAGGGAGATCCTCCAGCAATGCCATTGATATGGTCAGAAAC
     TGCATCTTTCTTTCTCCCTGCTGAGATGGGGTCCTTTGTTCTAGAAAACCCAGGGGGTGCCACTGGGAGTA
 10  ACCCTTGAGACAGGAACACGAATCTCAACCAATTTCTGGTTGCAGCCTTGAGTCTTACTATTTGCCATAGT
     GATGCTTAGCAAGGAATGGCAGGTGCACCAGAGCAGCAGAGGACCTAATATCTCCCTTCCTGTTAACTTTT
     TATAATATTTTATTGTGATCAGTATCAGTTGGGAAGCTACTTGCAGTCACTGAGCCTCAGTTTCTACATCT
     GTAAACTGGGGATAGTAGCATGGCCCTATTTAATGTGCTCAGCGAAGCCACTGAAAGGAGACAGAAATGTA
     CCAGAATTCCCTGGACTTTTATCCTACTTCTCCTGGGGATTGTCACCCACCTACCCGTGTCTGTCCTTTGT
 15  TGCTTTGACGCTGTCACTTCTTTTCTTAGGTACCTCTCTGTAGGGCTCCATTATTCCAGGGATTCCAGAGT
     TACAGCACATGCATACCTCCATCCAAGCATGTTTATTTGTCTCCTGCTTCACTAGGCTGTCCCCAAGGAAC
     ATGTGGCTCCCGGCACATACCTGGCACAACACTGCACATGACATTCACCCACTTGGCCTTGAATCTGACAA
     GGAATCTGGCATGATGTTCACCTGCTGAGGCCAGGTGCCGAGCAGCCCTGGAGGCTTAGGGGCCAGAGGGA
     TGGGAAAAGGTGTCTTTCTGGGGTGAGTATCAGTTTCTGCAGGAGTGCTGAACCTGAGAAAGAATAAAGAG
 20  AGAAGGAAGTGAACAAGCACAGCTTAAACATCATCTGTTTCTACTGAGTTTTAACAACTCTGAGATTTTGT
     TTGTCATGGAATCCATTTCTCAGGCCAAGCAGACACAGAACTTGGGTGTGAGTGATGATAATGAGCTGATA
     TAATTTTCACACCCTCATCACTGAGATCTCTCCCATCAGGAATGGGTCACAGGGCTCACAGGTGGCAGCAA
     CTGTTATTACAGGCCTCATCTCTACCAGCTCCTGGCACCTGCTCTCCTCTCATTAGAAAATCCTCCACTTG
     TCAAAAAGGAAGCCATTTGCTTTGAATTCCAATTCCACCCTCAAGAGGCTGGGACCACCTCATTGGAGTCC
 25  TTGATGCTGTGTGACCTGCAGTGACCACTGCCCCATTGTTGCTGGCTGAGGTGGTTTGGGTCAACCTGGCC
     ATCTGGGCAGCTGTTCTCTTCTCTTTCTCCCCTACTGTTTCCAGACATGCAGTATTTCCAGAGAGAAG
     GGGCCACTCTTTGGCAAAGAACCTGTCTAACTTTCTATCTACGGCAGGACTTTTGAAAGCTACAGAGGAAG
     AAGCACAAATTGATGCTATTCCACTAAGCCATCAGCTCCATCTCATCCATGCCATGTCTCTTTTTTAGGGG
     TCCTCTTGCCAACAGAATCACAGAGGACAAATCTGAAAGTGCAGAGACAGCAGCTGAGGCACAGCCAAGAG
 30  CTCTGGCTGTATTAATGACCTAAGAAGATGGAGTGGTCACCAGAAAGTCAGAGGAAGTGACACACAGGGGC
     CCAGCAATCTCAGCCAAGTCAACTCCACCAGCCTTTCTGGTCCCCACTGTGTGTACAGCACCCTGATAGGG
     ACCAGAGCCATGAGAGTGAGTAAGACCAGACTATGCCCTTGAGGAGCTCACCTCTGCTAAGGGAAACAGGC
     CTGGAAACACACAATGGTGGTAAAGAGGAAAGAAGACAATAGAACTGCATGAAGGGGATGGAAAGTGCCCA
     GGGGAGGAAATGGTTACTTCTGTGTGAGGGGTTGGTGAGGAAAGACTCTAAGAGAAGGCTCTGTCTGGCT
 35  GGGTATGAAAGGATGTGTAGGAGTCTTCTAGGGGGCACAGGCACACTCCAGGCATAGGTAAAGATCTGTAG
     GCATGGCTTGTTGGGATGAGTTTCAAGTATTCTGGAATGAGGACAGCCATAGAGACAAGAGGAGAGTTAAT
     AGATTTTATGCCAATGGCTCCACTTGAGTTTGTGATAAGAACCCAGAACCCTTGGACTCCCCAGTAACATT
     GATTGAGTTGTGTATGATTCTACATAGAATATTAACTCAATGGAGGTCAGTGAGTGGTGTGTGTGTGATTA
     TTTGCCAACTGCCGAGGTGGAGAAGCCTCTTCCGACTGCAGGCAGAGCACGGGGGCCCTGCTACTGGCTGC
 40  AGCTCCAGCCCTGCCTCCTTCTCCAGCATATAAACAATCCAACAGCCTCACTGAATCACTGCTGTGCAGGG
     CAGGAAAGCTCCACACACACAGCCCAGCAAACAGCAGCA
```

FIG. 9A

```
GCCAATTAGAAGAAACACAACTACAAGGTCAGGGCATATTATTCAAACAGTAGAGACAATACAGTCAAATA
TTTGGCAGAATTACAAAATATCTCATTGGAAAAGACACGCAAGGGAAATCAACAAAAAGATATGAATCAGA
ATTCATCTGTGTCTCAAGAAAAGGTCATGCGATAAATTAAGTTCTGCTAGTGTTTCTACACTACCGTTAGC
CTCATTACCTTATTTTTTAAGTGTTAATATAGTTTTAGGTATTTTACATACATTTTTATTATTAATTACAA
CCAAAGTGCAACTTGTAATAGCAATTCCTTCACATTTTTTTTTCAAATCTTGCACCTTAAAATCCACCTC
GGGCCTCAGTTGGCCAGCTTTGGTATCTGATACTTGGACTACAGATACCACTAAGGCAAGTAGATAAAATG
TACTCTAGGACCTACAGCCCTTCTGCTAGATCCTGAAGAATGATCATTAAAACAAGCTGGTCTAGCTGGTC
AAGAGCAAAAATAAAATCAAGATGACAGAAAATTGATGCAAAAGTGAAGTAAAATAGCTAGAGAATATGAT
TGCGCCTGTCCCCTTAGCATGGATTCCCATGCTAGCCAATCTAAAATCCTCACTGTTAGAATCCTCCTGTC
AATATGATAGAATGAACAGCAAGCTCAGTGTCAGAAAACCTGTGTTGTTAACTTGGCCCTCTTTCTAGCTG
AATGTGTGTTTTGGTCAAGTTCTTTGGCATTTCAGAGACTCAGAGTAGTGAAGGAAGTGGATAAGATGAC
CTCTACATTCTCTTGCAAGCTCAAACATCTATGAATCCAGAGAGAAAAACTAGAGCATGAAATTAAGGTTA
TTTTAAAGAAATAACCTTAAAATTATTAGTATTCGAGGATCTCCAATATATTCATGGCACCACTCAAAACT
TTCCTTCTGCTCTATCCCGTCTTGGCTCAAAGTTATCTCCTTAATGAGGTCTGCCCTGACTATCCTACTTA
AAATTGTAAACTTTGCCCACCTGGTACTTCCACTCTCTTTCCCCTGCTCTGTTTTTCACCGTAATACTTTA
CTCTTTTTAACATACAAAATCACTTATTTACTGTGTTGTTATCTATCTGCCTACTCTTACCATCAAATATA
AGTTCTACCTAGGCAGGGATTTTTGTATGTTTTGCTCATGGATATATACGAAGCACTTAGAGTAATATGTG
ACATATACAGGGTACTTGATTAATACTGTTGAGTGAATGAATGAGTTTCCAATACAAATTTAAAATAAAAT
ATTTCCTAACTTAAAATTGTAAAGTCAGATCTAACCAACTGTTCATTGGTCTGCTAGCAGTGTTTCTTGTA
TATGGAAATATATTTTAAATAGATATGTCCTGTGAAATAATACTAAGTGTTCTAAAGAAATAAGTGAGTGA
ACGTTACCTCATTGAACTAACTTGACCTTGCTCCTGGGAGAGAGTTCATTTGAGATTAAACAAGTTCAAAG
TCTATGAATCATAAAACGATAAAAAAAACTAAAAGGGAAATGGTGTTTTTATAAGCTCTGCAATTCAAAAG
CCATTTCGGGTAATATTGTTATTTTTATGTCAGGAATTCCTCAGTGCTGATATCTTAGGGCAAAGGGTTTG
GTTATAAATTAAGAGAATGAGGAAATAGGTACATAGTAGGATTGTTCCAACCAAATATGTGTTGAATGTCA
AAGGAATTTCCCTGAGGAATAATCTTCAGAATATTTGCTAAGCACAGGAGAAAAATTTGGCTTATTACTTT
ATAGCCAGATTTCATTTTTAATTGAAACTTCTTTCAAGCAAATCACTTACTAGTCTATTAACAATAACAAC
ATAAACACAAGTAAACATTCGGAATATAGACATCCAGGTACTAAGCTGATTGCTTTACACTCACTGTCTTA
TTTTACAAGTAAGGAGTTTTAGTTGCAGCAAAAGAAATAAATTTTCCAATGTCAAATGACCAGAACTTAAA
CCCAATCTGTTTGGTGCTAAAGCCAATGTTCTTTACTGCAATGTTGGGTTATCTTGTTTCTAAAACTTAAA
TTTATCAGTAAAAGGCAAAATTTGCTATTATTGAGGACATTAAAATCATATTTTTGTAGACTCTGAGGACA
AATCCAACAAAAAAGTTCCAACTATTTCTTGGCAGGCATCATTGAAATTGGTATATAGCTTCCTTGGGTAT
TGACTTTGAAAAGGAAGTTGGTCACTTTAGATATATAAGTTCAGTCTGTTTGTAAAAACAAAATGAAAACA
AAACAGTTGCCTTATATGCTAAAATTATCCTAATCGTTTTCACCTTTAACAACATATACACAGAACTTG
AGGAACTTTACACGGCTCATCTTCATATTGTCAGCATCTAGCAAAGTACTTGCCACATAGTGATCAATAAA
AGTTTTAGCCAGCCTGGGCAACATAGTGACAGCCTATCTCTACAAAAAAAAATTAGCCAGGCAAGGTGGCG
CACACCTTTGGTCCCAGCTACTTGAGAGGAGGATGTGGGAGATCCTTTGAATGCAGGAGGTTGAGGCTGC
AGTGAGCTGTGATTGCGCCACTGTGCTTCAACCTTGGTGACAGAGCAAGACCCTGTCTCACACACACACAA
ATTAAGTAAAGAAAAAAAAAAGAATCAAAGAAAAAAATAATTCCCCAGCTTAAGTCCATCTTTATTTGTTT
GGATAAGCTATAAAGTGTCAAATAATGCTGTTAATGGACATTTCTCTAGCTCTCCCAAAGGAGGAATTGAG
CACATAGTATGTGCTGTATTTTATATACAGAATAAAAATAGAGACAAGATTTCTACCCTCACAGAACTTAA
ATTCTTCAGGAGAATGACACTGAAGTCCTTAATTGGACTTCTCTCTTCTGTATTATCTTCCTCAAGTGGAG
GTATATGGTGCTTAGTTATGAAAAATACCTCCAGGGCTTTGATCTTCTCAATAACTCTTTGAGGCTGATAT
GAAAACAGTAATTAGAAAAAAACCATGTATCCAACTTATATAGACAGTTGATGACCAAAGCTAGAATCCAG
TTATTTCAGCCTCCCATGTATTTTCTTATTACTTAAGGAGAATCTCTATCTCTACCTCTTTCTCTCTTCTT
CCTCTCTCACTTTTCTTAGAAACATGGGTAAGATTTTCAGAAATATGAGAAACTTATTAATAAATGAAAAA
TACTGGGAATTCTCAATGTTTCTTGTTTTAGCCAGTTAATTTTGGCCTTCATTCAATGTGAGTGTCCCTTA
ATAAGGAGCAAACTCCACTGAGAGATAGATACTAATAACCAGGATTCTGAAAATGCATTCTCATCCCCATC
TCCAAACTTTTATAAAAAATATTATAAAATAATACACTTTTAATATAGGAAATTTCTCAAATACAGAAAAA
ATTAAAGTAAACTCAGACCTAACTTTCATCACTAAAAGATAATCACTCTTGACACTTTGATATCTTTATCT
CTAATATTACACCAATTAATTTGCTTGATATAGTGAATATTATGCTATTATAATTTTCCCCTGCCTTTTGT
CCTTGCATATTAGCATAGGTATTTTCTGAGGTTATCACAAATCTGTAAGCACGTTTTATATTACTACTTT
TTTAAAGAGGATGTATAATAATTAATTCATCCATATATGTGGTTAAGTATTCAGGTCACTGCTCATTTT
TCACTGTTATAAAATAAAGCAGCAATGAATACCTTTGGCTGATATTTTTTTCTGTACTTGGAATTATTTCT
TTAAGATAGATTTCCTAAAATTGAATTACTGAGTCAAACAGACTTAAGTTTTCCTTATGTATGTTTCCTTA
TTCATTTGAATAATTTTCAACTCCTACTTGTTTATTTAACTCTTGTGAGCATGTGATAGTCTCATTTTTCA
AAATATCTTTGCTGTTGTAATTTGCATTTCTTTGTAGTTAGCATGAATATTTCAGTATGTTTCTTCTGTG
TACCAGTATACTACATACTTTTTTATATGAATTGCCTATTTGCATCTTTTGCTCGGTTCTATTAGACCTTT
```

FIG. 9B

```
         GAATTTTTTCTTATCCATTTATATAAGCTCTTTATATATTAAGAATATTAACCTATTGTGATATTTGCAAT
         AAATAGCTATATGGTTTGTTGTTGGTTTTAAATGTGAATTTATTCAATTTTCTTCATAATTTTGTTGTTTT
         TATAGATTTCTTTAAAAGTAATAAAATTATTGCCATATTATTATTTATTTTCAATGTCCATTACTAGCCCT
         TTCCAGTCATCACTTTTACTCTCATGTTCTTAATTTTTATTCATATCTTGGCTCCATTGACCATCTTTATT
    5    AGGATATTTGGGAAATAATACAATTTATACTAAACACACATCAAATCTTACCTTATTTTCTTCTTACAAAA
         ACCCTAGGAATATGCTGTTTTTGTCTTTATTTGAATGACACAGAAATCAAGGTTTTTGAGCAGTGGAGTAT
         TTCTTCAAATGACACAGAAATCAAGTCTTTTGAGCAGTGGAGTATTTCTTCAAAGCCACACAGCTAGTAAG
         TCATGAAGCTGGAATTCCAAGAGTTGCCACTTCATTTTCTTCTTTCCCTTTATCTTACTCAGTTGTCTTCT
         CTCCTCTTAATTTTGTCATTCATTTAAAAACATTTCTTGTGCTATTATGGTAGATTTATTTTAATAGGGGG
   10    CAGTGACTTACTCAGAGAGATGATTCTCTAATGGAGTTTTAAAGATCTTAGAAGTTGATAGAGGAGGCTGG
         GCGTGGTGGCTCATGCCTATAATCCCAGCACTTTGGGAGGCTGAGGTGGGTGGATCACTTGAGGCCAGAAG
         TTCAAGATCAGCCTAGTCAATGTGGTGAAACCCCATTTCTACTAAAATTACAAAAATTAGCCTGGTGTGCT
         GGTGCACTCCCATAATCCCAGCTACTCAGGAGGCTGAGGCATGAGAATTGCTGGAACCCAGGAGGCGGAGG
         TTGCAGTGCGCCTGGATTATTAACACTACACTCCAGCCTGGGAGACAGAGTAATACTCCATCTCAATAAAA
   15    AGAAGTTGATAAGGGAGATAGTTCATGGCAACGGATCTTTGAAGGCACGCTAATGATAACTTAGGCATTTA
         GCCTACTAGTGTAATTTCCATAAATCTGCCTCTGATGTCATACTCTCAGCACCTAATATTTCTACAAACA
         TTTATTGAAACTTTATTTTGTATAAGTCTCTGTCCAGTTTGAATATTTAAAAAATTCATAATCATATGAAA
         CATTAATAATAAATACAAATGAGAGATGCCGATACTGAAAAGTAGGATTGCGGAGTGGTAGAAAATATTT
         CTGGCTGTAGTAGATGGGGAAGTGTTCAAAGAGGAGTATAATTCAGGTTTCCATTTGCCATCGACTTATCA
   20    CATGGCTAACTCACTAAGCGACTTAATTAAAATTAAATTAATTTATCATCATCTGATCACCATTTCACACA
         ACTCATGTCTGTTGCTGTATTGGCTAAATGATGGCAAGACAAACGACCTCTGAAAATGATCCTATTGACCT
         TCGGAATCTGGATTTTTTTTTTCAATGCAGGTGTCATAGAAGCAATCTGATGTAATCCAACATGAGTTCAA
         GCACAGTCATTTAATATCCCCTATCAAGTACAGTCATTTAATATCCCCTATCATCACATGTCCTTCATCA
         TAAAAATCATTACATGTGAAAGGGTGGAGAGTGTGTGGATCCCTTATTATTGTGTTATTGTAACACAATAA
   25    CAATATTGTGTTATTATTGTTAACACAAGTGAGTCATATGTCTTGCTCTTTGGACTGAGTGGAAACTTGTA
         TTCTTTCTCTGCCTCAGGTCAATTAACTTCATTGAGGTGAGTTGCATTCCTTCTTAAGCATGTTGAACCT
         TCAATCTGGACTCAGATGGGCTAAATAGAGGAGCTAGGAAAAATACAGAAAATAAATTATTAGAGAGATCA
         GAGAAAGATACATAAGATTTACAATAAAAGAATTATGAGAAAAACATCCAAAAGAATTAAAAACCATAGGA
         GAAGGAAAAATAGGTGAACAGCTTTTTAATTTCTATAAATGTGTTGTTAATACTCATAATAAAGGACTCAG
   30    AGCTGGGATATGAGAATAATAGGTCAAACGTATATGGATACATAGATGTGACTACATACATGAGTTGCAAA
         GAATGCTAAGGAGGGCAAAAAGAGATTGAGAAGAGGGCATTATTACTAATATATAGCAATGTTGAATGTTT
         AGGGTGTTTCAGGCACTGTACAAATCTTTTAAATACACAAATCACTTAATCTTGCCATAACATTAGAAGAT
         ACTATCTACTCTTTACCAAAAAGGTAACTGTGGGATAGCAGAGTTAAGTAACCCGTTCAAACCTATGCATA
         ATAATCAGCAGAGATGGTCCTTATCTAAGTTTTTCTGCCTTTGAAGTCCAAATAGTTTAATGCAGCCAGGT
   35    ACTAAAGAAGAAAACTTTTGTAAATTAGTTTAGTTTAATGATTTACATGTGGAAAAGCACAGAGTGAAAAG
         CACATATCATCTGAGAAGCCCAGTGAGTTTGGCTGAAATGGAGTGAACATGTACATGTTGAGGGTGAGGAA
         GATGATTAGAGAGAAGTGATGTGTTGTGGTTCTTAAAAGCTAAGAGGAAACTGTTAGATATGATATAGTCT
         GTGGCAGGGAGCCATTGCAGGTTTTCCAAGATGGACTCATAAGGAGAAAACACTTCGTGGGACTGGAAAAG
         GCAGTGAAGTGGTGTGTCCTATGATAATGTACTACAGTGTAGGATAGTGGTTAAGAGTACAGTTATGAGAG
   40    AGGGACTACTGGTTAGCACCTTACCTGCTGTGTGACTGGGCAAATAATGCAAACCTCAGTGTCTTTTATTG
         TAATATGGGAGTAACAAAAATAGTAACTACTTCATAGGATTCTTGTAAAGATTAAATGACTTAATTTCTTT
         GAAGTGCTTGGCAGTTCCTGATAAATGACCAGTAGTTAATAAATGTTAGTTGTTATTATTATCATTATATA
         TTATTACTCCCATAGATACATATAGAACAGACTGCAGCAGAGAGGCAAATCTTTAATGTTGTCAGAGTATA
         GACAAGTTGGTGAAATGGCTACATGAGAGCGGAGGACAAGAAGGTGCAGATTGTGGCAGTCACTTCAAATG
   45    GAAATATCACCGCTTGAATGAAGGTATATGAGTGTCAACTTGCAAGGGGACCAGGTAGGTTTCATCAGAAA
         TTAAGGAAGCTTAAGGAGGAACAGCCAAGTTCAGCTTGACAGAAGTGGTGGTGGCACAAATGCAAGACTGGT
         GTCTTTCAAGAAACCAAGGACTGTTGAAAGTAGCAAGAGCTAGTTTGTTTTAGGTCCATCATGTTTTATAT
         TCACACTTTCATGTCAGTGGAGCAAAGAAATGGAATACAATATAATAGAATGGTAGAATCTTATTTTTAAA
         ATCTGTGTTATTCTGATCTTTAACTTACTTATATCTTTGATAGAGATCTTTACCTGATGCTCAAGATTGTA
   50    GAAATAGTATAATCAACATAACAGTATAGCACTGTATTTATATCCTGCACTGTTTAGGGAGGGTTTAAGGC
         CATTCAAAAGGATACATAAAATACAACAAGATTACATAAATGAAAGGTGAGATAAAGCAACAAAGCAAAAC
         AAAAGTGAAAACAGAGATCATAGGCACAAATAAGATTAAAAACGCATGTAATGAAGATGAAAGCTTTTACA
         TTTACCCCAGATGGACCACAGGGTTGTTGTTAAGCCTTTAAACAGTGAACAATGCTGTACACTTGCATATG
         CAATTAGAACATGTGGAAAAAATAGTGGCCTGTTAGAAGCCTAATTAACAATTTGTGAAAAAAAAAAAAAA
   55    AAAAAAAAAAAGAGGCCGAGCTGTAGCTCACGCCTGTAATCCCTGCACTTTGGGAGGCCGAGGCGGGCGGA
         TCACGAGGTCAGGAGATCAAGACCATCCTGGCTAACACAGTGAAACCCAGTCTCTACGAAAAATACAAAAA.
         ATTAGCCGGGCGTGGTGGCGGGAGCCTGTAGTCCCAGCTACCTGGGAGGCTGAGGCAGGAGAATGGTGTGA
         ACCCGGGAGGCGGAGCTTGCAGTGAGCCGAGATCCTGCCACTGCACTCCAGCCTGGGCGACAAAGCAAGAC
         TCCGTCTCAAAAAAGAAAAAAGAAAGAAAAACAAAAGAAAACTTCATTGTATTGTAAGGCCAAGAACAAAA
   60    TATATCAAGATAAGGAAAATTTGTAGTCAAGAATAGAAAAAAATTTATGGCTTTGAAGTATGAGTTATTTAA
```

FIG. 9C

```
AGAAAGTGGAAACATCCTCAGACTATGCAGTAAAAAACAAAGTGATTTTCTTCTTCTAAACTTATGCAATA
AACTGATAGGTAATATGTGAAAGTCATAGAATGTAGACTAGAGGATACAACAAACCTATTTCCTCTATGTT
CATAAGAAGTAAGAAAAGCTCTGATGTGAGTTAGCATTGCTTTACAATTTTGAATTGTGCAGATTGCACGT
ACTTTTCCTCAGTTTGAAGTAAATAGTGGACAGGAAAAAATATTAAATGTTGGCAGTAAATATGGAAGGAA
ATTACAACTAATGTAATATGCTAAAACATGCTATGTTTATTTTACTAATTTGAATTAAAATGTAAGAATTT
AAAATGCCCTGGAAAAACACGGGCATTGATCTGACGTCTGAAGTTTTAAAATATTACACACTTTGAAATAG
CATTTGTACCTTGAAATACCTGTCTCTATATATTTTTAAAACTTCCTTTTTCTTTCATTCCATTTATCAT
CAAATAAAGGATGAACAGATGTAACTCAGAAACTGTCAAGCATGCTGAAGAAAGACCACTGCAGAAAAATT
TCTCCTAGCCTTTTCAAAGGTGTTAGGAAGCAGAAAGGTGATACAGAATTGGAGAGGTCGGAGTTTTTGTA
TTAACTGTATTAAATGCGAATCCCGAGAAAATTTCCCTTAACTACGTCCTGTAGTTATATGGATATGAAGA
CTTATGTGAACTTTGAAAGACGTGTCTACATAAGTTGAAATGTCCCCAATGATTCAGCTGATGCGCGTTTC
TCTACTTGCCCTTTCTAGAGAGGTGCAACGGAAGCCAGAACATTCCTCCTGGAAATTCAACCTGTTTCGCA
GTTTCTCGAGGAATCAGCATTCAGTCAATCCGGGCCGGGAGCAGTCATCTGTGGTGAGGCTGATTGGCTGG
GCAGGAACAGCGCCGGGCGTGGGCTGAGCACAGCCGCTTCGCTCTCTTTGCCACAGGAAGCCTGAGCTCA
TTCGAGTAGCGGCTCTTCCAAGCTCAAAGAAGCAGAGGCCGCTGTTCGTTTCCTTTAGGTCTTTCCACTAA
AGTCGGAGTATCTTCTTCCAAAATTTCACGTCTTGGTGGCCGTTCAAGGAGCGCGAGGTAGGGGCACGCA
AAGCTGGGAGCTACTATGGGACAGTTCCCAAGTGTCAGGCTTTCAGATTTCCTGAACTTGGTCTTCACGGG
AGAAGGGCTTCTTGAGGCGTGGATAGTGTGAAGTCCTCTGGCAAGTCCATGGGGACCAAGTGGGGTTAGAT
CTAGACTCAGGAGCTCCTGGAGCAGCGCCCAAACCGTAGTGGCACTGGACCATGTTGCCCGGAGCGCGCAC
AGCCCGCGCGGTGCGGGGACCTGCTCTCTGAGCCCGCGGCGGTGGGTGGGAGGAAGCATCGTCCGCGGCG
ACTGGAACCGGGAGGGAGAATCGCACTGGCGGCGGGCAAAGTCCAGAACGCGCTGCCAGACCCCCAACTCT
GCCTTCGTGGAGATGCTGGAGACCCCGCGCACAGGAAAGCCCCTGCAGTGCCCATCGCGGCCAGAGCAGCT
GGGGCATCAACGGCGGGCGCTCCCTCTTACTGCTCTCTGGCTTCGACGGGGACTAGAGGTTAGTCTCACC
TCCAGCGCGCCTGAGGCTCATGCATTTGGCTAATGAGCTGCGGTTTCTCTTCAGGTCGGAATGGATCTTGA
AGGGGACCGCAATGGAGGAGCAAAGAAGAAGAACTTTTTTAAACTGAACAATAAAAGGTAACTAGCTTGTT
TCATTTTCATAGTTTACATAGTTGCGAGATTTGAGTAATTTATTTCTAGCCTCCAGCTCTGAAATAAATGA
CATGTTGTTGTTTTTAATTATTTTTAAGAAACGCAAGCTAGCCTTTG
```

TRANSGENIC ANIMALS FOR ANALYZING CYP3A4 CYTOCHROME P450 GENE REGULATION

CROSS-REFERENCE TO RELATED APPLICATIONS

This application is a continuation of U.S. patent application Ser. No. 10/415,607 filed Nov. 20, 2003, now U.S. Pat. No. 7,531,712 which is a US National Stage application under 35 USC 371 of international application number PCT/AU01/01407 filed Nov. 1, 2001, which claims the benefit of priority to Australian Patent Application Nos: PR 4901, filed May 10, 2001 and PR 1161 filed Nov. 1, 2000; each of which is hereby incorporated by reference in its entirety.

TECHNICAL FIELD OF THE INVENTION

The invention relates to the generation of a transgenic animal and to the use of the animal for determining the effect of a compound, particularly, but not exclusively, a xenobiotic or steroid, on the regulation of expression of a P450 gene in a human.

BACKGROUND OF THE INVENTION

Many endogenous and exogenous compounds are observed to have a therapeutic effect in drug development trials in vitro. However, the intended therapeutic effect is often not realised in clinical practice, for example, when compounds are co-administered, because certain compounds induce the expression of the CYP3A4 gene. This induction generates CYP3A4 cytochrome P450 molecules which metabolise compounds before the intended therapeutic effect of each compound can be realised. Accordingly, induction of expression of the CYP3A4 gene interferes with intended dosage, leading to therapeutic failure or sub-optimal treatment.

Induction of CYP3A4 gene expression is a significant problem for drug development because time, resources and expense are wasted in the development of candidate drugs for therapy of particular disease conditions which will ultimately fail or perform sub-optimally in clinical practice.

It would be advantageous to have an animal model for use in drug development trials from which, at an early stage of drug development, one could determine whether a candidate drug would be likely to achieve an intended therapeutic effect in a human.

Such an animal model would not be useful unless at least some of the aspects of the regulation of CYP3A4 gene expression in the human, especially tissue specific expression, are reproduced. This is because in the human, the CYP3A4 gene is expressed in specific tissues, including liver and small intestine, which many compounds inevitably come into contact with when administered for the purpose of therapy. Accordingly, one would be unable to determine whether the bio-availability of a candidate drug would be sufficient for achieving an intended therapeutic effect in clinical practice in a model which does not reproduce the constitutive and xenobiotic induced tissue specific expression of the CYP3A4 gene that is observed in the human.

WO99/61622 and Goodwin et al. 1999 disclose a nucleic acid molecule located 8 kb upstream from the initiation of transcription site of the CYP3A4 gene which regulates transcription of the CYP3A4 gene in response to xenobiotic compounds. These documents do not disclose elements for regulating the constitutive and xenobiotic inducible tissue specific and developmental expression of the CYP3A4 gene observed in a human.

There is a need for an animal model which reproduces at least some aspects of the expression of the CYP3A4 gene in a human, for determining whether a compound, for example, one identified in a drug development trial, would be likely to induce CYP3A4, and hence cause drug-drug interactions, or auto-induction of the metabolism of the drug under study.

DESCRIPTION OF THE INVENTION

The invention seeks to address the above identified need and in a first aspect provides a non-human mammal comprising:

(a) a regulatory nucleic acid molecule which is capable of regulating transcription of the human CYP3A4 gene and which comprises a nucleotide sequence that is identical to a sequence of the human CYP3A4 gene located between the initiation of transcription site of the gene and a position located at least 13,000 nucleotides upstream from the site; and (b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

As described herein, the inventors have found that the incorporation of a region of the human CYP3A4 gene that is located between the initiation of transcription site of the gene and a position 13,000 nucleotides upstream of the initiation of transcription site into an animal model provides the animal with sufficient genetic information for reproducing the constitutive and xenobiotic induced tissue specific expression of the CYP3A4 gene that is observed in humans. More specifically, the inventors have generated animal models which contain a transgene comprising this region and have observed that these models provide constitutive and xenobiotic inducible expression of a transgene in a tissue pattern which reproduces the tissue specific expression of CYP3A4 which is observed in a human. Importantly, the level of constitutive expression is sufficient to allow one to observe the effect on the regulation of tissue specific transgene expression, of administration of a compound, for example, a xenobiotic or steroid, to the animal.

Further, the inventors have observed that the animal models described herein also reproduce aspects of the constitutive and xenobiotic inducible developmental expression of the CYP3A4 gene that is observed in humans.

These findings are unanticipated because prior to the invention, there was no suggestion that the genetic information required for simulating the constitutive and xenobiotic induced tissue specific or developmental expression of the CYP3A4 gene that is observed in a human would be contained in the region of the human CYP3A4 gene between the initiation of transcription site of the gene and a position 13,000 nucleotides upstream of the initiation of transcription site.

Further, prior to the invention, differences in the induction profile of the mouse CYP3A11 and the human CYP3A4 gene had been observed, and differences had also been observed in the ligand binding profile of mouse transcription factors, especially PXR and CAR, and human PXR and CAR. Accordingly, there was no suggestion that a non-human animal would have factors sufficient for interacting with a region of the CYP3A4 gene for reproducing the constitutive and xenobiotic induced tissue specific or developmental expression of CYP3A4 observed in a human.

Further, prior to the invention, mechanisms associated with transgene integration had been observed, such as gene silencing and mosaic transgene expression which limited the extent to which an a transcriptional enhancer element incorporated into a trangenic model could reproduce regulation of gene expression observed in a human. Accordingly, there was no suggestion that a region of the human CYP3A4 gene would be capable of reproducing the regulation of expression of the CYP3A4 gene that is observed in a human. However, as described herein, the inventors have shown in 2 separate founder lines that the expression of the transgene reproduces aspects of CYP3A4 gene expression that are observed in humans.

Thus in a second aspect, the invention provides a non human mammal comprising:

(a) a regulatory nucleic acid molecule comprising a nucleotide sequence that is identical to the nucleotide sequence of the human CYP3A4 gene that extends about 13,000 nucleotides upstream from the initiation of transcription site of the gene; and (b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

In one embodiment, the regulatory nucleic acid molecule comprises the sequence shown in SEQ ID NO:1.

Further, as described herein, the inventors have generated transgenic animals which contain a region of the human CYP3A4 gene between the initiation of transcription site and a position about 3,200 nucleotides upstream of the initiation transcription site and observed that the transgene is not constitutively expressed or inducible by xenobiotics in these animals. Accordingly, the inventors have found that the genetic information required for reproducing the constitutive and xenobiotic induced tissue specific and developmental expression of CYP3A4 observed in a human is contained in the region of the human CYP3A4 gene between the position located about 3,200 nucleotides upstream of the initiation of transcription site of the gene and a position 13,000 nucleotides upstream of the initiation of transcription site.

Thus, in a third aspect, the invention provides a non-human mammal comprising:

(a) a regulatory nucleic acid molecule comprising a nucleotide sequence that is identical to the sequence of the human CYP3A4 gene that extends about 8,000 nucleotides upstream from a position about 3,000 nucleotides upstream from the initiation of transcription site of the gene; and (b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

In one embodiment, the regulatory nucleic acid molecule comprises the sequence shown in SEQ ID NO:2, In a fourth aspect, the invention provides a non-human mammal comprising:

(a) a regulatory nucleic acid molecule which is capable of regulating transcription of the human CYP3A4 gene and which comprises a nucleotide sequence that is identical to the sequence of the human CYP3A4 gene that extends about 600 nucleotides upstream from a position about 7,200 nucleotides upstream of the initiation of transcription site of the gene; and (b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

In one embodiment, the regulatory nucleic acid molecule comprises the sequence shown in SEQ ID NO:3.

In another embodiment, the regulatory nucleic acid molecule has the sequence of any one of the following fragments of the CYP3A4 gene:

(i) a fragment consisting of from nucleotide positions −13,000 to +53;

(ii) a fragment consisting of from nucleotide positions −13,000 to −12,700 contiguous with −8000 to +53;

(iii) a fragment consisting of from nucleotide positions −13,000 to −5,100 contiguous with −1,200 to +53;

(v) a fragment consisting of from nucleotide positions −7,800 to −6,000 contiguous with −362 to +53;

(vi) a fragment consisting of from nucleotide positions −7,500 to −6,000 contiguous with −362 to +53;

A regulatory nucleic acid molecule which has the sequence of a fragment consisting of from nucleotide positions −7836 to −7207 contiguous with −362 to +53 is particularly preferred, as this construct contains the minimal sequences necessary for regulating transcription of the human CYP3A4 gene, more specifically, an element responsive to xenobiotics (the "Xenobiotic Response element Module" or "XREM") and the proximal promoter of the CYP3A4 gene.

The regulatory nucleic acid molecule of the invention typically contains at least one enhancer capable of regulating transcription of a human CYP3A4 gene when contacted with a nuclear receptor. Examples of such enhancers are those capable of regulating transcription of a human CYP3A4 gene when contacted with a nuclear receptor bound to a ligand, such as a xenobiotic or steroid. Other examples are those capable of regulating transcription of a human CYP3A4 gene when contacted with a nuclear receptor consisting of a heterodimer of PXR (pregnane X receptor, otherwise known as SXR (steroid and xenobiotic receptor)) and RXR (9-cis retinoic acid receptor), or CAR (constitutive androstane receptor-β) and RXR.

The inventors believe that certain nucleic acid molecules which have substantially the same nucleotide sequence as a regulatory nucleic acid molecule of the invention would also have sufficient genetic information for reproducing the constitutive and xenobiotic induced tissue specific and developmental expression of the CYP3A4 gene that is observed in a human. Accordingly, it will be understood that nucleotides could be modified or deleted in regions of the regulatory nucleic acid molecule, more specifically, those regions which do not contain an enhancer such as those described above, without significantly limiting the capacity of the molecule to regulate transcription of the human CYP3A4 gene.

The inventors recognise that it would be advantageous to provide an animal model further capable of reproducing the expression of other human genes, specifically those genes encoding products which modify or modulate the therapeutic activity of exogenous and endogenous compounds used for therapy and cause drug-drug interactions, for example, cytochrome P450 genes or ABC transporter superfamily genes, for example, P-glycoprotein (otherwise known as MDR-1). The regions controlling the constitutive and xenobiotic induced tissue specific expression of some of these genes are known, and in some instances, non-human animal models have been generated. The inventors recognise that the genetic background of these animals could be incorporated into the non-human mammal of the present invention, for example, by conventional breeding techniques.

Thus in a fifth aspect, the invention provides a non-human mammal of any one of the first to fourth aspects of the invention, further comprising:

(c) a further regulatory nucleic acid molecule which is capable of regulating transcription of a human gene; and (d) a further reporter nucleic acid molecule for producing a detectable amount of a further reporter molecule for indicating regulation of transcription of the further reporter nucleic acid molecule by the further regulatory nucleic acid molecule wherein the further reporter and further regulatory nucleic acid molecules are arranged to permit the further regulatory nucleic acid molecule to regulate transcription of the further reporter nucleic acid molecule.

In one embodiment, the at least one further regulatory nucleic acid molecule has a sequence shown in SEQ ID NO:4. In another embodiment, the at least one further regulatory nucleic acid molecule has a sequence shown in SEQ ID NO:5.

Although the regulatory nucleic acid molecule of the invention described herein is sufficient for reproducing the constitutive tissue specific and developmental expression of the CYP3A4 gene that is observed in a human, the inventors recognise that aspects of the xenobiotic inducibility of the gene could be better reproduced in an animal by incorporating at least one human transcription factor that is capable of interacting with the regulatory nucleic acid molecule for regulating transcription of the human CYP3A4 gene. Examples of such factors are nuclear receptors. These receptors may be those capable of regulating CYP3A4 gene transcription in a human when the receptor is bound to a ligand, such as a xenobiotic or steroid. One example of such a receptor is the human PXR (pregnane X receptor, otherwise known as SXR (steroid and xenobiotic receptor)). Another suitable receptor is the human CAR (constitutive androstane receptor-β). Non-human animals comprising a human PXR or CAR receptor are known. The inventors recognise that the genetic background of these animals could be incorporated into the non-human mammal of the present invention, for example, by conventional breeding techniques.

Thus in a sixth aspect, the non-human animal of the invention further comprises at least one human transcription factor for regulating transcription of a human CYP3A4 gene. Preferably the transcription factor is a nuclear receptor. Preferably, the nuclear receptor is a heterodimer of the human PXR (pregnane X receptor, otherwise known as SXR (steroid and xenobiotic receptor)) and human RXR (9-cis retinoic acid receptor) or human CAR (constitutive androstane receptor-β) and human RXR.

It follows that the reporter nucleic acid molecule can be any molecule which is capable of detection when the reporter nucleic acid molecule is transcribed. For example, the reporter nucleic acid molecule could be the CYP3A4 cytochrome, or the mRNA transcript which is translated to produce the cytochrome. Those reporter molecules which are commercially available, including firefly luciferase, β-galactosidase, alkaline phosphatase, green fluorescent protein or chloramphenicol acetyl transferase can be used.

Thus in one embodiment, the reporter nucleic acid molecule is capable of producing a reporter molecule selected from the group of reporter molecules consisting of firefly luciferase, β-galactosidase, alkaline phosphatase, green fluorescent protein or chloramphenicol acetyl transferase.

While the non-human mammal of the invention, as exemplified below, is a mouse, the inventors believe that any other non-human mammal could be used in the invention, especially those for which standard transgenic techniques have been developed including for example, rat and rabbit. However, typically the non-human mammal is a mouse.

In another aspect, the invention provides a tissue of a non-human mammal of the invention.

In one embodiment, the tissue is an embryo capable of producing a non-human mammal of the invention.

In a further aspect, the invention provides a method of determining whether a compound is capable of effecting the transcription of a human CYP3A4 gene the method comprising the following steps:

(a) administering the compound to a non human mammal according to the invention and (b) determining whether the reporter molecule is produced by the reporter nucleic acid molecule in the mammal.

In one embodiment, the production of the reporter molecule indicates that the binding compound is capable of effecting the transcription of the human CYP3A4 gene.

Any compound can be tested in the method however, preferred compounds are xenobiotic or steroid compounds.

The inventors recognise that a non human animal which comprises a 5' flanking region of CYP3A4 gene but which is deficient for the region from −7836 to −7207 would be useful as a negative control in a method for determining whether a compound is capable of regulating transcription of the human CYP3A4 gene.

BRIEF DESCRIPTION OF THE FIGURES

FIG. 1. CYP3A4/lacZ transgene constructs used to generate transgenic mice. The upstream regions of the human CYP3A4 gene are depicted as open boxes with the position of the XREM at approximately −7.5 kb of the CYP3A4 gene indicated by cross-hatching. The 5'-flanking region extended from 56 bp downstream of the transcription initiation site to a HindIII site at −3,213 in the construct designated −3CYP3A4/lacZ and to a KpnI site at −12,926 kb in construct −13CYP3A4/lacZ. The coding region of the *E. coli* lacZ gene together with eukaryotic translational initiation and termination signals, transcription termination and poly adenylation sites are indicated by a solid box.

FIG. 2. Xenobiotic induction of hepatic transgene expression. Female mice from line 9/4 harbouring the −13CYP3A4/lacZ transgene were treated with various reagents. Histochemical staining of liver slices with X-gal revealed an increased zone of blue staining cells containing β-galactosidase after treatment with rifampicin, phenobarbital and pregnenolone 16α-carbonitrile compared with corn oil treated mice.

FIG. 3. Comparison of the xenobiotic induction profile of the −13CYP3A4/lacZ transgene with the mouse Cyp3a11 gene. Transgenic mice from line 9/4 were treated with a range of xenobiotic reagents and naturally occurring steroids. A. Transgene expression was assessed by determining β-galactosidase activity in total liver lysates using the ONPG assay. The units of β-galactosidase activity are given as $A_{420}$/mg liver/minute. Dexamethasone and pregnenolone 16α-carbonitrile were the most potent xenobiotic activators of the −13CYP3A4/lacZ transgene, while rifampicin treatment resulted in relatively low levels. The steroids pregnenolone and 17α-progesterone were very weak inducers. B. Hepatic expression of the endogenous mouse Cyp3a11 gene was examined in the same mice by Northern analysis. A similar pattern of induction to the CYP3A4/lacZ transgene was observed with both xenobiotic and endogenous regulators. The data are presented as the mean+/−the standard deviation for 3 animals.

FIG. 4. Dose response of −13CYP3A4/lacZ transgene expression after treatment with dexamethasone. A. Male mice from line 9/4 were treated with from 1 to 100 mg/kg dexamethasone. Higher doses of dexamethasone resulted in increased β-galactosidase activity (determined in liver lysates as described in FIG. 3). B. Zonal expansion of transgene expression with increasing doses of dexamethasone. X-gal staining of frozen liver sections revealed greater numbers of hepatocytes containing transgene-derived β-galactosidase activity after treatment with 1, 10 and 100 mg/kg dexamethasone. At low doses there are limited numbers of transgene-expressing cells immediately adjacent to the central vein. With higher doses there are more cells committed to transgene expression extending across the liver lobule towards the portal tract.

FIG. 5A-5E (SEQ ID NO:1) Sequence of the CYP3A4 5'-flanking region included in the −13 CYP3A4/lacZ construct. This sequence corresponds to −12,926 to +56 base pairs relative to the transcription initiation site of the CYP3A4 gene.

FIG. 6A-6D (SEQ ID NO: 2) Sequence of the 5'-flanking region of the CYP3A4 gene extending from −12,926 to −3,213 base pairs and representing the difference in sequence between the −13 CYP3A4/lacZ and the −3 CYP3A4/lacZ constructs.

FIG. 7. (SEQ ID NO:3) The "Xenobiotic-Responsive Enhancer Module" (XREM) of the human CYP3A4 gene. This region encompasses −7836 to −7207 base pairs relative to the transcription initiation site of the CYP3A4 gene.

FIG. 8A-8C(SEQ ID NO: 4) The 5'-flanking region of the human CYP3A7 gene (Genbank Accession No. AF329900). The extent of the sequences is −11,133 to +52 base relative to the transcription initiation site of the CYP3A7 gene.

FIG. 9A-9C(SEQ ID NO: 5) Sequence of the 5'-flanking region of the human MDR1 gene (p-glycoprotein gene) encompassing −10,000 to +200 base pairs relative to the transcription initiation site of the MDR1 gene. Sequence derived from within Genbank sequence Accession Number AC002457.

An embodiment of the invention is now described in the following Example which will be understood to merely exemplify and not to limit the scope of the invention.

EXAMPLE

Materials and Methods

Transgene constructs. Two transgene constructs were synthesized with the upstream 5' flank of the human cytochrome P450 CYP3A4 gene linked to the *E. coli* lacZ reporter gene (FIG. 1). The first construct, designated −3CYP3A4/lacZ, contained the region of the CYP3A4 gene from the HindIII site at −3213 bp relative to the transcription start site to nucleotide +56 bp downstream of the transcription start site. The other construct, designated −13CYP3A4/lacZ, included the region of the CYP3A4 gene from the KpnI site at −12,926 bp upstream to +56 bp downstream of the transcription start site. It includes the DNA sequences of the XREM region located between −7836 and −7208 in addition to the proximal promoter of the CYP3A4 gene. The DNA sequence of the CYP3A4 gene between −10468 bp and +906 bp has been determined and deposited with the GenBank/EMBL/DDJB database under accession number AF185589. Additional sequence information covering the region −10,469 bp to −12, 926 bp was obtained from publically accessible Genbank files. The *E. coli* lacZ reporter gene comprises the coding region for the bacterial enzyme β-galactosidase flanked by DNA sequences for eukaryotic translational start and stop signals, SV40 transcriptional termination and polyadenylation signals and an intron. The CYP3A4/lacZ transgene constructs were released from vector sequences and purified on agarose gels prior to microinjection Generation of transgenic mouse lines. Mice carrying the CYP3A4/lacZ transgenes were created by microinjection of the DNA constructs into the pro-nuclei of zygotes harvested from FVB/N strain mice. Microinjection and manipulation of embryos were carried by standard techniques. Stable transgenic mouse lines were established by breeding from transgenic founders identified by Southern analysis.

Administration of xenobiotics to mice. 8-10 week old male and female mice hemizygous for the −3CYP3A4/lacZ and −13CYP3A4/lacZ transgenes were used to test the ability of a range of xenobiotics and hormones to activate expression of transgene-derived β-galactosidase. Mice were administered the following reagents and vehicles by single daily intraperitoneal injection for 4 days: rifampicin/corn oil; dexamethasone phosphate/$H_2O$; pregnenolone 16α-carbonitrile/2% Tween 20 in $H_2O$; phenobarbital/$H_2O$; clotrimazole/2% Tween 20; phenytoin/2% Tween 20; 17α-OH progesterone/2% Tween 20; pregnenolone/2% Tween 20. All reagents were supplied by Sigma Chemical Co. (St Louis, Mo.) except for dexamethasone phosphate which was obtained from Faulding (Mulgrave, Australia) and pregnenolone 16α-carbonitrile from Upjohn Co. (Kalamazoo, Mich.). The dose used for all reagents to test for induction of the transgene was 100 mg/kg body weight. Dose response studies were carried out in the range of 1-100 mg/kg with male hemizygous transgenic mice.

Analysis of transgene and mouse Cyp3a gene expression. β-galactosidase activity was visualised in slices and frozen sections of liver and other tissues by staining with X-gal (5-bromo-4-chloro-3-indolyl-β-D-galactopyranoside). Tissues were fixed in 0.25% glutaraldehyde, 0.1M phosphate buffer pH7.3, 5 mM EGTA, 2 mM $MgCl_2$: washed in 0.1M phosphate buffer pH7.3, 0.01% sodium deoxycholate, 0.025% NP40, 2 mM $MgCl_2$ and stained by incubation at 37° C. in wash solution supplemented with 1 mg/ml X-gal, 5 mM potassium ferricyanide, and 5 mM potassium ferrocyanide. The level of β-galactosidase activity was determined in whole liver homogenates [100 mg fresh tissue/ml 0.25M Tris-HCl (pH 7.3)] using the O-nitrophenyl-β-D-galactopyranoside (ONPG) assay according to standard techniques. After appropriate dilution the homogenate was incubated with β-galactosidase assay reagent (0.1M sodium phosphate buffer (pH7.3)/1 mM $MgCl_2$/50 mmol β-mercaptoethanol/0.88 mg/ml ONPG) at 37° C., quenched by the addition of 1M $Na_2CO_3$ and the absorbance at 420 nm determined. The units of β-galactosidase activity are given as $A_{420}$/mg liver/minute.

The levels of endogenous mouse Cyp3a mRNA expression were determined by Northern analysis using a riboprobe complementary to nucleotides 852-1061 of the mouse Cyp3a11 cDNA. Filters were stripped and reprobed with an 18S rRNA oligonucleotide to normalise loading.

Results 4 transgenic lines were generated with the construct containing the −3.2 kb region of the human CYP3A4 gene linked to lacZ. Transgene-derived β-galactosidase activity was not detected in kidney, large and small intestine, spleen, lung and liver tissue from mice for all 4-3CYP3A4/lacZ transgenic lines treated with vehicle or xenobiotics (Table 1). In contrast, transgene expression was readily detected in 3 of the 4 lines carrying the −13CYP3A4/lacZ construct. Line 9/4 had a very low constitutive level in the liver, with β-galactosidase detected only in isolated hepatocytes adjacent to major blood vessels. Administration of xenobiotics resulted in robust expression in a zone of cells surrounding the central vein (FIG. 2). As the basal level of transgene expression in untreated mice in line 9/4 is extremely low, induction is obvious and is essentially an off/on process. Expression in other tissues in mice from line 9/4 was restricted to the gut, predominantly in the villi of the small intestine.

The relative degree of induction for a range of xenobiotics was analysed by determining the transgenic β-galactosidase activity in liver lysates of mice from line 9/4 (FIG. 3A). Dexamethasone and pregnenolone 16α-carbonitrile were the most potent inducers, while rifampicin activated the transgene to relatively modest levels. Phenobarbital, clotrimazole and phenytoin were intermediate inducers. The induction profile of the transgene in line 9/4 was similar to that observed for the endogenous Cyp3a11 gene in the same mice (FIG. 3B), likely reflecting the activation profile of the mouse rather than the human PXR. Activation of the transgene was observed with naturally occurring steroids such as pregnenolone and 17α-progesterone, however the induction was weak compared with xenobiotics.

There was a marked gender difference in hepatic transgene expression, with lower-levels observed in females than in males for most reagents. Such a male-predominant pattern was not evident in the induction profile of the mouse Cyp3a11 gene. Indeed higher levels of Cyp3a11 mRNA were observed in females than males after treatment with rifampicin and pregnenolone 16α-carbonitrile. The reason for this apparent reversal in gender-related transgene expression pattern is not known. However, as Cyp3a11 mRNA is only just detectable in males of the FVB/N strain of mice, it may be attributed to the relatively greater degree of induction of the mouse Cyp3a11 gene in males compared to females (FIG. 3B).

The other line which showed significant transgene expression –15/10, had a higher constitutive level in both the liver and small intestine in untreated mice.

Expression was not detected in other organs, confirming the tissue specificity observed in line 9/4. The same set of reagents were capable of increasing hepatic and intestinal transgene expression to the same levels as in mice from line 9/4. However, the overall degree of induction was not as great as observed in line 9/4 due to the higher basal level in line 15/10. The induction profile was similar with dexamethasone being the most potent activator and rifampicin the least (data not shown).

Dose response of xenobiotic induction. The activation of transgene expression in line 9/4 by dexamethasone was dose-dependent over the range 1 to 100 mg/kg (FIG. 4A). The higher transgene-derived β-galactosidase activity in liver homogenates from mice treated with increasing doses of dexamethasone was associated with an expanded zone of cells which were stained by X-gal. At low doses of dexamethasone a ring of hepatocytes only 1-2 cells thick around the central vein expressed the transgene (FIG. 4B). With 100 mg/kg dexamethasone the zone of X-gal positive hepatocytes increased to up to 10 cells, approximately midway between the central vein and the portal triad. A similar dose-dependent expansion of hepatocytes expressing the transgene was observed with other reagents and also in line 15/10 which also contained the –13CYP3A4/lacZ construct.

TABLE 1

Expression of CYP3A4/lacZ transgenic lines

| Construct | Line No. | Copy No. | Liver Basal | Liver Inducible | Small Intestine |
|---|---|---|---|---|---|
| -3CYP3A4/ lacZ | 13 | 15 | - | - | - |
| | 24 | >100 | - | - | - |
| | 31 | 80 | - | - | - |
| | 39 | 10 | - | - | - |
| -13CYP3A4/ lacZ | 13/5 | 70 | - | - | - |
| | 9/4 | 5 | + | ++++ | + |
| | 9/7 | 50 | - | + | - |
| | 15/10 | 8 | ++ | ++++ | ++++ |

The invention claimed is:

1. A non human mammal whose genome comprises:
   a regulatory nucleic acid molecule comprising the nucleotide sequence shown in SEQ ID NO:1; and
   a reporter nucleic acid molecule for producing a detectable amount of a reporter molecule for indicating regulation of transcription of the reporter nucleic acid molecule by the regulatory nucleic acid molecule;
   wherein the reporter and regulatory nucleic acid molecules are arranged to permit the regulatory nucleic acid molecule to regulate transcription of the reporter nucleic acid molecule.

2. A non-human mammal whose genome comprises:
   a regulatory nucleic acid molecule comprising the nucleotide sequence shown in SEQ ID NO:2; and a reporter nucleic acid molecule for producing a detectable amount of a reporter molecule for indicating regulation of transcription of the reporter nucleic acid molecule by the regulatory nucleic acid molecule;

wherein the reporter and regulatory nucleic acid molecules are arranged to permit the regulatory nucleic acid molecule to regulate transcription of the reporter nucleic acid molecule.

3. A non-human mammal whose genome comprises:

a regulatory nucleic acid molecule comprising the nucleotide sequence shown in SEQ ID NO:3; and a reporter nucleic acid molecule for producing a detectable amount of a reporter molecule for indicating regulation of transcription of the reporter nucleic acid molecule by the regulatory nucleic acid molecule;

wherein the reporter and regulatory nucleic acid molecules are arranged by permit the regulatory nucleic acid molecule to regulate transcription of the reporter nucleic acid molecule.

4. A non human mammal according to claim 1, 2 or 3 further comprising a nucleic acid sequence encoding at least one human transcription factor for regulating transcription of a human CYP3A4 gene.

5. A non human mammal according to claim 4 wherein the transcription factor is a nuclear receptor.

6. A non human mammal according to claim 5 wherein the nuclear receptor is a heterodimer of the human pregnane X receptor and human 9-cis retinoic acid receptor or a heterodimer of human constitutive androstane receptor-β and human 9-cis retinoic acid receptor.

7. A non human mammal according to claim 1, 2 or 3 wherein the reporter nucleic acid molecule is capable of producing a reporter molecule selected from the group of reporter molecules consisting of firefly luciferase, β-galactosidase, alkaline phosphatase, green fluorescent protein or chloramphenicol acetyl transferase.

8. A non human mammal according to claim 1, 2, or 3 wherein the mammal is a mouse.

9. A tissue of a non human mammal according to claim 1, 2 or 3.

10. A method of determining whether a compound is capable of effecting the transcription of a human CYP3A4 gene the method comprising the following steps:

administering the compound to a non human mammal according to any one of claim 1, 2 or 3; and determining whether the reporter molecule is produced by the reporter nucleic acid molecule in the mammal.

11. A method according to claim 10 wherein the production of the reporter molecule indicates that the binding compound is capable of effecting the transcription of the human CYP3A4 gene.

* * * * *

SEQUENCE LISTING

<160> NUMBER OF SEQ ID NOS: 5

<210> SEQ ID NO 1
<211> LENGTH: 12983
<212> TYPE: DNA
<213> ORGANISM: Homo sapiens

<400> SEQUENCE: 1
ctggttcatc tcattgggac tggttggaca agagggtgca gcccacggag ggtgagccaa      60
agcagggtgg ggcgtcgcct cacctgggaa gcacaagggg tcgtggaatt ttctcccta     120 cccaaggaaa gccataaggg actgagcctg aggaactgtg cactctggcc cagatactgc     180
acttttccca tggtctttgc aacccgcaga ccaggagatt ccctccggtg cctatgccac     240
cagggccctg ggtttcaagc acaaaactgg gcagccattt gggcagacac cgaactagct     300
gcaggagttt tttttttttt tttccatacc ccattggcac ctggaacgcc agtgagacag     360
aaccgttcac tcccctggaa aggggctga aaccagggat ccaagtggtc tggctcggtg     420
ggccccaccc ccatggagcc cagcaaacaa agattcactt ggcttgaaat tcttgctgcc     480
agcacagcag cagtctgaga ttgacctggg accctcgaac ttggttgggt gctgtggggg     540

-continued

| | |
|---|---|
| ggcatcttcc attgctgagg cttgagtagg tggttttacc ttcgcggtgt aaacaaagct | 600 |
| gctgggaagt ttgaactggg tggagctcac cacagctcag taaggccact gtggccagac | 660 |
| tgcctctctg gatttctcct ctctgggaag gatatctctg aaaaaaaggc agcagcccca | 720 |
| gtcagggact tatagatgaa accccatct ccctgggaca gagcccctcg gggaagaggt | 780 |
| ggcttccacc attgtggaag actgtgtggc aattcctcac ggatttagaa ctagagatac | 840 |
| catttgaccc agcaatccca ttactgggtg tatacccata ggattataaa tcattctact | 900 |
| ataaagacac atgcacactt atgtttattg taacactatt tacaatagca atgacctgga | 960 |
| accaatccaa aagcccatca atgatagact gaataaagaa aatgtggcac atatacactg | 1020 |
| tggaatacta tgcagccata aaaaaggatg agttcatgtc ctttgcagag acatggatga | 1080 |
| agctggaaac catcattctc agcaaactag cacaataaca gaaaaccaaa cactgcatgt | 1140 |
| tgtcactcat aagtgggagt taaacaatga gaacacatgg acacaggag gggaacgtca | 1200 |
| cacactgggg catgtcgggg agtggggcc tacgggaggg atagcattag cagaaatacc | 1260 |
| taatgtaggt gacgggttga tgggtgcagc aaaccaccat ggcacatata cacctatgta | 1320 |
| ataaaactgc acgttctgca catgtacccc agaacttaaa gtataattaa taataataat | 1380 |
| aatttctggg catgtaagta gctgtctttc aggttctact ttgatacata ttctgagaga | 1440 |
| attaaacctg tcaaagaaac cttgactttc aatggcaggc actggaattg accctaataa | 1500 |
| tgtgttttgg ggtaagccta ctcatattct caacctgtct gcagtagtcg ttagaatctg | 1560 |
| aacttcctga agttcatgtg caaagttgag ttaattgttt aatattcaac aaggattatg | 1620 |
| ccagtaagat ggtaggaaaa tattagatat gtgtcatcac tgctggtatt atttaaactg | 1680 |
| caacatattt tagctggctg ctgatctcag ccaccatgcc tgcattttat ctctgtctcg | 1740 |
| tggtctgcaa ccttggaagc tttgaactta gctcatagaa tcctgggcat caagaacatg | 1800 |
| tggttctaat ggctagatag ggaatgagag taaaaggatt ttgcccacgg tcacgtgagt | 1860 |
| aaacaacaga tttggagggg tctggactac tgtgatgact tcattctgac aatatgttcc | 1920 |
| agttgtcctt tcatttcctc ctaatcacat gtctggtctg atctggctgt ttcccacctt | 1980 |
| ccaattcctg ccttctccaa tgctcccttc cgtaggtcac tctgtggctc agagaccctg | 2040 |
| cttagcaagc gcccaacctt tcaattattt gttcagtaaa acttgaactc atgtctcccc | 2100 |
| ttcttgataa aaagaaaata cgttatgtaa tgtcgggtta ctctataact cttgtcctgt | 2160 |
| ctctcggcaa ctactgaact aactgttttc atattgagca aacgtttatg gaaggactgc | 2220 |
| caagagtcag gtactaggct tggtaatatt ccccgttctc tctagtcaaa gccaacacca | 2280 |
| gccagacttg cagatctagg tcccaagccc actgcagatc acaggccagg gtctggtctc | 2340 |
| ctctgagctc ctttgggagg gaaagacaga attattaaca cccatttgt agattaggca | 2400 |
| actgaggctg aggaagttta ataactcag acagggcctg cacgtcagtc atattccaag | 2460 |
| gatccctact cactgtcttc tctctacaga acgagatgtc tctggagtcc atagaaagcc | 2520 |
| caggagcctg gctgggcacg gtggctcctg cctgtaatcc cagcactttg ggaggccgag | 2580 |
| gcaggcagat cacctgagct caggagttca agaccagcct gggcaacatg gcaaacccc | 2640 |
| atctctacta aaaatacaaa aaattagctg ggcgtggtgg tgcatgcctc taatcccagc | 2700 |
| tacttgggag gctgaggcac aagaattgct tgagcccagg aggcagcagt tgcagtgagc | 2760 |
| tgagattgtg ccagtgcact ccagcctggg caacagagca agattccatt tcaaaaacaa | 2820 |
| aaacaaacac aaacaaacaa acaaaaatag aaagcccagg gaccacctgc gtcaggttcc | 2880 |
| cagccacacc ttttttcttgt cctcctctgt ctctggcatc ttctcacagg ttcctaattg | 2940 |

```
tttgtggttg cacaaattca aaatcccaga aaaattacca cttcacaccc actcagatgg   3000
ctattttttt tttgaaggaa gataacaagt gttgacaaga acatggagaa attggaattc   3060
tcacccattg ctggtgagaa tgtaatacgg tgctgctgct atggaaaaca gcttggagtt   3120
tcctcaaaaa gttcaacaga atttcaatgt gacccagcaa ttcccctcta agttatagat   3180
ctgagaggat taaaaacagt tactaaaata cacggactca catatttcta acagtccaat   3240
tcacaagggc caaaaggtgc taatagccca catgtccatc gatggatgga taaataaatt   3300
gtggtctatc catacaatgg aatattattc ggccataaat ggaatgaagt actgacgcat   3360
gctacagaat ggatgaaccg caaaaaaaat ggatgaacac atgctacaga atggatagcc   3420
tcactttact atgaagtgaa ggccagaaac gaagtccata tattgcatca tacaaaatat   3480
ccagaagagg gaagcccaca gagacagaat gtgcaatggt ggatgccagg gtctggggag   3540
aggggagagt ggggagaaac tgctcaactg gtacaggctt tattttggaa tgatgggaac   3600
attttgcaac tagatagagg tagtgattgc agaaacagag atgtactgaa ttccactgat   3660
ttttttcacc ttaaaatggt taattttcag tcctgagatt ggataatcat aaaaaaatgg   3720
ttaattttat gttatgtgaa tttcatccct atacatattt taaacctcag aaatatacac   3780
tagcaggcat ggaacaggtc actgtggtgc ctgccaagcc cggtgatgtt atctggggtc   3840
cccggccagc cttaagcctc ttgctgaccg gtggagggca gaacctttgc cctaaaagta   3900
taatatccac atgctggcat gattcctggc cagatggctt ctttattagc agtaattgaa   3960
actgcctcga tacagacact gtaccttgca accaaaaaat gactcaacaa tgataataag   4020
ggttaagctg ggccttttctc tctttgccag ttaaattata tttattatag cttgacatga   4080
aaaacaaagc aactccaaca ggtatcacaa gggcaaagga catgaacatt ttatcaaaga   4140
agaaatgcag ctgtcaaaaa tacagaaata ttcaaccttg ttcataataa agtggctggg   4200
ctcagtggtt catgcctgta atcccagtgc tttgcaaggc tgagacagga ggatcatttg   4260
aagccagaag ttcaagacca tcctaggcaa gtcagttcaa taccagactt catgtctaca   4320
aaacatcaaa aaattagcca ggcatggtga tgcatgcctg ttgtcccagc tactcaggag   4380
gctgaggcag gagaattgct tgagcctggg aggctgcggt ggcggtgagc catgattgtg   4440
ccattgtact ccagcctggg caatgcagca agactgtcta aataacaaaa ataatagtaa   4500
agaaaaggat tgggatgcca tttacttgcg tattcaatac acagagttaa aagtaatttc   4560
tacgttttct atttttttat tactaaaaaa agctggacca ttctcacagc ctgaaatgct   4620
tctcactttc ccttcttctg tccaaacact tctctatgat aatgcaaaca gtcactcctt   4680
taggaagact tcaccccagg tagttccaga tcccccttatc tctgccttcc cagaactcct   4740
ggtgtctctc cagttccctc cgtgtggtga agtaccctac ctagggtttc agtatggctc   4800
tgtctgcaaa ggtcttgttc acaccttccc ttatggttct gttgccctgt gttgtgtcat   4860
agcacagggc acagtggaga acccattcac actgatagag agggccccat ggtcctggag   4920
ataaccatgt aaccgatcag aataaggcat tgagggctgg gtgtcaggcg tgggctgcac   4980
ttgggtgggc aggtcccctg gaaagtcact gggtttggca agcttcctag taacatgtct   5040
ctctggggtc ccccttggaa cttcatgcaa aaatgctggt tgctggttta ttctagagag   5100
atggttcatt ccttttcattt gattatcaaa gaaactcatg tcccaattaa aggtcataaa   5160
gcccagtttg taaactgaga tgatctcagc tgaatgaact tgctgaccct ctgctttcct   5220
ccagcctctc ggtgcccttg aaatcatgtc ggttcaagca gcctcatgag gcattacaaa   5280
gtttaattat ttcagtgatt attaaaacctt gtcctgtgtt gaccccaggt gaatcacaag   5340
```

```
ctgaacttct gacaagaaca agctatcata ttcttttcaa ttacagaaaa aagtaagtta    5400
attgatagga ttttttttgt ttaaaaaaaa tgttactagt tttgaaaagg taatatgtgc    5460
acatggtaaa cactaagaag gtataagagc ataatgcttt tatactacta agaataatgt    5520
tttctctaag ttttttttgg tagatgcttt catcagatta agaaaattcc ctgctattag    5580
ttgttgaagg tttttatatc ataaatgaaa gttgaatatt attatcatat attattaata    5640
tattgttatt gaactatcaa agccttttcc taaaaccatt gagatgatct tataaccatt    5700
ctcctttaac ctgttgacga gatcattggt atttatacta tttctctgtt aaccattctt    5760
gagtctcagg tttaaattca acttggtcat ggtgtgtcat ctttgatcat tgctgtctgt    5820
ggcttgctac tgttttgttt aggattttg cactgatgct catcaatgag actggcatgc     5880
catcttcctt tgcagtcctg atttttttct gatttggatc atgtggttat ggccctcatg    5940
gaatgagttg ggcatgatgc cttttttca tgtctctgga ttgatgggac actttggatt     6000
ctctccagat ggccctcaat ggtccctgcc tcctcattgt taggccctg ggcaagccct      6060 tctcatttct ggtaggccca ggaacctgtg ggggttttgt tgtttgttt gtttcttgag      6120 tcggagtctc actctgtcac ccaggctgga gttggagtgc aatggcccga tcttggctca    6180
ctgcaacctc cacctcccag attcaagcaa ttctcctgcc tcagcctcct gagtagctgg    6240
aattacaggc acccaccgac acccctgct aattttgta tttttagtac agatggggtt      6300
tcacaatatt ggccaagctg gtctcgaact cctgatctca tgatctgccc ggcttggcct    6360
cccaaagtgt tgagattaca agcatgagcc accacccca gtgaacctgt ggttttaga      6420 agctccccat gcatgtgaat gctgtgagca tcccaggatg acagccactg tgtgttcagc    6480
tgttggaact gtgagaaagc accagtggga ccttctccag cacctgcctg ctgagttcat    6540
ggaagaggct tgttggggag atgatgccct ggctgactcc tgaaggatgg ttaggaatgc    6600
accagatgga agctgggttg gacccactct atgctgaaga acagcttgtg tggacacaag    6660
gagacacgga tatgtcattt tgtagagcc tgaggagtgt ccaatcacac catttgctta    6720
aaacatcatg cacacttgga aaagtggact gagaccgaat gaagaagcta acagtggcca    6780
gatcagaaag ggtcttgtgt tacttcctag agatacttag atttatcct gtgggtgata     6840 ggagcagttg gagggactga agacaaggaa agaaacatgt tcaagatct atgttttca     6900 agacgctttt ctggtggctg agtagggaat tccctggata agtcctgccc agggtcaggc    6960
aaaacaagtt aggggttac tgaaataagg agtatgagaa atggtgtagg ttgtgctgac     7020
gttttgtaac acatctcatg atgatcttca tttccttcac taatttcctg tttcattaat    7080
tcccttccac gtgctcttct gaaatttgcc tcacattctc tgattctct tttacctgtt     7140 ggtttcatca ccttttactt tttgctttcc tggaaacaca aatgattctg attgtgacat    7200
gtcagaatta tttgcaacat ttgcctttct gctgaaacca tgagttcact gaatacacaa    7260
tttagtaaag tgtaggatgc acatgtcgtt ttcgtggtca caaccagctc tgtagcattt    7320
tataactaca ctggcagtgt gctgggaggt gtagagagaa atatttatca catgtgtggc    7380
tgacacaacc tgccaagtta ttttaggagc ctccttggaa tcccagcaag aatgctaccg    7440
gcacaatttg taatcacagc atcctgctcc atgccttggc ttcatggcat agtcacttct    7500
gcaagtctct ttccagctgt ctgttccat gtctataaag tatgagttaa atcatcctaa     7560
cactactcat cttacaaagt tttcttgctg atgttaagag agttgggaaa gaactgtata    7620
aactgtgaag tgccatggag atgttagtgg ttactttatc aagaaataga cactctagaa    7680
tggagtagaa agccaacagt tatgattgag tcctcctcct cttcttcttt ttattaattt    7740
```

```
ataaagaaaa gaggtttaat tgactcacag ttccatatgg ctggggaggc ctcgggaaac   7800
tctcagtcat agcaggaggc aaaggggaag aaggcacctt cttcacaagg cggcaggaga   7860
gagagagctc ctgttctttt ttgtcataaa gtctacagaa gtgcttatac ttcaggacaa   7920
gggcaggcag agagaaggaa ggacattgct tcaccccagc cctcactgac gagtttgcta   7980
ggggacctca ctttgtccca gagtagggca gaactctggc cactacccat tcagaaggcc   8040
tgggctgcac tgctagttcc tcactaactc tgtgtggcct tgggcaaggt tgggcctgtg   8100
ttaacagatt atgaccctgg gctctcaagc tagaggatct aaatttgaat cctggctctg   8160
ctaaagcaat tagtgatgta aactttaatg ggtcagttaa ccttcctgtg gcttagtttg   8220
ctcatctgta aaatagggat cataacagta tcaataccac atgattgttg gacagattga   8280
atcagttaat gcaggggaag tacttagcat gacacgtatt cactatcatt tcctggagta   8340
agagctgtgt gtgagtgggt gtgagcatgt gtgaaacctt ttctctgcaa tctcagttaa   8400
gaaaccaatc cagaatttaa agttcagggc ctaaatgggg ggttatcttc tcccagttcc   8460
atcctatccc acctttgctc ttcctcccgc ccacaggagc tgttggtcct tgattgggct   8520
ggaagacctg gtggaccctg agtgatctat aagaggagaa tagagaacag gaatgtctt   8580 caaaaatcta gagggacaca gaggctgaga ggcaggcagt cctgcagggt cttctgattg   8640
ggacaaggag aaccttggtc ttcacaggcc aattctggtc agtttccccc atggacagat   8700
gaggaaacag gcccaggaat atccaaggtc tcacacttcc catctgtcaa gtcttgttga   8760
ttctgttgta ttcatgtctc tcaaagggag atagagttta gggaagaaag aaggatcaac   8820
tgtgtctgat accactggga gcttaagtaa agggttcttt tacttcatag catttatccc   8880
aatttgtaat tcagtattat ttgtgtggct gtttggtgtc tctttctcct atatgagtgc   8940
tagcttcata agggcaagga ttttgattct ttaatattta gtgcttgcca catgccctga   9000
acacagcagg catacaggct aaccaacata cagtggcatg aaagtcatga aagtgagaca   9060
cctacctcct ccagtgccaa gagagcataa ccatgcacct gtcactctcc tcaacaccac   9120
ccccaagcat gaggcccaaa agcattagct aatcccctcc tccagccact aaaacttaaa   9180
ggccaggtgt ggtggctccc atctgaaatc ccagaacttc aggagacagc agcaggagga   9240
tcacttgagg ccaggagttt gagatcagcc tgggcaacat agctaggtcc catctgtact   9300
aaaaattagc tgggcgttgt tgcatgcctg tagtcccagc tactaaggag gctgaggtgg   9360
gaggatcact tgagcccagg aggtggaaac aacagtaagc tataatcaca gcactgaact   9420
ctagcctggg caacagagtg acaccctgcc tcaaaacaat tttaaaaata aataagagca   9480
aaacttagat accacgtggt caccccaaca tgcaaaatca agttttcccc tactgagaag   9540
aatggggact tgacagctga gttacagaga gataatcttc ttcttctttt ttttttttg   9600 gtttacatcc tcaagatcat gacttgtgaa atttgaatcg aatacacatg taattccaga   9660
gcaatgttgc ctccgcatac catcagcaat tcacttggct actggaagtc aggataagct   9720
tcccagaaga gaggtaccac ttgggctacc aatataaaag gatgaaaata tcagagtgat   9780
ggtgttcttt acaacgttga gtccctggac agcctgtcca ctgatgctga tatctgagcc   9840
taatgcttct ctgaatgttg agattgaact ttgatccaat gaaactagaa cgagaaagaa   9900
gataagtctt tcattgttga taaggacatt atgtttctca tacttgtatg attatttttc   9960
cttagctgta ctataattat ctgcttattt gtctctgctc tatgtgctta gggtacaaag  10020
ttgaccaaga ccaactttgg ttggaagcat agtactaaga gcacagtact gagagcacag  10080
tattgagagc acagctttaa aaaacatgat gaaggcttta atacaggaaa tgagcagggg  10140
```

```
agaggcatgt ggtggttgga tgtatcttcc ttgacacagt cagtgcagct ctcagtagtc   10200
aagtccctac atgttagaag atgttacctt ctgtggaatt aagtggcaga acttgccttc   10260
aattattttc ctttgcagaa caacaccaac tgcattagtt aggacacagt gctggctgca   10320
tttaagtccc aagcgatgat tagtctctca ctgttggtat agattcaaac caatcagacc   10380
acctcctaaa gtttgtaggg caggtaaatc ctcatcttag aataaaaatc atcttaccaa   10440
gtatgtgttt tagaggcaag aagaaaacat atttgtttct gtaagagttt tgtttaaaaa   10500
aaatataaga aaggctctcg gtttaggtga ggtaatgaag ttgttgatag ttatcagatg   10560
acactggaat ctttacttct ctgaacgtgt tctgtgcatc tctcagtgtg ggaacataga   10620
gagggagatc ctccagcaat gccactgata tggtcagaaa ctgcatcttt ctttctccct   10680
gctgagatga gatggagtcc tttgttctag aagacccatg gtggtgccgc tgggagtaac   10740
ccttgagaca ggaacacaaa tcccaaccaa tttgtggttg cagccttgag tctcactatt   10800
tcccatagtg atgcgtagca gggaatggca ggtgcaccag agcaggagag gacctaatat   10860
ctcccttcct gttagctttt tataaagttt tattgtgatc agtagcagtt gggaagctac   10920
ttgcagtcac tgagcctcag tttctacatc tgtaaactgg ggatagtagc atggcccta   10980 cttaatgtgc tcagcaaagc cactgaaagg agacagaaat gtatctaaat taccctggac   11040
ttttatccta cctctcttgg ggattgtcac caccttccca tgtttgtcct ttttggtttg   11100
atgcttgctg tcacttcttt ccttaggtgc ctctctgtac ggctctttta tcccagggat   11160
tccagagtta cagcacatgc ataccaccat ccaagcatgt ttatttgtct cctgcttcac   11220
taggctgtcc ccaaggaaca tgtggctccc ggcacacacc tggcacaaca ctgcacatga   11280
cattcaccca cttggcctg aatctgacaa ggaatctggc atgatgttca cccactcagg   11340
ccaggtgccg agcagccctg gaggcttagg ggccagaggg atgggaaaag gtgtcttct   11400 ggggtgagta tcagttttctg caggagggct gaatgtgaga aagaataaag agagaaggaa   11460
gcgaacaagc acagcttaaa catcgcctat ttctattgag ttttaagaac gctgtgattt   11520
tgtttgtcat gcaatccatt catcaggcca ggcagacaca gaacttgggt gtgagtgacg   11580
ataatgagct gatataattt tcacaccctc atcactgaga tctctcccat caggaatggg   11640
tcagggagct cacaggtggc agcaactgct attacaggcc tcatctctac cagctcctgg   11700
ggcctgccct cctcccatta gaaaatcctc cacttgtcaa aaaggaagcc atttgctttg   11760
aactccaatt ccacccccaa gaggctggga ccatcttact ggagtccttg atgctgtgtg   11820
acctgcagtg accactgccc catcattgct ggctgaggtg gttggggtcc atctggctat   11880 ctggcagct gttctcttct ctccttctc tcctgtttcc agacatgcag tatttccaga   11940 gagaagggc cactctttgg caaagaacct gtctaacttg ctatctatgg caggacctt   12000 gaagggttca caggaagcag cacaaattga tactattcca ccaagccatc agctccatct   12060
catccatgcc ctgtctctcc tttaggggtc cccttgccaa cagaatcaca gaggaccagc   12120
ctgaaagtgc agagacagca gctgaggcac agccaagagc tctggctgta ttaatgacct   12180
aagaagtcac cagaaagtca gaagggatga catgcagagg cccagcaatc tcagctaagt   12240
caactccacc agcctttcta gttgcccact gtgtgtacag caccctggta gggaccagag   12300
ccatgacagg aataagact agactatgcc cttgaggagc tcacctctgt tcaggaaac   12360 aggcgtggaa acacaatggt ggtaaagagg aaagaggaca ataggattgc atgaagggga   12420
tggaaggtgc ccaggggagg aaatggttac atctgtgtga ggagtttggt gaggaaagac   12480
tctaagagaa ggctctgtct gtctgggttt ggaaggatgt gtaggagtct tctaggggc   12540
```

-continued

| | |
|---|---|
| acaggcacac tccaggcata ggtaaagatc tgtaggtgtg gcttgttggg atgaatttca | 12600 |
| agtattttgg aatgaggaca gccatagaga caagggcaag agagaggcga tttaatagat | 12660 |
| tttatgccaa tggctccact tgagtttctg ataagaaccc agaacccttg gactccccag | 12720 |
| taacattgat tgagttgttt atgatacctc atagaatatg aactcaaagg aggtcagtga | 12780 |
| gtggtgtgtg tgtgattctt tgccaacttc caaggtggag aagcctcttc caactgcagg | 12840 |
| cagagcacag gtggccctgc tactggctgc agctccagcc ctgcctcctt ctctagcata | 12900 |
| taaacaatcc aacagcctca ctgaatcact gctgtgcagg gcaggaaagc tccatgcaca | 12960 |
| tagcccagca aagagcaaca cag | 12983 |

<210> SEQ ID NO 2
<211> LENGTH: 9715
<212> TYPE: DNA
<213> ORGANISM: Homo sapiens

<400> SEQUENCE: 2

| | |
|---|---|
| ctggttcatc tcattgggac tggttggaca agagggtgca gcccacggag ggtgagccaa | 60 |
| agcagggtgg ggcgtcgcct cacctgggaa gcacaagggg tcgtggaatt ttctccccta | 120 |
| cccaaggaaa gccataaggg actgagcctg aggaactgtg cactctggcc cagatactgc | 180 |
| acttttccca tggtctttgc aacccgcaga ccaggagatt ccctccggtg cctatgccac | 240 |
| cagggccctg ggtttcaagc acaaaactgg gcagccattt gggcagacac cgaactagct | 300 |
| gcaggagttt ttttttttttt tttccatacc ccattggcac ctggaacgcc agtgagacag | 360 |
| aaccgttcac tcccctggaa aggggctga accaggat ccaagtggtc tggctcggtg | 420 |
| ggccccaccc ccatggagcc cagcaaacaa agattcactt ggcttgaaat tcttgctgcc | 480 |
| agcacagcag cagtctgaga ttgacctggg accctcgaac ttggttgggt gctgtggggg | 540 |
| ggcatcttcc attgctgagg cttgagtagg tggttttacc ttcgcggtgt aaacaaagct | 600 |
| gctgggaagt ttgaactggg tggagctcac cacagctcag taaggccact gtggccagac | 660 |
| tgcctctctg gatttctcct ctctgggaag gatatctctg aaaaaaaggc agcagcccca | 720 |
| gtcagggact tatagatgaa acccccatct ccctgggaca gagcccctcg gggaagaggt | 780 |
| ggcttccacc attgtggaag actgtgtggc aattcctcac ggatttagaa ctagagatac | 840 |
| catttgaccc agcaatccca ttactgggtg tatacccata ggattataaa tcattctact | 900 |
| ataaagacac atgcacactt atgtttattg taacactatt tacaatagca atgacctgga | 960 |
| accaatccaa aagcccatca atgatagact gaataaagaa aatgtggcac atatacactg | 1020 |
| tggaatacta tgcagccata aaaaggatg agttcatgtc ctttgcagag acatggatga | 1080 |
| agctggaaac catcattctc agcaaactag cacaataaca gaaaaccaaa cactgcatgt | 1140 |
| tgtcactcat aagtgggagt taaacaatga gaacacatgg acacagggag gggaacgtca | 1200 |
| cacactgggg catgtcgggg agtggggggcc tacgggaggg atagcattag cagaaatacc | 1260 |
| taatgtaggt gacgggttga tgggtgcagc aaaccaccat ggcacatata cacctatgta | 1320 |
| ataaaactgc acgttctgca catgtaccc agaacttaaa gtataattaa taataataat | 1380 |
| aatttctggg catgtaagta gctgtctttc aggttctact ttgatacata ttctgagaga | 1440 |
| attaaacctg tcaaagaaac cttgactttc aatggcaggc actggaattg accctaataa | 1500 |
| tgtgttttgg ggtaagccta ctcatattct caacctgtct gcagtagtcg ttagaatctg | 1560 |
| aacttcctga agttcatgtg caagttgag ttaattgttt aatattcaac aaggattatg | 1620 |
| ccagtaagat ggtaggaaaa tattagatat gtgtcatcac tgctggtatt atttaaactg | 1680 |

```
caacatattt tagctggctg ctgatctcag ccaccatgcc tgcattttat ctctgtctcg   1740
tggtctgcaa ccttggaagc tttgaactta gctcatagaa tcctgggcat caagaacatg   1800
tggttctaat ggctagatag ggaatgagag taaaaggatt ttgcccacgg tcacgtgagt   1860
aaacaacaga tttggagggg tctggactac tgtgatgact tcattctgac aatatgttcc   1920
agttgtcctt tcatttcctc ctaatcacat gtctggtctg atctggctgt ttcccacctt   1980
ccaattcctg ccttctccaa tgctcccttc cgtaggtcac tctgtggctc agagaccctg   2040
cttagcaagc gcccaacctt tcaattattt gttcagtaaa acttgaactc atgtctcccc   2100
ttcttgataa aagaaaata cgttatgtaa tgtcgggtta ctctataact cttgtcctgt    2160
ctctcggcaa ctactgaact aactgttttc atattgagca aacgtttatg gaaggactgc   2220
caagagtcag gtactaggct tggtaatatt ccccgttctc tctagtcaaa gccaacacca   2280
gccagacttg cagatctagg tcccaagccc actgcagatc acaggccagg gtctggtctc   2340
ctctgagctc ctttgggagg gaaagacaga attattaaca cccattttgt agattaggca   2400
actgaggctg aggaagttta ataactcag acagggcctg cacgtcagtc atattccaag    2460
gatccctact cactgtcttc tctctacaga acgagatgtc tctggagtcc atagaaagcc   2520
caggagcctg gctgggcacg gtggctcctg cctgtaatcc cagcactttg ggaggccgag   2580
gcaggcagat cacctgagct caggagttca agaccagcct gggcaacatg gcaaaacccc   2640
atctctacta aaaatacaaa aaattagctg ggcgtggtgg tgcatgcctc taatcccagc   2700
tacttgggag gctgaggcac aagaattgct tgagcccagg aggcagcagt tgcagtgagc   2760
tgagattgtg ccagtgcact ccagcctggg caacagagca agattccatt tcaaaaacaa   2820
aaacaaacac aaacaaacaa acaaaaatag aaagcccagg gaccacctgc gtcaggttcc   2880
cagccacacc tttttcttgt cctcctctgt ctctggcatc ttctcacagg ttcctaattg   2940
tttgtggttg cacaaattca aaatcccaga aaaattacca cttcacaccc actcagatgg   3000
ctattttttt tttgaaggaa gataacaagt gttgacaaga acatggagaa attggaattc   3060
tcacccattg ctggtgagaa tgtaatacgg tgctgctgct atggaaaaca gcttggagtt   3120
tcctcaaaaa gttcaacaga atttcaatgt gacccagcaa ttccctcta agttatagat    3180
ctgagaggat taaaacagt tactaaaata cacggactca catatttcta acagtccaat    3240
tcacaagggc caaaggtgc taatagccca catgtccatc gatggatgga taaataaatt    3300
gtggtctatc catacaatgg aatattattc ggccataaat ggaatgaagt actgacgcat   3360
gctacagaat ggatgaaccg caaaaaaat ggatgaacac atgctacaga atggatagcc    3420
tcactttact atgaagtgaa ggccagaaac gaagtccata tattgcatca tacaaaatat   3480
ccagaagagg gaagcccaca gagacagaat gtgcaatggt ggatgccagg gtctggggag   3540
aggggagagt ggggagaaac tgctcaactg gtacaggctt tattttggaa tgatgggaac   3600
attttgcaac tagatagagg tagtgattgc agaacacaga atgtactgaa ttccactgat   3660
ttttttcacc ttaaaatggt taattttcag tcctgagatt ggataatcat aaaaaaatgg   3720
ttaattttat gttatgtgaa tttcatccct atacatattt taaacctcag aaatatacac   3780
tagcaggcat ggaacaggtc actgtggtgc ctgccaagcc cggtgatgtt atctggggtc   3840
cccggccagc cttaagcctc ttgctgaccg gtggagggca gaacctttgc cctaaaagta   3900
taatatccac atgctggcat gattcctggc cagatggctt cttattagc agtaattgaa    3960
actgcctcga tacagacact gtaccttgca accaaaaaat gactcaacaa tgataataag   4020
ggttaagctg ggccttttctc tctttgccag ttaaattata tttattatag cttgacatga   4080
```

```
aaaacaaagc aactccaaca ggtatcacaa gggcaaagga catgaacatt ttatcaaaga    4140
agaaatgcag ctgtcaaaaa tacagaaata ttcaaccttg ttcataataa agtggctggg    4200
ctcagtggtt catgcctgta atcccagtgc tttgcaaggc tgagacagga ggatcatttg    4260
aagccagaag ttcaagacca tcctaggcaa gtcagttcaa taccagactt catgtctaca    4320
aaacatcaaa aaattagcca ggcatggtga tgcatgcctg ttgtcccagc tactcaggag    4380
gctgaggcag gagaattgct tgagcctggg aggctgcggt ggcggtgagc catgattgtg    4440
ccattgtact ccagcctggg caatgcagca agactgtcta aataacaaaa ataaatagtaa    4500 agaaaaggat tgggatgcca tttacttgcg tattcaatac acagagttaa aagtaatttc    4560
tacgttttct atttttttat tactaaaaaa agctggacca ttctcacagc ctgaaatgct    4620
tctcactttc ccttcttctg tccaaacact tctctatgat aatgcaaaca gtcactcctt    4680
taggaagact tcaccccagg tagttccaga tccccttatc tctgccttcc cagaactcct    4740
ggtgtctctc cagttccctc cgtgtggtga agtaccctac ctagggtttc agtatggctc    4800
tgtctgcaaa ggtcttgttc acaccttccc ttatggttct gttgccctgt gttgtgtcat    4860
agcacagggc acagtggaga acccattcac actgatagag agggcccat ggtcctggag    4920 ataaccatgt aaccgatcag aataaggcat tgagggctgg gtgtcaggcg tgggctgcac    4980
ttgggtgggc aggtcccctg gaaagtcact gggtttggca agcttcctag taacatgtct    5040
ctctggggtc ccccttggaa cttcatgcaa aaatgctggt tgctggttta ttctagagag    5100
atggttcatt cctttcattt gattatcaaa gaaactcatg tcccaattaa aggtcataaa    5160
gcccagtttg taaactgaga tgatctcagc tgaatgaact tgctgaccct ctgctttcct    5220
ccagcctctc ggtgcccttg aaatcatgtc ggttcaagca gcctcatgag gcattacaaa    5280
gtttaattat ttcagtgatt attaaacctt gtcctgtgtt gaccccaggt gaatcacaag    5340
ctgaacttct gacaagaaca agctatcata ttcttttcaa ttacagaaaa aagtaagtta    5400
attgataggg ttttttttgt ttaaaaaaaa tgttactagt tttgaaaagg taatatgtgc    5460
acatggtaaa cactaagaag gtataagagc ataatgcttt tatactacta agaataatgt    5520
tttctctaag tttttttttgg tagatgcttt catcagatta agaaaattcc ctgctattag    5580
ttgttgaagg tttttatatc ataaatgaaa gttaatatatt attatcatat attattaata    5640
tattgttatt gaactatcaa agccttttcc taaaaccatt gagatgatct tataaccatt    5700
ctcctttaac ctgttgacga gatcattggt atttatacta tttctctgtt aaccattctt    5760
gagtctcagg tttaaattca acttggtcat ggtgtgtcat ctttgatcat tgctgtctgt    5820
ggcttgctac tgttttgttt aggattttttg cactgatgct catcaatgag actggcatgc    5880
catcttcctt tgcagtcctg atttttttttct gatttggatc atgtggttat ggccctcatg    5940
gaatgagttg ggcatgatgc ctttttttttca tgtctctgga ttgatgggac actttggatt    6000
ctctccagat ggccctcaat ggtccctgcc tcctcattgt taggcccctg ggcaagccct    6060
tctcatttct ggtaggccca ggaacctgtg ggggttttgt ttgtttgttt gtttcttgag    6120
tcggagtctc actctgtcac ccaggctgga gttggagtgc aatggcccga tcttggctca    6180
ctgcaacctc cacctcccag attcaagcaa ttctcctgcc tcagcctcct gagtagctgg    6240
aattacaggc acccaccgac acaccctgct aattttttgta ttttttagtac agatggggtt    6300 tcacaatatt ggccaagctg gtctcgaact cctgatctca tgatctgccc ggcttggcct    6360
cccaaagtgt tgagattaca agcatgagcc accacaccca gtgaacctgt ggttttttaga    6420 agctccccat gcatgtgaat gctgtgagca tcccaggatg acagccactg tgtgttcagc    6480
```

```
tgttggaact gtgagaaagc accagtggga ccttctccag cacctgcctg ctgagttcat   6540
ggaagaggct tgttggggag atgatgccct ggctgactcc tgaaggatgg ttaggaatgc   6600
accagatgga agctgggttg gacccactct atgctgaaga acagcttgtg tggacacaag   6660
gagacacgga tatgtcattt ttgtagagcc tgaggagtgt ccaatcacac catttgctta   6720
aaacatcatg cacacttgga aaagtggact gagaccgaat gaagaagcta acagtggcca   6780
gatcagaaag ggtcttgtgt tacttcctag agatacttag attttatcct gtgggtgata   6840
ggagcagttg gagggactga agacaaggaa agaaacatgt ttcaagatct atgttttttca   6900 agacgctttt ctggtggctg agtagggaat tccctggata agtcctgccc agggtcaggc   6960
aaaacaagtt aggggttac tgaaataagg agtatgagaa atggtgtagg ttgtgctgac    7020
gttttgtaac acatctcatg atgatcttca tttccttcac taatttcctg tttcattaat   7080
tcccttccac gtgctcttct gaaatttgcc tcacattctc tgattctct tttacctgtt    7140 ggtttcatca cctttactt tttgcttcc tggaaacaca aatgattctg attgtgacat      7200
gtcagaatta tttgcaacat ttgcctttct gctgaaacca tgagttcact gaatacacaa   7260
tttagtaaag tgtaggatgc acatgtcgtt ttcgtggtca caaccagctc tgtagcattt   7320
tataactaca ctggcagtgt gctgggaggt gtagagagaa atatttatca catgtgtggc   7380
tgacacaacc tgccaagtta ttttaggagc ctccttggaa tcccagcaag aatgctaccg   7440
gcacaatttg taatcacagc atcctgctcc atgccttggc ttcatggcat agtcacttct   7500
gcaagtctct ttccagctgt ctgttcccat gtctataaag tatgagttaa atcatcctaa   7560
cactactcat cttacaaagt tttcttgctg atgttaagag agttgggaaa gaactgtata   7620
aactgtgaag tgccatggag atgttagtgg ttactttatc aagaaataga cactctagaa   7680
tggagtagaa agccaacagt tatgattgag tcctcctcct cttcttcttt ttattaattt   7740
ataaagaaaa gaggtttaat tgactcacag ttccatatgg ctggggaggc ctcgggaaac   7800
tctcagtcat agcaggaggc aaaggggaag aaggcacctt cttcacaagg cggcaggaga   7860
gagagagctc ctgttctttt ttgtcataaa gtctacagaa gtgcttatac ttcaggacaa   7920
gggcaggcag agagaaggaa ggacattgct tcaccccagc cctcactgac gagtttgcta   7980
ggggacctca ctttgtccca gagtagggca gaactctggc cactacccat tcagaaggcc   8040
tgggctgcac tgctagttcc tcactaactc tgtgtggcct gggcaaggt tgggcctgtg    8100 ttaacagatt atgaccctgg gctctcaagc tagaggatct aaatttgaat cctggctctg   8160
ctaaagcaat tagtgatgta aactttaatg ggtcagttaa ccttcctgtg gcttagtttg   8220
ctcatctgta aaatagggat cataacagta tcaataccac atgattgttg gacagattga   8280
atcagttaat gcaggggaag tacttagcat gacacgtatt cactatcatt tcctggagta   8340
agagctgtgt gtgagtgggt gtgagcatgt gtgaaacctt ttctctgcaa tctcagttaa   8400
gaaaccaatc cagaatttaa agttcagggc ctaaatgggg ggttatcttc tcccagttcc   8460
atcctatccc acctttgctc ttcctcccgc ccacaggagc tgttggtcct tgattgggct   8520
ggaagacctg gtggacccta agtgatctat aagaggagaa tagagaacag gaatgtctt    8580 caaaatcta gagggacaca gaggctgaga ggcaggcagt cctgcagggt cttctgattg     8640
ggacaaggag aaccttggtc ttcacaggcc aattctggtc agtttccccc atggacagat   8700
gaggaaacag gcccaggaat atccaaggtc tcacacttcc catctgtcaa gtcttgttga   8760
ttctgttgta ttcatgtctc tcaaagggag atagagttta gggaagaaag aaggatcaac   8820
tgtgtctgat accactggga gcttaagtaa agggttcttt tacttcatag catttatccc   8880
```

| | |
|---|---|
| aatttgtaat tcagtattat ttgtgtggct gtttggtgtc tctttctcct atatgagtgc | 8940 |
| tagcttcata agggcaagga ttttgattct ttaatattta gtgcttgcca catgccctga | 9000 |
| acacagcagg catacaggct aaccaacata cagtggcatg aaagtcatga aagtgagaca | 9060 |
| cctacctcct ccagtgccaa gagagcataa ccatgcacct gtcactctcc tcaacaccac | 9120 |
| ccccaagcat gaggcccaaa agcattagct aatcccctcc tccagccact aaaacttaaa | 9180 |
| ggccaggtgt ggtggctccc atctgaaatc ccagaacttc aggagacagc agcaggagga | 9240 |
| tcacttgagg ccaggagttt gagatcagcc tgggcaacat agctaggtcc catctgtact | 9300 |
| aaaaattagc tgggcgttgt tgcatgcctg tagtcccagc tactaaggag ctgaggtgg | 9360 |
| gaggatcact tgagcccagg aggtggaaac aacagtaagc tataatcaca gcactgaact | 9420 |
| ctagcctggg caacagagtg acaccctgcc tcaaacaat tttaaaaata aataagagca | 9480 |
| aaacttagat accacgtggt cacccaaca tgcaaaatca gttttcccc tactgagaag | 9540 |
| aatggggact tgacagctga gttacagaga gataatcttc ttcttctttt ttttttttg | 9600 |
| gtttacatcc tcaagatcat gacttgtgaa atttgaatcg aatacacatg taattccaga | 9660 |
| gcaatgttgc ctccgcatac catcagcaat tcacttggct actggaagtc aggat | 9715 |

<210> SEQ ID NO 3
<211> LENGTH: 632
<212> TYPE: DNA
<213> ORGANISM: Homo sapiens

<400> SEQUENCE: 3

| | |
|---|---|
| tctagagaga tggttcattc ctttcatttg attatcaaag aaactcatgt cccaattaaa | 60 |
| ggtcataaag cccagtttgt aaactgagat gatctcagct gaatgaactt gctgaccctc | 120 |
| tgctttcctc cagcctctcg gtgcccttga aatcatgtcg gttcaagcag cctcatgagg | 180 |
| cattacaaag tttaattatt tcagtgatta ttaaaccttg tcctgtgttg accccaggtg | 240 |
| aatcacaagc tgaacttctg acaagaacaa gctatcatat tcttttcaat tacagaaaaa | 300 |
| agtaagttaa ttgataggat ttttttttgtt taaaaaaaat gttactagtt tttgaaaagg | 360 |
| taatatgttg cacatggtaa acactaagaa ggtataagag cataatgctt ttatactact | 420 |
| aagaataatg ttttctctaa gttttttttg gtagatgctt tcatcagatt aagaaaattc | 480 |
| cctgctatta gttgttgaag gttttatat cataaatgaa agttgaatat tattatcata | 540 |
| tattattaat atattgttat tgaactatca aagccttttc ctaaaaccat tgagatgatc | 600 |
| ttataaccat tctcctttaa cctgttgacg ag | 632 |

<210> SEQ ID NO 4
<211> LENGTH: 11186
<212> TYPE: DNA
<213> ORGANISM: Homo sapiens

<400> SEQUENCE: 4

| | |
|---|---|
| ggatccagtt tcagctttct acatatggct agccagtttt cccagcacca tttattaaat | 60 |
| agggaatcct ttccccattg cttgttttttg tcaggtttgt caaagatcag atggttgtag | 120 |
| atgtgtggtg tttgttctga ggcctctgtt ctgttccatt ggtccatatc cctgttttgg | 180 |
| tactagtacc atgctctttt ggttactgta gccttgtagt atagtttgaa gtcaggtagc | 240 |
| gtgattcctc cagcttttgct ctttttgctt aggattgtct tgggaatgtg ggctctttt | 300 |
| tggttccata tgaaatttaa agtagttttt tttccaattc tatgaagaaa gtcattggta | 360 |
| acttgatggg gatggcattg aatctataaa ttaccttggg aagtatggcc attttcacga | 420 |

```
tattgattct tcctatccat gagcatggaa cattcttcca tttgtttgtg tcctctttga    480
ttttgttgag cagtggtttg tagttctcct tgaagaagtc cttcacctcc ctttaatttg    540
gattactaga tattttattc tcttagtaac aattgcaaat gggagttcac tcatgatttg    600
gctctctttc tgttattggt gtataggaat gcttgtgatt tttgcgcatt aattttgtat    660
cctgagactt tgctgaagtt gcttatcagc ttaaaaggat tttgggctga cgatgggg     720 ttttctaaat atacaatcat ggcatctgca aacaggaaca atttgacttc ctcttttcct    780
aattgaatac cctttatttc tttttcttgc ctgattgccc tggccagaac ttccaatact    840
atgttgaata agagtcatga gtgagggcat cgttgtcttg tgctggtttc aaagttttg     900 cccattcagt atgattttgg ctgtggtttt gccataaata gctcttatta ttttgagata    960
cgttccacca atacctactt tattgagagt ttttagcagg aagggctgtt gaattttgtc   1020
gaaggccttt tctacatcta ttgagacaat tatgtggttt tttaatcgtt gattctgttt   1080
atgtgatgga ttacatttat taatttgcat atgttgaacc agccttgcat cccagggatg   1140
aagcccactt gattgtagtg gataagcttt ttgatgtgct gctggattca gtttgccagt   1200
attttattga ggattttggc atcaatgttc atcaggata  ttggtctaaa attctctttt   1260
tttgttgtgt ctctgccagg ctttggtatc aggatgatgc aggcctcaga aactgagtta   1320
gggaggattc cctcattttc tattgattgg aatagtttca gaaagaatgg taccagctac   1380
tctttgtacc tctggtagaa ttcagctgtg aatccatctg gtcctggact ttttggttgg   1440
taggctatta attattgcct caattttagg gcctgttatt ggtctattca gacattcaac   1500
ttcttcccgg tttggtcttg ggagggttta tgtgtccagg aatttatcca tttcttctag   1560
attttctagt ttatttgtgt agaggtgttt atagtattgt ctgatggtag tttgtatttc   1620
tgtgagatcg gtggtgatat cccctttatc attttttatt gcatctattt aattcttctc   1680
tcttttcttc tttattattc tggctggcgg tctgtcaatt tttttgatct tttcaaaaaa   1740
ccagctcctg ggtttcactg attatttgaa gggttttttg tgtctctatt tctttcagtt   1800
ctcctgtgat cttagttatt tcttgccttc tgctagcttt tgaatgtgtt tgctcttcct   1860
tctctagttc tttgaattgt gatgttacag tgttgatttt agatcttttcc tgcttttctct  1920 tgtggtcatt tagtgctata aatttccctc tacacattgg tttacatgtg tctcagagat   1980
tctggtatgt tgtgtctttg ttctcattca tttcaagaac atctttactt ctgccttcat   2040
tttgttattt gcccagtagt cattcaggag caggttgttc agtcttcatg tagttgtgtg   2100
gttttgagtg agtttcttaa tcctgagttc taatttgatt gcactgttgt ctgagagaca   2160
gtttgttgtg atttccattc ttttacattt actgagcatg ctttatgtcc cattatgtgg   2220
tcaattttag aataagtgtg atgtgatgct gagaagaatg tatattctgt tgatttgggg   2280
tgtggagttc tgtagatgtc tattcagtcc actgggtgca gagctgagtg gacatgaaca   2340
ttttatcaaa gaagaaacac agctatcaaa aatccagaaa tattgaacct tgttaataat   2400
aaagtggctg gcctctggtt cattcctgta atctcagtcc tttgaaaggc tgagaaagga   2460
ggatcacttg aggccacaag ttcaagacca tcctagacaa gtcagttcaa gaccagactt   2520
catgtctaca aaacatcaaa aaattagcca ggcatggtga tgcatgcctg tcatcccagc   2580
tactcaggag gctgaggcag gaggattgct tgagcctggg agattgaagt ggcagtgagc   2640
catgattgtg ccattgcact ccagcctggg caatgcatca agactctgtc taaacaataa   2700
taataataat agtaatagta ataataataa taataaagaa aacggttggg acgccattcc   2760
ttacttattc aatacacaaa gttaaaagca atttctactt tctctatttt tttattacta   2820
```

```
aaaaaagctg aaccattctc acagcctgaa atgcttctca ccttcccctc ttctatacaa    2880
acacttctct gttgatgata atgcagacag tctctccttt aggaatactt cacaccaggt    2940
agttccagat cccctatctc tgccttccc agagctcctg tgtctcccc agttccctct     3000 gtgtggtgaa gtaccccac cttgggtctc agcatgactc gttctttgaa ggtcttgttc    3060
acattttccc ttatggttct gttcccctgt gttgtgtcac agcactgggc agagtggaca    3120
acccattcac accgatagag agggccccat ggttctggag ataaccatgt aactgatcag    3180
aatagggcat tgagggctgg gtgtcaggca tgggctgcac ttgggtgggc aggcccctg    3240 gaaagtcaca ggatttggca agcttcctag taacatctct ccctgggtc ctcttggaac     3300 ttcatgcccg atgctggatg ctggtttatt ctcgagagat ggttcattcc aataatcaat    3360
gaaactcatg tcccaactaa agttcataaa ctccagtttg taaactgaga taatctcagc    3420
tgaatgaact tgctgaccct ctgctttccc ccagcctctc agtgcccttg aaatcatgtc    3480
agttcaagca gccccatgag gcattacaat gtttagttat ttcagtgttt attaaaccct     3540
gccctatgct gaccccaggt gaatcacaag ctggacttct gacaaggaca agctatgata    3600
ttcttttcaa ttacagaaaa agtaagttaa ctgataggat tttttaaaga tgttactagt    3660
tttggaaagg taatttgtgc acatggtaaa caagaaggta taagaggata atgcttttat    3720
actgctgaga ataatgtttt ctctaatttt ttttggtaga tgctttcatc agattaataa    3780
aattcactgc tgttagttgt tgaaggtttt ttatatcatg aatgggagtt gaatattatc    3840
atgtattatt aatatattat tattgaacta gcaaaggctc ttcctaaaac aattgagatg    3900
atcttataat cgttctcctt taatctgttg atgagatcat tggtatttat acttttctc    3960 tgttaactat tcttgagtct caggtttaaa ttcaacttgg tcatggtgta tcatctttga    4020
acactcctgt ctctggcttg ctactattgt gttcagcatt tttgcactga tgccgatgaa    4080
tgagactggc atgtcatctt cctttgcggt cctgatttt ttcagatttg gatcatgtgg     4140
ccctcattga atgagttggg tgtgatgcct tcttttcat gtatctggat tgatgggaca     4200
ctttggagtc tctccagatg gccctcaatg gtccctgcct cctcattgtt aggctcctag    4260
gcaacccttt ctcatttctg gtaggcccag gaacctgtgg gttttatgtt tgtttgtttg    4320
tttgtttgtt tgttttttga gttggagtcc tgctttgtct cccaggctgg ggttggagtg    4380
caatggcctg atctcggccc actgcaacct ccacctcctg ggttcaagtg attctcctgc    4440
ctcagccttc tgtgtagctg ggattacagg catccaccac cactcctggc taattttgt    4500 attttagta gagacggggt tttacaatat aggccattgt gatctcttgg acaggctagt    4560
ctcaaattcc tgacctcatg atctgcctgc ctcagcctcc caaagtgctg agattacagt    4620
tttgtgcctc cacacacagt gaatctgtgg ttttaaaag ctcctcatgc atgtgaattc     4680
tgtgagcatc ccgggatgac agccactgtg tgtccagctg ttaaaactgt gagaaagcac    4740
cagcgggacc ctctccagca tttgcttgct gtggtcatga aagaggcttg ttggggagat    4800
gatgccctgg ttgactcctg aaggatggtt aggaatgcac cagatggaag ctgggttgga    4860
cccagtctat gctaaagaac agcttgtgtg gacacaagga gacacgaaca catcattttt    4920
gcagagcctg gggagtagcc aatcgcacca tttgcttaaa acaccgtgta cagttggaga    4980
agtggactga gacaggctga agaagctaac agtggccaga tgagaaaggg tcttgtgtta    5040
cttcctagat atacttagat tttatcctgt gagtgatagg aacagttgca gggactgaag    5100
ccaaggaagc atgctttaag attccatgtt ttttgagatg ctgtctggtg gctgagtagg    5160
gaattccctg gataagtact gcccagggta ggcaaaagaa gctaggaggt tactgaaata    5220
```

```
aggagtatga gaaatggtgt aggttttgct gatgttttgt aacacatctc atgacaatct    5280
tcatttcctt caccaatttc ctgtttcatt aattcccttc cacgtgctct tctgaaattt    5340
gcctcatatt ctttgatttc tcttttacat gttggtttca tcaccttttta cttttttgctt    5400 tcctggaaac acaaatgatt ctgattgtga catgtcagaa ttatttgcaa cattcccctt    5460
tctgctgaaa catgagctca ctgaatacac aatttagtaa agtgtaggat gcacatgttg    5520
ttttcatggt cataaccagc tctgtagcat tttataacta cactggcagt gtgctgggag    5580
gtgtagagag aaatatttat ctcatgtgtg gctgacacaa cctgccaagt tgttttagga    5640
gccttcttgg aatcccagca agaacaccac tgatgcaatt tgaaatcaca atgtcctgct    5700
ccatgccctg gcttcatggc ttagtcacgt ctgaagtcta tttctaacta tctgtttcca    5760
catctataaa gtatgagtta atcatcctca atactactca tcttacaaag tttttcttgct    5820 gatattagga gagttgggaa agaactgtat aaattatgaa gtgccatgga gatgttggtg    5880
gttactttat caagaaatag acactccaga atagagtaga aagaaaacag ttatgattaa    5940
gtcctcctcc tcttcttttt ttttaattta caaagaaagg tttaattgag tcacagttcc    6000
atatggttgg ggaggctcag aaaacttgca atcatggcag ttggcaaagt ggaagaaggc    6060
accttcttca caaggtggca ggagagagag agctcctctt ctttttttgtt gtaaagtcta    6120 cagaagtgca tatacttcag ggcaagggca ggcagggaga agaaaggaca ttgcttcacc    6180
ccagtcctca ctgacaagtt tgctttggga cttcattttg tcccagcata tgggacagag    6240
ctctggccac tacccattca gaaggcctga gctgcattgc tagttcccca ctaactctgt    6300
gtgtccttgg gcaaggctgg gcttatgtca aaagattatg accctgggct ctccagctac    6360
agaatctaca tatgaatcct ggctctgcta gagcaattag tgacgtaacc ttggatgggt    6420
cagttaacct tcctgtggct tagtttgctc atctgtaaaa tagggatcat aacaacatca    6480
ataccatggg ttgttagaca gattgaatca gttaatgcag ggtaaatact tagcatgaca    6540
cgtattcact atcatttcct tgagtaaaag ctgagtgtga gtgggtgtga aatgtgtga    6600 aacccttca ctgcaatctc agttaagaaa cccatcccata atttaaagtt cagggcctaa    6660
atgggtggtt atcttctccc agttgcatcc tatcccacct ttgctcttct cctgcccgta    6720
ggagctgttg gtcttttgatt gggctggaag acctggtgga ccctaagtga tctataagag    6780
aatgagaata gaggacaggg aatgtcttca aaactcctag agggacacag aggctgagag    6840
gcaggcagtc ctgcagggt cttctgattg ggacaaggag gaccttggtc ttcataggcc    6900
aattctggtc aatttccccc atggacagat gaggaaacag atccaggaat atccaaggtc    6960
tcacacttcc catctgtcaa gtcttgttga ttctgttgta ttcatgtctt tcaaagagag    7020
agagagttta aggaaagaaa gaaggatcaa ctgtgtctga tatcactggg agcttaagta    7080
aagggttctt ttacttcata gcattttccc caatttgtaa ttcagtatta ttttttgtcac    7140 tgtttagtat ctctttgtcc tattagagag atagcttcat caggacaagg attttgattc    7200 tttaatatt agtgcttgcc acatgccctg aacacagcag gcatacagac taaccaacat    7260
acagtggcat cgaagtgaga cacctacctc ctccagtgcc tagagtacat gtccatggac    7320
ctgtcactct cctcaacacc ccctaagc atgaggcccg aaagcattgc taatcccctc    7380
ctccagccac caaaacttaa aggccaggtg tggtggctcc tatctgaaat ctcagaactt    7440
taggagacag cagcaggagg atcacttgag gccaggaatt tgagcgagc ctgggcaaca    7500 tagctagaca ccatctgtac taaaaattag ctgggcatgg tggtataccct gtagtaccag    7560 ctactaagga ggctgaggta ggaggatcac ttgaacccag gaggtggaag ctacagtgag    7620
```

```
ctataaccac agcactgaac tccagcctga gcaacagagt gagaccctgc ctcaaaacaa    7680
tttcaaaaat aaataaataa aaacaaaact tagataccac gtggtcaccc caacatgcaa    7740
aatcaagttt tccccctactg agaagaatgg ggacttgaga gctgagttac agagagataa   7800 tctgccttt ttttttttt tttggtttac atcctcaaga tcatgacctg tgaaatttga      7860
atctaataca caaatcattc cagagcaatg ttgcttctgc ctaccacgag taattcactt    7920
ggccactgga agtcagaaca agcttcccag aagagaggta ccacttggac taccaatata   7980
aaaggatgaa aatatcggag tgaaggtgtt ccttgcatca ctgagtccct ggacagcctg   8040
tccactcatg ctgatatctg agcctaatgc ttctctgaat gttgagattt aactttgatc   8100
caatgaaacc agaccaagaa agaagaaacg tctttcattg ttgataagga catgattttt   8160
ctcacaattt tatgattatt tttccttagc tgtcctataa ttatctgctt atttgtctct   8220
tctccatgtg cttagggtac aaagttgacc aagaccaaga ataatgtctg ggagcacaat   8280
actgacagca cagcttaaa aacatgatga atgctttaat acaggaaatg agtaggggag    8340
aggcaagtgg tgcttgggtg ttcttccaat gcatagtatc ttccttgaca cagtcagtgc   8400
agctctcagt aggcaagtcc ctacatgtta gaagatgtta cttttctgtgg aattaggtgg  8460 cagaacatgc cttcaattat tttcctttgc agaacaacac caatttcatt agttaggaca   8520
gagtgctggt gcatttgaa ttccaagcaa cgattagtct atcactgttg gtatagattc     8580
caaccagtca caccacctcc tgaagtttgt tgggcaggta aatcttcatc ttagaataaa    8640
aatcatctta gccaagtaag tgttttagag gaaagaagaa aacataatcg tttccataag   8700
agttttgttt ctaaaaaat aagaaaggct ctttgtttag gtgagctaat gaagttgttg    8760
atagttatca gatgacactg gaatctttac ttgccagaat gtgttctgtg cacctctcgg   8820
tgtggcaaca tagagaggga gatcctccag caatgccatt gatatggtca gaaactgcat   8880 cttttctttct ccctgctgag atggggtcct ttgttctaga aaacccaggg ggtgccactg   8940
ggagtaaccc ttgagacagg aacacgaatc tcaaccaatt tctggttgca gccttgagtc   9000
ttactatttg ccatagtgat gcttagcaag gaatggcagg tgcaccagag cagcagagga   9060
cctaatatct cccttcctgt taacttttta taatatttta ttgtgatcag tatcagttgg   9120
gaagctactt gcagtcactg agcctcagtt tctacatctg taaactgggg atagtagcat   9180
ggccctattt aatgtgctca gcgaagccac tgaaaggaga cagaaatgta ccagaattcc   9240
ctggactttt atcctacttc tcctggggat tgtcacccac ctacccgtgt ctgtcctttg   9300
ttgctttgac gctgtcactt cttttcttag gtacctctct gtagggctcc attattccag   9360
ggattccaga gttacagcac atgcatacct ccatccaagc atgtttattt gtctcctgct   9420
tcactaggct gtccccaagg aacatgtggc tcccggcaca tacctggcac aacactgcac   9480
atgacattca cccacttggc cttgaatctg acaaggaatc tggcatgatg ttcacctgct   9540
gaggccaggt gccgagcagc cctggaggct taggggccag agggatggga aaaggtgtct   9600
ttctggggtg agtatcagtt tctgcaggag tgctgaacct gagaaagaat aaagagagaa   9660
ggaagtgaac aagcacagct taaacatcat ctgtttctac tgagttttaa caactctgag   9720
attttgtttg tcatggaatc catttctcag gccaagcaga cacagaactt gggtgtgagt   9780
gatgataatg agctgatata attttcacac cctcatcact gagatctctc ccatcaggaa   9840
tgggtcacag ggctcacagg tggcagcaac tgttattaca ggcctcatct ctaccagctc   9900
ctggcacctc ctctcctctc attagaaaat cctccacttg tcaaaaagga agccatttgc   9960
tttgaattcc aattccaccc tcaagaggct gggaccacct cattggagtc cttgatgctg  10020
```

```
tgtgacctgc agtgaccact gccccattgt tgctggctga ggtggtttgg gtcaacctgg    10080
ccatctgggc agctgttctc ttctcttctt tctccctac tgtttccaga catgcagtat     10140
ttccagagag aagggccac tctttggcaa agaacctgtc taacttttcta tctacggcag    10200 gacttttgaa agctacagag gaagaagcac aaattgatgc tattccacta agccatcagc   10260
tccatctcat ccatgccatg tctctttttt aggggtcctc ttgccaacag aatcacagag   10320
gacaaatctg aaagtgcaga gacagcagct gaggcacagc caagagctct ggctgtatta   10380
atgacctaag aagatggagt ggtcaccaga aagtcagagg aagtgacaca caggggccca   10440
gcaatctcag ccaagtcaac tccaccagcc tttctggtcc ccactgtgtg tacagcaccc   10500
tgatagggac cagagccatg agagtgagta agaccagact atgcccttga ggagctcacc   10560
tctgctaagg gaaacaggcc tggaaacaca caatggtggt aaagaggaaa gaagacaata   10620
gaactgcatg aagggatgg aaagtgccca gggaggaaa tggttacttc tgtgtgaggg     10680
ggttggtgag gaaagactct aagagaaggc tctgtctggc tgggtatgaa aggatgtgta   10740
ggagtcttct aggggggcaca ggcacactcc aggcataggt aaagatctgt aggcatggct  10800
tgttgggatg agtttcaagt attctggaat gaggacagcc atagagacaa gaggagagtt   10860
aatagatttt atgccaatgg ctccacttga gtttgtgata agaacccaga accctttggac  10920 tccccagtaa cattgattga gttgtgtatg attctacata gaatattaac tcaatggagg   10980
tcagtgagtg gtgtgtgtgt gattatttgc caactgccga ggtggagaag cctcttccga   11040
ctgcaggcag agcacggggg ccctgctact ggctgcagct ccagccctgc ctccttctcc   11100
agcatataaa caatccaaca gcctcactga atcactgctg tgcagggcag gaaagctcca   11160
cacacacagc ccagcaaaca gcagca                                         11186

<210> SEQ ID NO 5
<211> LENGTH: 10200
<212> TYPE: DNA
<213> ORGANISM: Homo sapiens

<400> SEQUENCE: 5
gccaattaga agaaacacaa ctacaaggtc agggcatatt attcaaacag tagagacaat     60
acagtcaaat atttggcaga attacaaaat atctcattgg aaaagacacg caagggaaat   120
caacaaaaag atatgaatca gaattcatct gtgtctcaag aaaaggtcat gcgataaatt   180
aagttctgct agtgtttcta cactaccgtt agcctcatta ccttattttt taagtgttaa   240
tatagtttta ggtattttac atacattttt attattaatt acaaccaaag tgcaacttgt   300
aatagcaatt ccttcacatt ttttttttca aatcttgcac cttaaaatcc acctcgggcc   360
tcagttggcc agctttggta tctgatactt ggactacaga taccactaag gcaagtagat   420
aaaatgtact ctaggaccta cagcccttct gctagatcct gaagaatgat cattaaaaca   480
agctggtcta gctggtcaag agcaaaaata aaatcaagat gacagaaaat tgatgcaaaa   540
gtgaagtaaa atagctagag aatatgattg cgcctgtccc cttagcatgg attcccatgc   600
tagccaatct aaaatcctca ctgttagaat cctcctgtca atatgataga atgaacagca   660
agctcagtgt cagaaaacct gtgttgttaa cttggccctc tttctagctg aatgtgtgtt   720
tttggtcaag ttcttttggca tttcagagac tcagagtagt gaaggaagtg gataagatga   780
cctctacatt ctcttgcaag ctcaaacatc tatgaatcca gagagaaaaa ctagagcatg   840
aaattaaggt tattttaaag aaataacctt aaaattatta gtattcgagg atctccaata   900
tattcatggc accactcaaa actttccttc tgctctatcc cgtcttggct caaagttatc   960
```

```
tccttaatga ggtctgccct gactatccta cttaaaattg taaactttgc ccacctggta   1020
cttccactct cttcccctg ctctgttttt caccgtaata ctttactctt tttaacatac    1080
aaaatcactt atttactgtg ttgttatcta tctgcctact cttaccatca aatataagtt   1140
ctacctaggc agggattttt gtatgttttg ctcatggata tatacgaagc acttagagta   1200
atatgtgaca tatacagggt acttgattaa tactgttgag tgaatgaatg agtttccaat   1260
acaaatttaa aataaaatat ttcctaactt aaaattgtaa agtcagatct aaccaactgt   1320
tcattggtct gctagcagtg tttcttgtat atggaaatat attttaaata gatatgtcct   1380
gtgaataat actaagtgtt ctaaagaaat aagtgagtga acgttacctc attgaactaa    1440
cttgaccttg ctcctgggag agagttcatt tgagattaaa caagttcaaa gtctatgaat   1500
cataaaacga taaaaaaac taaaagggaa atggtgtttt tataagctct gcaattcaaa    1560
agccatttcg ggtaatattg ttatttttat gtcaggaatt cctcagtgct gatatcttag   1620
ggcaaagggt ttggttataa attaagagaa tgaggaaata ggtacatagt aggattgttc   1680
caaccaaata tgtgttgaat gtcaaaggaa tttccctgag gaataatctt cagaataatt   1740
tgctaagcac aggagaaaat ttggcttatt actttatagc cagatttcat ttttaattga   1800
aacttctttc aagcaaatca cttactagtc tattaacaat aacaacataa acacaagtaa   1860
acattcggaa tatagacatc caggtactaa gctgattgct ttacactcac tgtcttattt   1920
tacaagtaag gagttttagt tgcagcaaaa gaaataaatt ttccaatgtc aaatgaccag   1980
aacttaaacc caatctgttt ggtgctaaag ccaatgttct ttactgcaat gttgggttat   2040
cttgtttcta aaacttaaat ttatcagtaa aaggcaaaat ttgctattat tgaggacatt   2100
aaaatcatat ttttgtagac tctgaggaca aatccaacaa aaaagttcca actatttctt   2160
ggcaggcatc attgaaattg gtatatagct tccttgggta ttgactttga aaaggaagtt   2220
ggtcacttta gatatataag ttcagtctgt ttgtaaaaac aaaatgaaaa caaacagtt    2280
gccttatatg ctaaaattat cctaatcgtt ttcacccttta acaacatata cacacagaac  2340
ttgaggaact ttacacggct catcttcata ttgtcagcat ctagcaaagt acttgccaca   2400
tagtgatcaa taaaagttt agccagcctg ggcaacatag tgacagccta tctctacaaa    2460
aaaaaattag ccaggcaagg tggcgcacac ctttggtccc agctacttga gaggaggatg   2520
tggggagatc ctttgaatgc aggaggttga ggctgcagtg agctgtgatt gcgccactgt   2580
gcttcaacct tggtgacaga gcaagaccct gtctcacaca cacacaaatt aagtaaagaa   2640
aaaaaaaga atcaaagaaa aaaataattc cccagcttaa gtccatcttt atttgtttgg   2700
ataagctata aagtgtcaaa taatgctgtt aatggacatt tctctagctc tcccaaagga   2760
ggaattgagc acatagtatg tgctgtattt tatatacaga ataaaaatag agacaagatt   2820
tctaccctca cagaacttaa attcttcagg agaatgacac tgaagtcctt aattggactt   2880
ctctcttctg tattatcttc ctcaagtgga ggtatatggt gcttagttat gaaaaatacc   2940
tccagggctt tgatcttctc aataactctt tgaggctgat atgaaaacag taattagaaa   3000
aaaaccatgt atccaactta tatagacagt tgatgaccaa agctagaatc cagttatttc   3060
agcctcccat gtattttctt attacttaag gagaatctct atctctacct ctttctctct   3120
tcttcctctc tcacttttct tagaaacatg ggtaagattt tcagaaatat gagaaactta   3180
ttaataaatg aaaaatactg ggaattctca atgtttcttg ttttagccag ttaattttgg   3240
ccttcattca atgtgagtgt cccttaataa ggagcaaact ccactgagag atagatacta   3300
ataaccagga ttctgaaaat gcattctcat ccccatctcc aaactttat aaaaaatatt     3360
```

```
ataaaataat acacttttaa tataggaaat ttctcaaata cagaaaaaat taaagtaaac    3420
tcagacctaa ctttcatcac taaaagataa tcactcttga cactttgata tctttatctc    3480
taatattaca ccaattaatt tgcttgatat agtgaatatt atgctattat aattttcccc    3540
tgccttttgt ccttgcatat tagcataggt attttctgag gttatcacaa actctgtaag    3600
cacgttttat attactactt ttttaaagag gatgtataat aattaattca tccatatata    3660
tgtggttaag tattcaggtc actgctcatt tttcactgtt ataaaataaa gcagcaatga    3720
atacctttgg ctgatatttt tttctgtact tggaattatt tctttaagat agatttccta    3780
aaattgaatt actgagtcaa acagacttaa gttttcctta tgtatgtttc cttattcatt    3840
tgaataattt tcaactccta cttgtttatt taactcttgt gagcatgtga tagtctcatt    3900
tttcaaaata tctttgctgt tgtaatttgc atttctttgt agttagcatg aatatttcag    3960
tatgttttct tctgtgtacc agtatactac atactttttt atatgaattg cctatttgca    4020
tcttttgctc ggttctatta gacctttgaa ttttttctta tccatttata taagctcttt    4080
atatattaag aatattaacc tattgtgata tttgcaataa atagctatat ggtttgttgt    4140
tggttttaaa tgtgaattta ttcaattttc ttcataattt tgttgttttt atagatttct    4200
ttaaaagtaa taaaattatt gccatattat tatttatttt caatgtccat tactagccct    4260
ttccagtcat cacttttact ctcatgttct taattttat tcatatcttg gctccattga    4320
ccatctttat taggatattt gggaaataat acaatttata ctaaacacac atcaaatctt    4380
accttatttt cttcttacaa aaaccctagg aatatgctgt ttttgtcttt atttgaatga    4440
cacagaaatc aaggtttttg agcagtggag tatttcttca aatgacacag aaatcaagtc    4500
ttttgagcag tggagtattt cttcaaagcc acacagctag taagtcatga agctggaatt    4560
ccaagagttg ccacttcatt ttcttctttc cctttatctt actcagttgt cttctctcct    4620
cttaattttg tcattcattt aaaaacattt cttgtgctat tatggtagat ttattttaat    4680
agggggcagt gacttactca gagagatgat tctctaatgg agttttaaag atcttagaag    4740
ttgatagagg aggctgggcg tggtggctca tgcctataat cccagcactt tgggaggctg    4800
aggtgggtgg atcacttgag gccagaagtt caagatcagc ctagtcaatg tggtgaaacc    4860
ccatttctac taaaattaca aaaattagcc tggtgtgctg gtgcactccc ataatcccag    4920
ctactcagga ggctgaggca tgagaattgc tggaacccag gaggcggagg ttgcagtgcg    4980
cctggattat taacactaca ctccagcctg ggagacagag taatactcca tctcaataaa    5040
aagaagttga taagggagat agttcatggc aacggatctt tgaaggcacg ctaatgataa    5100
cttaggcatt tagcctacta gtgtaatttc cataaatctg cctctgatgt catactctca    5160
gcacctaata ttttctacaa acatttattg aaactttatt ttgtataagt ctctgtccag    5220
tttgaatatt taaaaaattc ataatcatat gaaacattaa taataaatac aaaatgagag    5280
atgccgatac tgaaaagtag gattgcggag tggtagaaaa tatttctggc tgtagtagat    5340
ggggaagtgt tcaaagagga gtataattca ggtttccatt tgccatcgac ttatcacatg    5400
gctaactcac taagcgactt aattaaaatt aaattaattt atcatcatct gatcaccatt    5460
tcacacaact catgtctgtt gctgtattgg ctaaatgatg gcaagacaaa cgacctctga    5520
aaatgatcct attgaccttc ggaatctgga tttttttttc aatgcaggtg tccatagaag    5580
caatctgatg taatccaaca tgagttcaag cacagtcatt taatatcccc tatcaagtac    5640
agtcatttaa tatcccctat catcacatgt ccttcataca taaaaatcat tacatgtgaa    5700
agggtggaga gtgtgtggat cccttattat tgtgttattg taacacaata acaatattgt    5760
```

```
gttattattg ttaacacaag tgagtcatat gtcttgctct ttggactgag tggaaacttg    5820
tattctttct ctgcctcagg tcaattaact tcattgaggt gagttgcatt ccttctttaa    5880
gcatgttgaa ccttcaatct ggactcgat gggctaaata gaggagctag gaaaaataca    5940
gaaaataaat tattagagag atcagagaaa gatacataag atttacaata aaagaattat    6000
gagaaaaaca tccaaaagaa ttaaaaacca taggagaagg aaaaataggt gaacagcttt    6060
ttaatttcta taaatgtgtt gttaatactc ataataaagg actcagagct gggatatgag    6120
aataataggt caaacgtata tggatacata gatgtgacta catacatgag ttgcaaagaa    6180
tgctaaggag ggcaaaaaga gattgagaag agggcattat tactaatata tagcaatgtt    6240
gaatgtttag ggtgtttcag gcactgtaca aatcttttaa atacacaaat cacttaatct    6300
tgccataaca ttagaagata ctatctactc tttaccaaaa aggtaactgt gggatagcag    6360
agttaagtaa cccgttcaaa cctatgcata taatcagca gagatggtcc ttatctaagt    6420
ttttctgcct ttgaagtcca aatagtttaa tgcagccagg tactaaagaa gaaaactttt    6480
gtaaattagt ttagtttaat gatttacatg tggaaaagca cagagtgaaa agcacatatc    6540
atctgagaag cccagtgagt ttggctgaaa tggagtgaac atgtacatgt tgagggtgag    6600
gaagatgatt agagagaagt gatgtgttgt ggttcttaaa agctaagagg aaactgttag    6660
atatgatata gtctgtggca gggagccatt gcaggttttc caagatggac tcataaggag    6720
aaaacacttc gtgggactgg aaaaggcagt gaagtggtgt gtcctatgat aatgtactac    6780
agtgtaggat agtggttaag agtacagtta tgagagaggg actactggtt agcaccttac    6840
ctgctgtgtg actgggcaaa taatgcaaac ctcagtgtct tttattgtaa tatgggagta    6900
acaaaaatag taactacttc ataggattct tgtaaagatt aaatgactta atttctttga    6960
agtgcttggc agttcctgat aaatgaccag tagttaataa atgttagttg ttattattat    7020
cattatatat tattactccc atagatacat atagaacaga ctgcagcaga gaggcaaatc    7080
tttaatgttg tcagagtata gacaagttgg tgaaatggct acatgagagc ggaggacaag    7140
aaggtgcaga ttgtggcagt cacttcaaat ggaaatatca ccgcttgaat gaaggtatat    7200
gagtgtcaac ttgcaagggg accaggtagg tttcatcaga aattaaggaa gcttaaggag    7260
aacagccaag ttcagcttga cagaagtggt ggtggcacaa atgcaagact ggtgtctttc    7320
aagaaaccaa ggactgttga agtagcaag agctagtttg tttaggtcc atcatgtttt    7380
atattcacac tttcatgtca gtggagcaaa gaaatggaat acaatataat agaatggtag    7440
aatcttattt ttaaaatctg tgttattctg atctttaact tacttatatc tttgatagag    7500
atctttacct gatgctcaag attgtagaaa tagtataatc aacataacag tatagcactg    7560
tatttatatc ctgcactgtt tagggagggt ttaaggccat tcaaaggat acataaaata    7620
caacaagatt acataaatga aaggtgagat aaagcaacaa agcaaacaa aagtgaaaac    7680
agagatcata ggcacaaata agattaaaaa cgcatgtaat gaagatgaaa gcttttacat    7740
ttaccccaga tggaccacag ggttgttgtt aagcctttaa acagtgaaca atgctgtaca    7800
cttgcatatg caattagaac atgtggaaaa aatagtggcc tgttagaagc ctaattaaca    7860
atttgtgaaa aaaaaaaaa aaaaaaaaa aagaggccga gctgtagctc acgcctgtaa    7920
tcccctgcact ttgggaggcc gaggcgggcg gatcacgagg tcaggagatc aagaccatcc    7980
tggctaacac agtgaaaccc agtctctacg aaaatacaa aaattagcc gggcgtggtg    8040
gcgggagcct gtagtcccag ctacctggga ggctgaggca ggagaatggt gtgaacccgg    8100
gaggcggagc ttgcagtgag ccgagatcct gccactgcac tccagcctgg gcgacaaagc    8160
```

```
aagactccgt ctcaaaaaag aaaaaagaaa gaaaaacaaa agaaaacttc attgtattgt    8220
aaggccaaga acaaaatata tcaagataag gaaaatttgt agtcaagaat agaaaaaaat    8280
tatggctttg aagtatgagt tatttaaaga aagtggaaac atcctcagac tatgcagtaa    8340
aaaacaaagt gattttcttc ttctaaactt atgcaataaa ctgataggta atatgtgaaa    8400
gtcatagaat gtagactaga ggatacaaca aacctatttc ctctatgttc ataagaagta    8460
agaaaagctc tgatgtgagt tagcattgct ttacaatttt gaattgtgca gattgcacgt    8520
acttttcctc agtttgaagt aaatagtgga caggaaaaaa tattaaatgt tggcagtaaa    8580
tatggaagga aattacaact aatgtaatat gctaaaacat gctatgttta ttttactaat    8640
ttgaattaaa atgtaagaat ttaaaatgcc ctggaaaaac acgggcattg atctgacgtc    8700
tgaagtttta aaatattaca cactttgaaa tagcatttgt accttgaaat acctgtctct    8760
atatatttt taaaacttcc tttttctttc attccattta tcatcaaata aaggatgaac    8820
agatgtaact cagaaactgt caagcatgct gaagaaagac cactgcagaa aaatttctcc    8880
tagcctttc aaaggtgtta ggaagcagaa aggtgataca gaattggaga ggtcggagtt    8940
tttgtattaa ctgtattaaa tgcgaatccc gagaaaattt cccttaacta cgtcctgtag    9000
ttatatggat atgaagactt atgtgaactt tgaaagacgt gtctacataa gttgaaatgt    9060
ccccaatgat tcagctgatg cgcgtttctc tacttgccct ttctagagag gtgcaacgga    9120
agccagaaca ttcctcctgg aaattcaacc tgtttcgcag tttctcgagg aatcagcatt    9180
cagtcaatcc gggccgggag cagtcatctg tggtgaggct gattggctgg gcaggaacag    9240
cgccggggcg tgggctgagc acagccgctt cgctctcttt gccacaggaa gcctgagctc    9300
attcgagtag cggctcttcc aagctcaaag aagcagaggc cgctgttcgt ttcctttagg    9360
tctttccact aaagtcggag tatcttcttc caaaatttca cgtcttggtg gccgttccaa    9420
ggagcgcgag gtaggggcac gcaaagctgg gagctactat gggacagttc ccaagtgtca    9480
ggctttcaga tttcctgaac ttggtcttca cgggagaagg gcttcttgag gcgtggatag    9540
tgtgaagtcc tctggcaagt ccatggggac caagtggggt tagatctaga ctcaggagct    9600
cctggagcag cgcccaaacc gtagtggcac tggaccatgt tgcccggagc gcgcacagcc    9660
cgcgcggtgc ggggacctgc tctctgagcc cgcgggcggt gggtgggagg aagcatcgtc    9720
cgcggcgact ggaaccggga gggagaatcg cactggcggc gggcaaagtc cagaacgcgc    9780
tgccagaccc ccaactctgc cttcgtggag atgctggaga ccccgcgcac aggaaagccc    9840
ctgcagtgcc catcgcggcc agagcagctg gggcatcaac ggcgggcgct ccctcttact    9900
gctctctggc ttcgacgggg gactagaggt tagtctcacc tccagcgcgc ctgaggctca    9960
tgcatttggc taatgagctg cggtttctct tcaggtcgga atggatcttg aaggggaccg   10020
caatggagga gcaaagaaga agaacttttt taaactgaac aataaaaggt aactagcttg   10080
tttcattttc atagtttaca tagttgcgag atttgagtaa tttatttcta gcctccagct   10140
ctgaaataaa tgacatgttg ttgttttttaa ttatttttaa gaaacgcaag ctagcctttg   10200
```